(12) United States Patent
Shaffer et al.

(10) Patent No.: US 10,539,776 B2
(45) Date of Patent: Jan. 21, 2020

(54) IMAGING SYSTEMS WITH MICRO OPTICAL ELEMENT ARRAYS AND METHODS OF SPECIMEN IMAGING

(71) Applicant: SamanTree Medical SA, Lausanne (CH)

(72) Inventors: Etienne Shaffer, Le Mont-sur-Lausanne (CH); Bastien Rachet, Lausanne (CH); Aurèle Timothée Horisberger, Chavannes-Près-Renens (CH); Jonathan Abel Pirolet, Aclens (CH); Diego Joss, Renens (CH)

(73) Assignee: SamanTree Medical SA, Lausanne (CH)

( * ) Notice: Subject to any disclaimer, the term of this patent is extended or adjusted under 35 U.S.C. 154(b) by 0 days.

(21) Appl. No.: 16/146,695

(22) Filed: Sep. 28, 2018

(65) Prior Publication Data

US 2019/0137752 A1    May 9, 2019

Related U.S. Application Data

(60) Provisional application No. 62/675,368, filed on May 23, 2018, provisional application No. 62/675,638, (Continued)

(51) Int. Cl.
*G01J 3/46* (2006.01)
*G02B 21/36* (2006.01)
(Continued)

(52) U.S. Cl.
CPC .......... *G02B 21/367* (2013.01); *A61B 90/20* (2016.02); *G01N 21/6428* (2013.01); (Continued)

(58) Field of Classification Search
CPC .... G02B 21/367; G02B 21/16; G02B 21/082; G02B 21/0036; G02B 21/0032; (Continued)

(56) References Cited

U.S. PATENT DOCUMENTS

| 3,814,504 A | 6/1974 | Brady et al. |
|---|---|---|
| 4,927,254 A | 5/1990 | Kino et al. |

(Continued)

FOREIGN PATENT DOCUMENTS

| DE | 19632594 A1 | 2/1998 |
|---|---|---|
| DE | 19729245 C1 | 5/1999 |

(Continued)

OTHER PUBLICATIONS

International Search Report, International Application No. PCT/EP2018/079894 (Confocal Scanning Imaging Systems With Micro Optical Element Arrays and Methods of Specimen Imaging, filed Oct. 31, 2018), issued by ISA/European Patent Office, 7 pages, dated Apr. 29, 2019.

(Continued)

*Primary Examiner* — Abdullah Nur
(74) *Attorney, Agent, or Firm* — William R. Haulbrook; Michael D. Schmitt; Choate, Hall & Stewart LLP

(57) ABSTRACT

Disclosed herein are systems for imaging of samples using an array of micro optical elements and methods of their use. In some embodiments, an optical chip comprising an array of micro optical elements moves relative to an imaging window and a detector in order to scan over a sample to produce an image. A focal plane can reside within a sample or on its surface during imaging. Detecting optics are used to detect back-emitted light collected by an array of micro optical elements that is generated by an illumination beam impinging on a sample. In some embodiments, an imaging system has a large field of view and a large optical chip such (Continued)

that an entire surface of a sample can be imaged quickly. In some embodiments, a sample is accessible by a user during imaging due to the sample being exposed while disposed on or over an imaging window.

40 Claims, 29 Drawing Sheets
(7 of 29 Drawing Sheet(s) Filed in Color)

Related U.S. Application Data filed on May 23, 2018, provisional application No. 62/597,346, filed on Dec. 11, 2017, provisional application No. 62/579,827, filed on Oct. 31, 2017.

(51) Int. Cl.
| | | |
|---|---|---|
| A61B 90/20 | (2016.01) | |
| G01N 21/64 | (2006.01) | |
| G02B 21/00 | (2006.01) | |
| G02B 21/08 | (2006.01) | |
| G02B 21/16 | (2006.01) | |
| H04N 5/225 | (2006.01) | |
| H04N 7/18 | (2006.01) | |

(52) U.S. Cl.
CPC ..... *G02B 21/0012* (2013.01); *G02B 21/0032* (2013.01); *G02B 21/0036* (2013.01); *G02B 21/082* (2013.01); *G02B 21/16* (2013.01); *H04N 5/2256* (2013.01); *H04N 7/18* (2013.01); *G01N 2021/6439* (2013.01)

(58) Field of Classification Search
CPC .............. G02B 21/0012; G02B 21/008; G02B 21/0076; G02B 21/0024; H04N 7/18; H04N 5/2256; G01N 21/6428; G01N 2021/6439; A61B 90/20
See application file for complete search history.

(56) References Cited

U.S. PATENT DOCUMENTS

| | | |
|---|---|---|
| 5,161,053 A | 11/1992 | Dabbs |
| 5,257,128 A | 10/1993 | Diller et al. |
| 5,463,223 A | 10/1995 | Wong et al. |
| 5,580,827 A | 12/1996 | Akamine |
| 5,689,109 A | 11/1997 | Schutze |
| 6,052,224 A | 4/2000 | Richardson |
| 6,133,986 A | 10/2000 | Johnson |
| 6,185,030 B1 | 2/2001 | Overbeck |
| 6,335,824 B1 | 1/2002 | Overbeck |
| 6,348,999 B1 | 2/2002 | Summersgill et al. |
| 6,392,752 B1 | 5/2002 | Johnson |
| 6,424,852 B1 | 7/2002 | Zavislan |
| 6,937,886 B2 | 8/2005 | Zavislan |
| 7,193,782 B2 | 3/2007 | Menon et al. |
| 7,225,010 B1 | 5/2007 | Zavislan |
| 7,285,089 B2 | 10/2007 | Viellerobe et al. |
| 7,312,919 B2 | 12/2007 | Overbeck |
| 7,628,865 B2 | 12/2009 | Singh |
| 7,706,043 B2 | 4/2010 | Uhl et al. |
| 7,759,635 B2 | 7/2010 | Boer et al. |
| 7,968,839 B2 | 6/2011 | Merenda et al. |
| 8,121,670 B2 | 2/2012 | Zavislan |
| 8,553,337 B2 | 10/2013 | Webb et al. |
| 8,606,343 B2 | 12/2013 | Zavislan |
| 9,075,227 B2 | 7/2015 | Rachet et al. |
| 9,333,036 B2 | 5/2016 | Ben-Yakar et al. |
| 9,563,044 B2 | 2/2017 | Kosanic et al. |
| 9,678,323 B2 | 6/2017 | Orth et al. |
| 10,088,427 B2 | 10/2018 | Rachet et al. |
| 2001/0048467 A1 | 12/2001 | Fiedler |
| 2002/0088858 A1 | 7/2002 | Tanaami et al. |
| 2003/0032204 A1 | 2/2003 | Walt et al. |
| 2003/0147083 A1 | 8/2003 | Hill |
| 2004/0012853 A1 | 1/2004 | Garcia et al. |
| 2004/0125370 A1* | 7/2004 | Montagu ............ G01N 21/0303 356/244 |
| 2004/0204651 A1 | 10/2004 | Freeman et al. |
| 2004/0256542 A1 | 12/2004 | Okazaki |
| 2004/0264856 A1 | 12/2004 | Farr |
| 2005/0014201 A1 | 1/2005 | Deuthsch |
| 2005/0018199 A1 | 1/2005 | LeBlanc |
| 2005/0098717 A1 | 5/2005 | Grier et al. |
| 2005/0146794 A1 | 7/2005 | Menon et al. |
| 2006/0077536 A1 | 4/2006 | Bromage et al. |
| 2006/0121298 A1 | 6/2006 | Wittke et al. |
| 2006/0163463 A1 | 7/2006 | Grier |
| 2007/0235640 A1 | 10/2007 | Gruber et al. |
| 2007/0251543 A1 | 11/2007 | Singh |
| 2008/0030742 A1 | 2/2008 | Hill |
| 2008/0121790 A1 | 5/2008 | Grier |
| 2009/0028407 A1 | 1/2009 | Seibel et al. |
| 2009/0190221 A1 | 7/2009 | Boer et al. |
| 2009/0225409 A1 | 9/2009 | Ilev et al. |
| 2010/0200739 A1 | 8/2010 | Anderson et al. |
| 2010/0207016 A1 | 8/2010 | McBride et al. |
| 2011/0116694 A1 | 5/2011 | Gareau |
| 2011/0211104 A1 | 9/2011 | Hendriks |
| 2011/0300490 A1 | 12/2011 | Rachet et al. |
| 2012/0133757 A1 | 5/2012 | Thomas et al. |
| 2013/0211391 A1 | 8/2013 | BenYakar et al. |
| 2014/0193892 A1 | 7/2014 | Mohan et al. |
| 2015/0085289 A1 | 3/2015 | Kang |
| 2015/0198793 A1 | 7/2015 | Kosanic et al. |
| 2015/0355449 A1 | 12/2015 | Orth et al. |
| 2016/0091799 A1 | 3/2016 | Rachet et al. |
| 2016/0305926 A1 | 10/2016 | Rachet et al. |
| 2017/0150872 A1 | 6/2017 | Kosanic et al. |
| 2018/0348142 A1 | 12/2018 | Rachet et al. |
| 2019/0129158 A1 | 5/2019 | Shaffer et al. |

FOREIGN PATENT DOCUMENTS

| | | |
|---|---|---|
| EP | 0294902 A1 | 12/1988 |
| EP | 0991959 B1 | 6/2004 |
| EP | 1548481 A1 | 6/2005 |
| EP | 2299307 A2 | 3/2011 |
| EP | 1011441 B1 | 7/2011 |
| GB | 2408587 A | 6/2005 |
| WO | WO-90/01716 A1 | 2/1990 |
| WO | WO-97/34171 A2 | 9/1997 |
| WO | WO-1999/03008 A1 | 1/1999 |
| WO | WO-03/035824 A1 | 5/2003 |
| WO | WO-03/056378 A1 | 7/2003 |
| WO | WO-03065774 A1 | 8/2003 |
| WO | WO-2004/025668 A2 | 3/2004 |
| WO | WO-2005/096115 A1 | 10/2005 |
| WO | WO-2007/042989 A1 | 4/2007 |
| WO | WO-2008/012767 A2 | 1/2008 |
| WO | WO-20091064746 A2 | 5/2009 |
| WO | WO-2010/084478 A2 | 7/2010 |
| WO | WO-2011/091283 A1 | 7/2011 |
| WO | WO-2014/013412 A1 | 1/2014 |
| WO | WO-2016/156516 A2 | 10/2016 |
| WO | WO-2017/001537 A1 | 1/2017 |
| WO | WO-2019/086550 A2 | 5/2019 |

OTHER PUBLICATIONS

Written Opinion, International Application No. PCT/EP2018/079894 (Confocal Scanning Imaging Systems With Micro Optical Element Arrays and Methods of Specimen Imaging, filed Oct. 31, 2018), issued by ISA/European Patent Office, 11 pages, dated Apr. 29, 2019.

Afzal, R. S. et al., Optical Tweezers Using a Diode Laser, Review of Scientific Instruments, IAP 63(4):2157-2163 (1992).

Casaburi, A. et al., Two-and three-beam interferometric optical tweezers, Optics Communication, 251(4-6):393-404 (2005).

(56) References Cited

OTHER PUBLICATIONS

Constable, A. et al., Demonstration of a Fiber-Optic Light-Force Trap, Optics Letters, Optical Society of America, 18(21)1867-1869 (1993).

Cuche, E. et al., Digital Holography for quantitative phase-contrast imaging, Optics Letters, 24(5):291-293 (1999).

Davidson, N. et al, High-numerical-aperture focusing of radially polarized doughnut beams with a parabolic mirror and a flat diffractive lens, Optics Letters, 29(12)1318-1320 (2004).

Engelbrecht, C. J. et al., Ultra-compact fiber-optic two-photon microscope for functional fluorescence imaging in vivo, Optics Express, 16(8):5556-5564 (2008).

Glaser, A. K. et al., Light-sheet microscopy for slide-free non-destructive pathology of large clinical specimens, Nature Biomedical Engineering, 1 (0084):1-10, (2017).

Guenther, R. et al., Device for the Optical Analysis of Samples, DE19729245C1, machine translation.

Hell, S. W. et al., Breaking the diffraction resolution limit by stimulated emission: stimulated-emission-depletion flourescence microscopy, Optics Letters 19(11):780-782 (1994).

Moktadir, Z. et al., Etching techniques for realizing optical microcavity atom traps on silicon, J. Micromech. Microeng., 14(9)S82-S85 (2004).

Orth, A. and Crozier, K., Gigapizel fluorescence microscopy with a water immersion microlens array, OSA, 21(2):Optics Express 2361, 8 pages. (2013).

Orth, A. and Crozier, K., Microscopy with microlens arrays: high throughput, high resolution and light-field imaging, OSA, 20(12):Optics Express 13524, 10 pages (2012).

Schmitt, J. M., Optical Coherence Tomography (OCT): A Review, IEEE Journal of Selected Topics in Quantum Electronics, 5(4):1205-1215 (1999).

Tiziani, H. J. et al., Three-dimensional analysis by a microlens-array confocal arrangement, Applied Optics, 33(4):567-572 (1994).

Walecki, W. J. et al., Fast in-line surface topography metrology enabling stress calculation for solar cell manufacturing for throughput in excess of 2000 wafers per hour, Measurement Science and Technology, 19(025302):6 pages (2008).

Zemanek, P. et al., Optical Trapping of Nanoparticles and Microparticles by a Gaussian Standing Wave, Optics Letters, Optical Society of America, 24(21)1448-1450 (1999).

Zhao, Y. et al., Development of a versatile two-photon endoscope for biological imaging, Biomedical Optics Express, 1(4):1159-1172 (2010).

\* cited by examiner

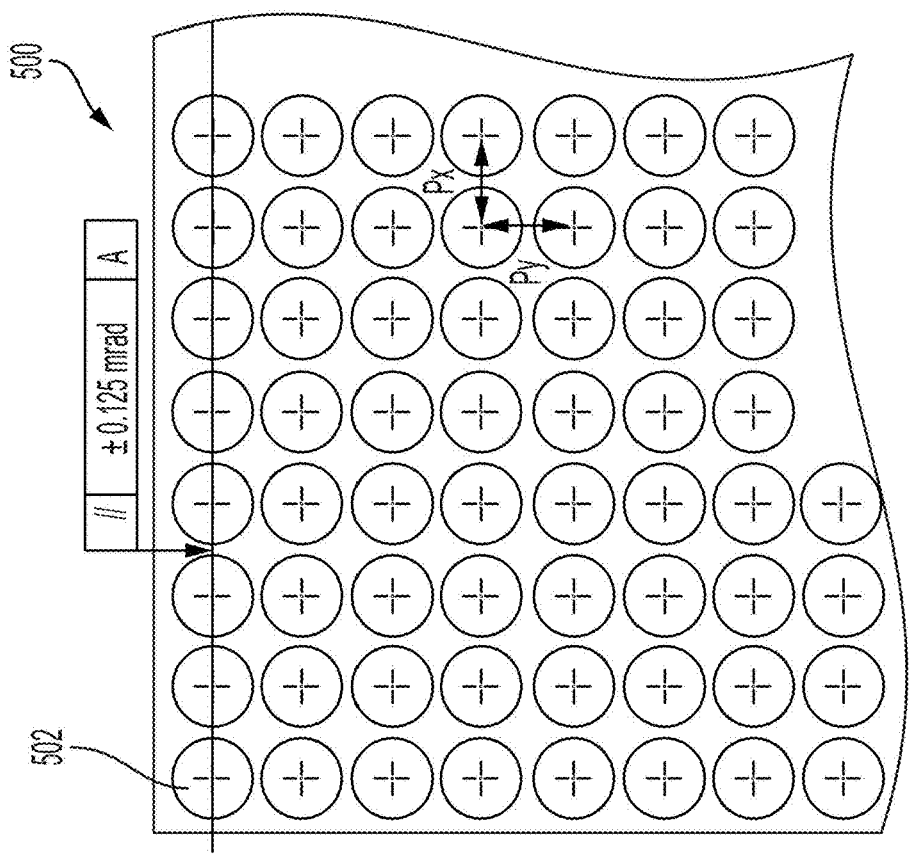
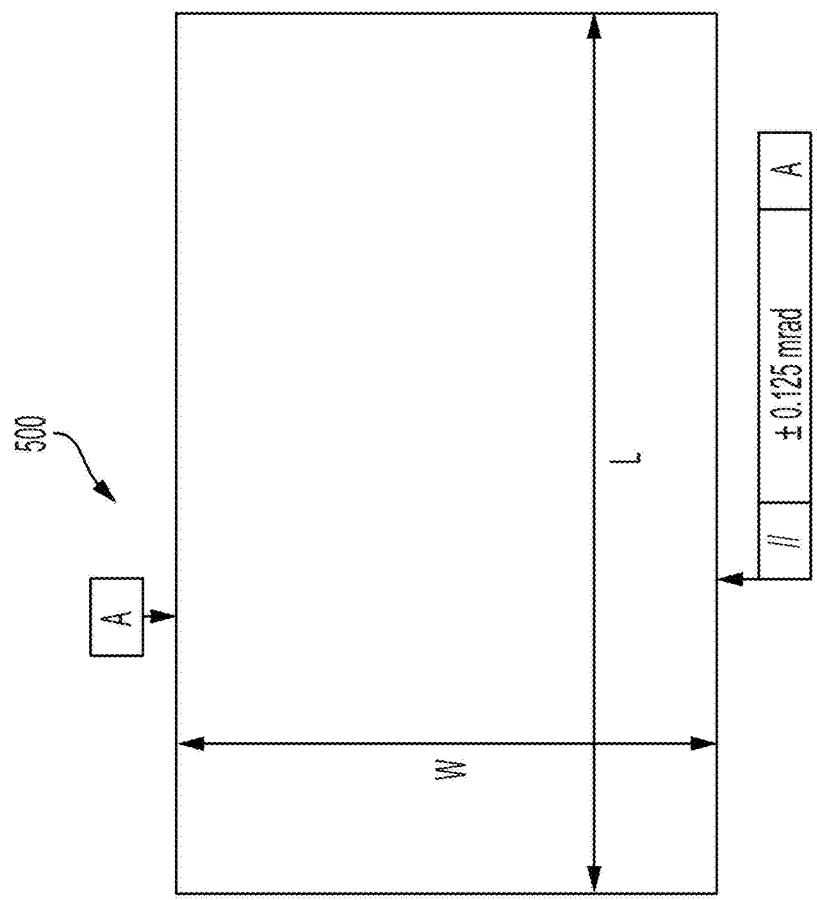
FIG. 5B
FIG. 5A

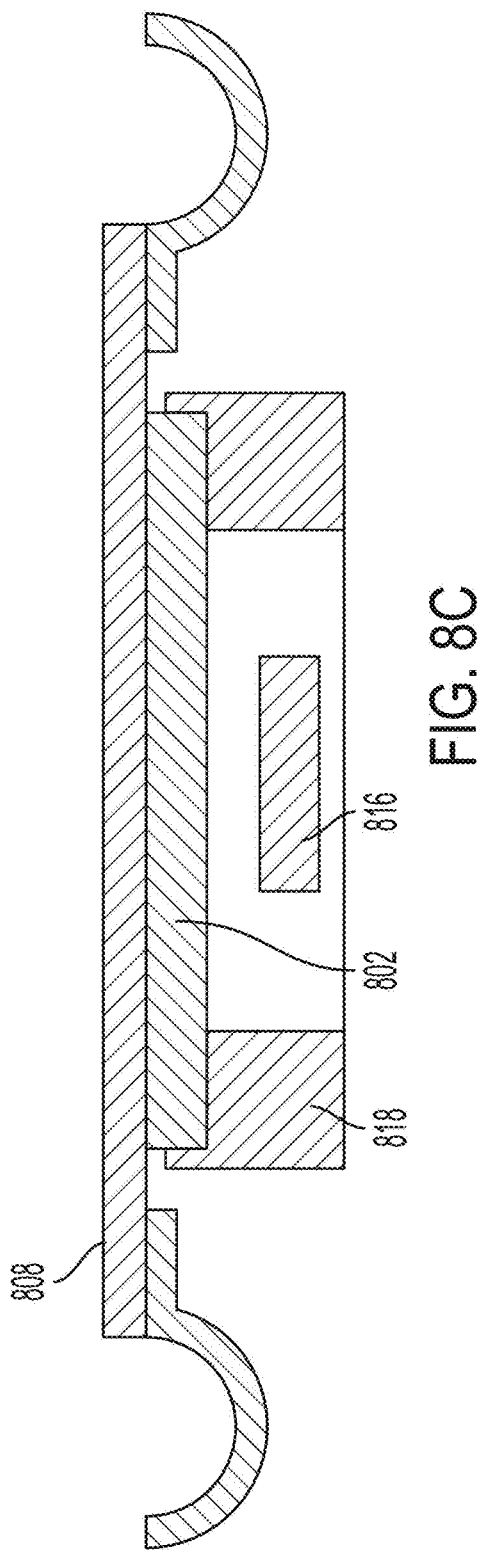

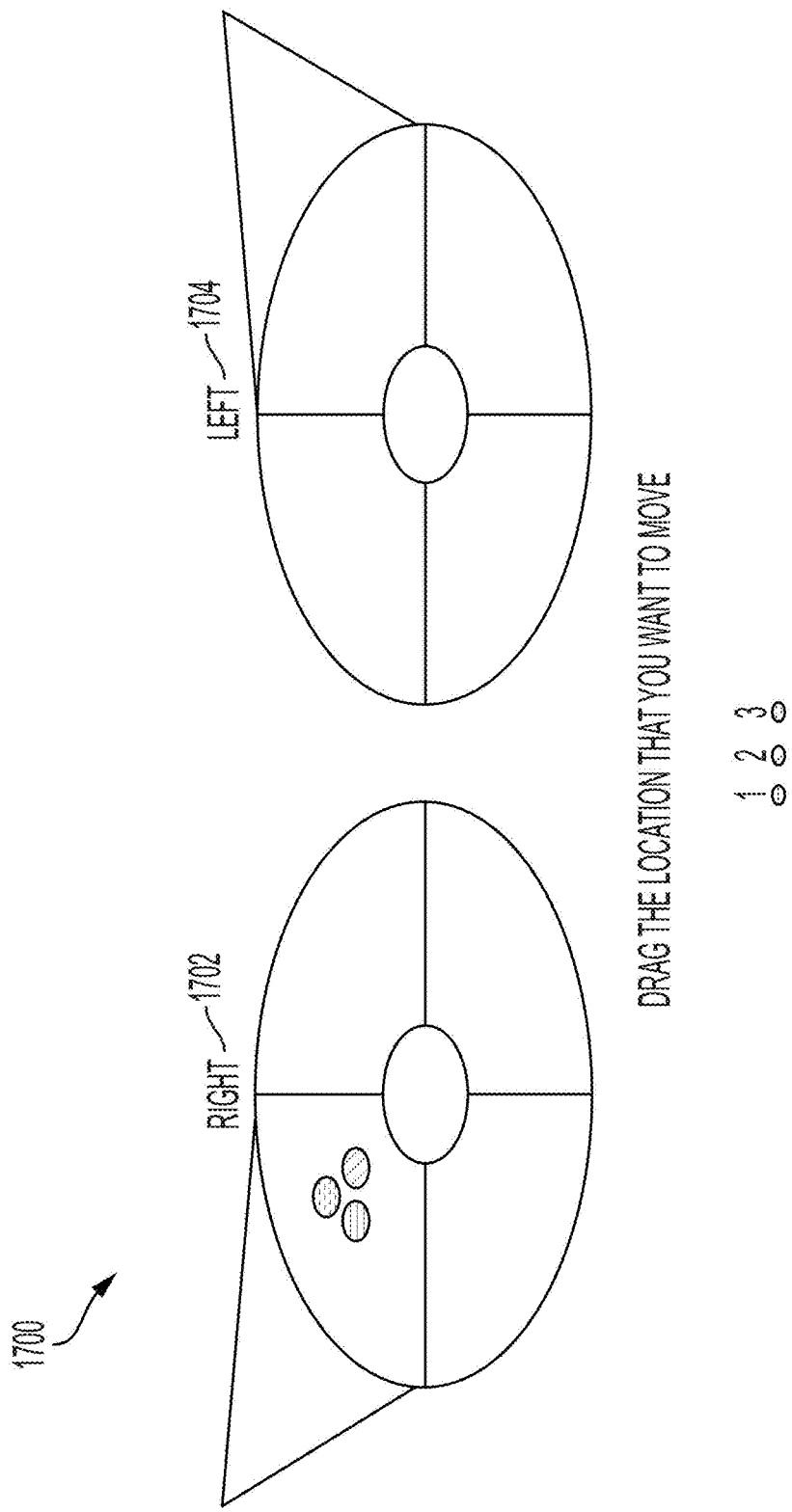

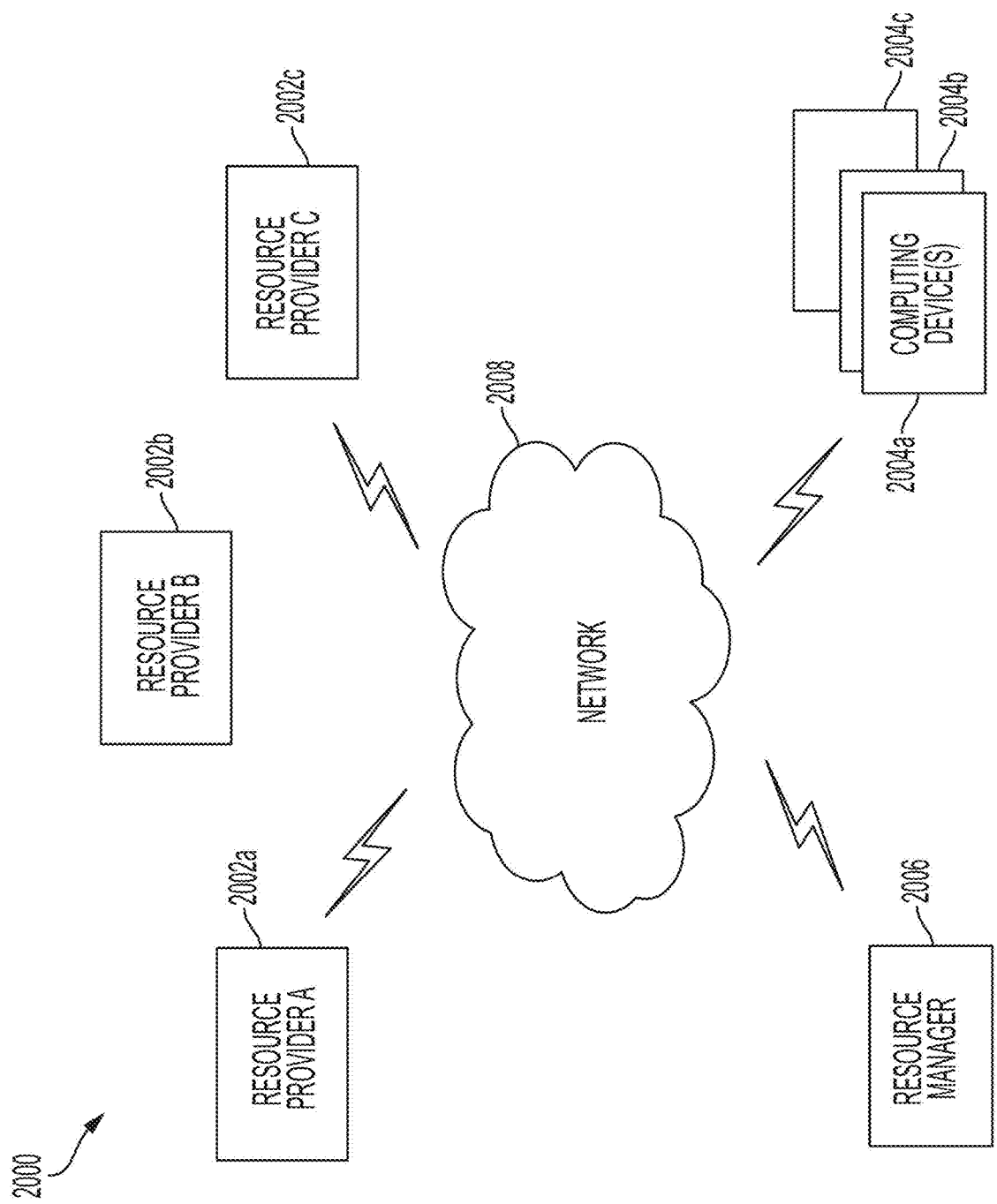

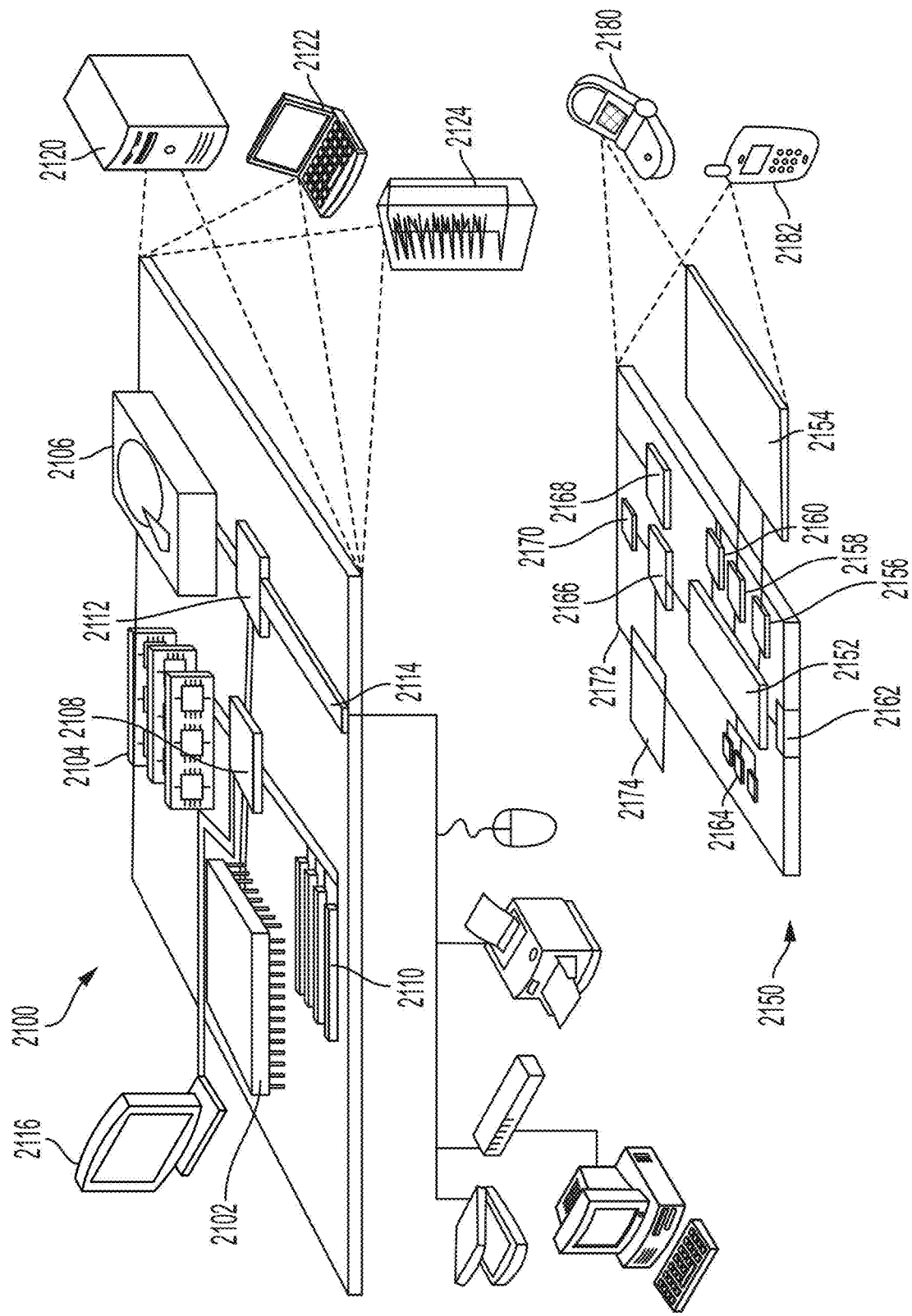

IMAGING SYSTEMS WITH MICRO OPTICAL ELEMENT ARRAYS AND METHODS OF SPECIMEN IMAGING

PRIORITY APPLICATIONS

The present application claims the benefit of U.S. Provisional Patent Application No. 62/579,827, filed Oct. 31, 2017, entitled "Imaging Systems for Imaging Samples Using an Array of Micro Optical Elements and Methods of Their Use," U.S. Provisional Patent Application No. 62/597,346, filed Dec. 11, 2017, entitled "Imaging Systems for Imaging Samples Using an Array of Micro Optical Elements and Methods of Their Use," U.S. Provisional Patent Application No. 62/675,638, filed May 23, 2018, entitled "Systems and Methods for Imaging Specimens," and U.S. Provisional Patent Application No. 62/675,368, filed May 23, 2018, entitled "Sample Dishes for Use in Microscopy and Methods of Their Use," each of which is hereby incorporated by reference herein in its entirety.

TECHNICAL FIELD

The present disclosure relates generally to systems for imaging samples (e.g., intraoperatively imaging resected fresh tissue) and methods of imaging samples.

BACKGROUND

Solid epithelial cancers account for over 10% of all deaths each year world-wide. This figure is expected to increase. Early-stage cancer diagnosis and subsequent complete surgical removal of tumor(s) offers the best chance for complete cancer cure. When early-stage cancer is detected in a patient, minimally invasive techniques may be used to cure the patient. However, to alleviate the need for further treatment (e.g., chemotherapy), a complete resection of the tumor must be made. Non-complete resections require further treatment by re-operation, chemotherapy, or similar. During typical surgical removal procedures of tumors, a surgeon resects a tissue sample comprising a tumor surrounded by a margin to ensure total removal of all cancer cells. Generally, a surgeon desires to limit the volume resected to only slightly more than the volume of the tumor in order to limit the amount of healthy tissue resected. However, resecting with smaller margins increases the likelihood that less than the whole tumor is resected.

After resection, a surgeon must make an intraoperative assessment of whether the resected volume includes the whole tumor. In order to preserve tissue integrity, a surgeon generally has no more than about 30 minutes to make an intraoperative assessment of a tissue resection. Currently, surgeons use visual inspection and palpation to make an intraoperative assessment. In some cases, X-ray, ultrasound, or magnetic resonance imaging are used to provide supplementary qualitative assessments. These imaging modalities provide only approximate (e.g., low resolution) assessments of resection margins. A full pathological assessment of resection margins to determine sufficient and complete removal of a tumor (i.e., with appropriate margins) is only made post operatively. Consequently, a high percentage of resection surgeries result in re-operation to make a second resection.

SUMMARY

Tumor residues may remain undetected and untreated until they grow to advanced stages, at which point both patient death rate and overall treatment costs can dramatically increase. For certain indications, this results in the need to re-operate on many patients days after the initial operation when an analysis is obtained from the histopathology laboratory. Such follow-up surgical procedures usually lead to less favorable outcomes for the patient, psychological stress, and, in some cases, can roughly double treatment and hospitalization costs. Current techniques to improve intra-operative assessments, such as intra-operative frozen section (FSA), require the prolongation of operation time by at least 30 minutes, which, in addition to inconvenience for the patient and the clinical personnel, results in increased cost of the surgery and complications for operating theatre planning and management. Further, many tumor surgeries today do not include pathologic margin assessment, primarily due to the inconvenience and cost of a frozen section analysis. Certain resected tissue sample are quite large (e.g., as large as on the order of 1000 $cm^3$ in volume) and therefore require significant time to image. Thus, there is a need for systems and methods for more efficient (e.g., faster) imaging of samples (e.g., in-operating-theater intraoperative assessment of resected tissue by imaging). Faster tissue imaging also has benefits outside of in-operating theater applications, such as increased throughput in laboratory settings or improved workflows in hospitals (e.g., in pathology departments).

Disclosed herein are systems and methods for imaging of samples (e.g., fresh resected tissue) using an array of micro optical elements and methods of their use. In some embodiments, an optical chip comprising an array of micro optical elements moves relative to an imaging window and a detector in order to scan over a sample to produce an image. A photon source provides an illumination beam that is directed by optics to an optical chip in order to focus light using an array of micro optical elements (e.g., micro lenses). A focal plane can reside within a sample or on its surface during imaging. Detecting optics are used to detect back-emitted light collected by an array of micro optical elements. In some embodiments, an imaging system has a large field of view and a large optical chip (e.g., a large array of micro optical elements) such that an entire surface of a sample (e.g., a 10 cm×10 cm×10 cm) can be imaged in a short period of time (e.g., less than 30 minutes). In some embodiments, a sample is accessible by a user during imaging (e.g., for ease in maintaining position and/or fast and easy repositioning) due to an exposed sample mounting surface comprising an imaging window.

In certain embodiments, the disclosed technology allows intraoperative assessments (e.g., in an operating theater) comparable in quality to traditional post-operative histopathological assessments. The disclosed technology includes systems that can analyze, for example, in an operating theatre, "optical slices" of fresh tissue without having to fix the resected tissue by freezing and/or processing with formalin or paraffin, as is done in traditional histopathology assessments. This greatly reduces the time necessary for preparing and analyzing a sample and facilitates in-operating-theater analysis of tissue samples obtained during surgery. In certain embodiments, sample mounting and positioning can be performed freely by a surgeon (e.g., using the surgeon's hands or a standard surgical tool).

In certain embodiments, the disclosed technology allows image data (e.g., data associated with an image of the specimen) to be associated with orientation data (e.g., data associated with an orientation of an imaged specimen relative to an imaging system used to image the specimen) and/or location data (e.g., data associated with the location on a body from which the sample was obtained). For example, imaging system orientation data corresponding to the orientation of the tissue specimen during imaging can be received to associate the image data with the orientation data. The image data may then be stored (e.g., in a database) along with the orientation data, allowing, for example, a user to efficiently track orientation of a sample when imaging more than one face of a specimen (e.g., during a whole surface mapping).

In one aspect, the present invention is directed to a system for imaging (e.g., fluorescence, luminescence, or reflectance imaging) of a sample [e.g., a fresh tissue sample resected during surgery (e.g., cancer surgery) for intraoperative resected tissue assessment], the system comprising: a transparent imaging window, wherein the transparent imaging window provides a surface onto or over which a sample (e.g., a fluorescent-stained fresh sample) (e.g., an unsliced sample preserved for definitive assessment in follow-up testing) is disposed during imaging of the sample; a photon source (e.g., laser or other photon source providing light with a wavelength of 488 nm or between 450-490 nm) for providing an illumination beam; a beam splitter (e.g., dichroic mirror/filter, prism, or grating(s)) for directing the illumination beam toward the imaging window [e.g., directly or indirectly (e.g., using one or more additional mirrors)]; a collimating lens for collimating the illumination beam over an area comparable in size to a field (e.g., corresponding to the sample) to be illuminated (e.g., wherein the field is at least 40 mm×30 mm), thereby providing a collimated illumination beam, wherein the collimating lens is disposed between the imaging window and the beam splitter such that the illumination beam is directed to the collimating lens by the beam splitter; an optical chip, wherein the optical chip comprises an array of micro optical elements (e.g., comprising one or more of refractive lenses, Fresnel zone plates, micro reflective objectives, and GRIN lenses) (e.g., an array of micro lenses) for focusing the collimated illumination beam onto a focal plane above or on the imaging window (e.g., on a side of the imaging window opposite to a side on which the optical chip is disposed) (e.g., wherein the focal plane lies on a surface of the sample or within the sample when imaging the sample disposed on or above the imaging window), wherein each micro optical element of the array of micro optical elements: (i) focuses a portion of the collimated illumination beam onto a tight focus (e.g., a small spot) [e.g., such that the array of micro optical elements forms an array of tight foci in the focal plane (e.g., for exciting fluorescence in the sample)], and (ii) directs back-emitted light from the sample through the collimating lens and towards the beam splitter (e.g., directs light emitted from the sample, e.g., fluorescent light, through the collimating lens and towards the beam splitter); a detector, the detector comprising an array of detector elements [e.g., an array of pixels in a camera (e.g., a CCD or CMOS camera)], wherein the back-emitted light directed towards the beam splitter by each element of the array of optical elements of the optical chip passes through the beam splitter during imaging such that the at least a portion is incident on the detector; and a scanning stage comprising a support, a controller, and an actuator, wherein: (i) the optical chip is attached (e.g., directly or indirectly) to the support and the controller and actuator are operable to move the optical chip along a scan pattern relative to the imaging window and the detector during imaging in order to form an image of the sample (e.g., a scanned confocal image) (e.g., to construct an optical slice of the sample) (e.g., such that only the optical chip is in motion during imaging), or (ii) the support is attached (e.g., directly or indirectly) to the imag-ing window and the controller and actuator are operable to move the imaging window along a scan pattern relative to the optical chip and the detector during imaging in order to form an image of the sample (e.g., a scanned confocal image) (e.g., to construct an optical slice of the sample).

In certain embodiments, the system comprises an imaging lens for collimating the back-emitted light such that the back-emitted light is collimated by the imaging lens after passing through the beam splitter.

In certain embodiments, the optical chip is attached (e.g., directly or indirectly) to the support and the controller and actuator are operable to move the optical chip along a scan pattern relative to the imaging window and the detector during imaging in order to form an image of the sample (e.g., a scanned confocal image) (e.g., to construct an optical slice of the sample) (e.g., such that only the optical chip is in motion during imaging).

In certain embodiments, the imaging window and the detector are in a fixed relative position (e.g., during imaging of the sample).

In certain embodiments, the support is attached (e.g., directly or indirectly) to the imaging window and the controller and actuator are operable to move the imaging window along a scan pattern relative to the optical chip and the detector during imaging in order to form an image of the sample (e.g., a scanned confocal image) (e.g., to construct an optical slice of the sample).

In certain embodiments, the optical chip and the detector are in a fixed relative position (e.g., during imaging of the sample).

In certain embodiments, the photon source is a laser and, optionally, the laser emits at least one of (i) a Gaussian beam and (ii) a beam with a half-power beam width of less than 1.5 mm in diameter. In certain embodiments, the laser emits a wavelength of between 450 nm and 500 nm (e.g., between 480 nm and 490 nm or about 488 nm). In certain embodiments, the laser has a power of at least 5 mW (e.g., at least 20 mW, at least 50 mW, at least 80 mW, at least 100 mW, at least 150 mW, or at least 200 mW).

In certain embodiments, the photon source has reduced temporal coherence (e.g., is a light-emitting diode or super luminescent diode (SLED)).

In certain embodiments, the system comprises a focusing lens (e.g., an aspheric focusing lens) disposed in an optical path of the illumination beam from the photon source to the beam splitter. In certain embodiments, the focusing lens has a focal length of between 1 mm and 2 mm (e.g., between 1.3 mm and 1.7 mm, between 1.4 mm and 1.5 mm, or about 1.45 mm) [e.g., wherein the focusing lens has a lens diameter of between 2 mm and 3 mm (e.g., between 2.2 mm and 2.8 mm or about 2.4 mm)]. In certain embodiments, the focusing lens has a focusing lens focal length and the collimating lens has a collimating lens focal length, each of which depends on a diameter of the illumination beam emitted by the photon source such that an illumination profile of the collimated illumination beam produced by the collimating lens has less than a 50% difference (e.g., less than a 40% difference, less than a 30% difference, less than a 20% difference, less than a 10% difference) in intensity between an area of highest intensity in the illumination profile and an area of lowest intensity in the illumination profile (e.g., wherein the illumination profile has a size comparable to the field to be illuminated). In certain embodiments, the illumination profile is at least 48 mm×36 mm in area. In certain embodiments, the photon source provides an illumination beam that is a Gaussian beam with a half-power beam width of less than 1.5 mm in diameter (e.g., a half-power beam width of about 1.0 mm in diameter) and the collimating lens focal length is at least 40× larger (e.g., about 60× larger) than the focusing lens focal length.

In certain embodiments, the system comprises a first aperture disposed in the optical path of the illumination beam between the focusing lens and the beam splitter [e.g., wherein the first aperture has a diameter of between 0.5 mm and 1.5 mm (e.g., about 1.0 mm)].

In certain embodiments, the beam splitter is a dichroic mirror. In certain embodiments, the dichroic mirror has a reflection band that is in a range of between 400 nm and 600 nm (e.g., between 450 nm and 500 nm) and a transmission band that is in a range between 450 nm and 1000 nm (e.g., between 500 nm and 850 nm). In certain embodiments, the dichroic mirror has an area of at least 100 mm2 and/or no more than 1200 mm2 (e.g., about 900 mm2).

In certain embodiments, the collimating lens is a cemented doublet lens (e.g., a cemented achromatic doublet lens).

In certain embodiments, the collimating lens has a focal length of at least 100 mm (e.g., at least 150 mm or at least 200 nm).

In certain embodiments, the collimating lens has a diameter of at least 50 mm [e.g., at least 60 mm, at least 70 mm or at least 75 mm (e.g., about 75 mm)].

In certain embodiments, the system comprises a filter (e.g., an emission filter) for filtering undesired light (e.g., light from the photon source), wherein the filter is disposed in an optical path of the back-emitted light such that at least a portion of the back-emitted light passes through the filter. In certain embodiments, the filter is disposed between the beam splitter and the detector (e.g., in infinity-space between the imaging lens and the detector) along the optical path of the back-emitted light. In certain embodiments, the emission filter is a long-pass filter (e.g., having a cut-off wavelength of at least 400 nm, at least 450 nm, at least 500 nm, or at least 600 nm). In certain embodiments, an opaque enclosure is disposed about an optical path of the back-emitted light that passes through the filter from the filter to the detector (e.g., thereby preventing light from being incident on the detector without passing through the filter).

In certain embodiments, the system comprises a second aperture disposed in an optical path of the back-emitted light between the beam splitter and the detector. In certain embodiments, the second aperture is disposed in the optical path of the back-emitted light between the imaging lens and the beam splitter. In certain embodiments, the second aperture has a diameter of between 1 mm and 5 mm [e.g., between 2 mm and 4 mm (e.g., about 3 mm)]. In certain embodiments, the optical chip, the collimating lens, the second aperture, the imaging lens, and the detector in a 4f configuration (e.g., with the optical chip in a focal plane of the collimating lens, the second aperture in a common focal plane of the collimating lens and the imaging lens, and the detector is in a focal plane of the imaging lens).

In certain embodiments, (i) the second aperture is disposed in a focal plane common to the collimating lens and the imaging lens and (ii) the optical chip is closer to the collimating lens (e.g., than the second aperture).

In certain embodiments, the imaging lens is a cemented doublet lens (e.g., a cemented achromatic doublet lens).

In certain embodiments, the imaging lens has a focal length of between 10 mm and 30 mm (e.g., between 15 mm and 25 mm, between 18 mm and 22 mm, or about 19 mm) [e.g., wherein the imaging lens has a lens diameter of between 6 mm and 15 mm (e.g., between 10 mm and 13 mm or about 12.7 mm)].

In certain embodiments, the detector is a camera [e.g., with a resolution of at least 320×240 pixels (e.g., at least 640×480 pixels)]. In certain embodiments, the detector has a frame rate of at least 250 frames per second [e.g., at least 300 frames per second, at least 400 frames per second, at least 500 frames per second (e.g., about 500 frames per second)].

In certain embodiments, a ratio of micro optical elements in the array of micro optical elements to detector elements in the array of detector elements is from 1:1 to 1:100, 1:1 to 1:10, 1:5 to 1:12, 1:5 to 1:80, 1:20 to 1:70, 1:30 to 1:60, or 1:40 to 1:50 (e.g., about 1:1, 1:2, 1:3, 1:4, 1:6, 1:8, 1:9 or 1:12, e.g., to the nearest whole number, or within a range of any two of these values).

In certain embodiments, the micro optical elements of the array of micro optical elements are disposed on a surface (e.g., integral with a surface) of the optical chip. In certain embodiments, areas on the surface of the optical chip between and/or around micro optical elements of the micro optical element array are coated with an absorptive and/or reflective layer (e.g., a chromium layer, an aluminum layer, or a dielectric mirror layer) (e.g., wherein the absorptive and/or reflective layer fully covers inter-lens area of the optical chip on the surface on which the array of micro optical elements is disposed) [e.g., wherein the absorptive and/or reflective layer has an optical density of no less than 1 (e.g., no less than 2 or no less than 3)]. In certain embodiments, the absorptive and/or reflective layer acts as an aperture for each micro optical element and a diameter (e.g., a lens diameter) of each micro optical element is no smaller than a diameter of a corresponding aperture defined by the absorptive and/or reflective layer.

In certain embodiments, the optical chip has a thickness of less than 2.0 mm (e.g., less than 1.5 mm or about 1.5 mm) [e.g., with a total thickness variation and/or total flatness deviation of less than 20 μm (e.g., less than 15 μm, less than 10 μm, or less than 5 μm)].

In certain embodiments, the array of micro optical elements has an area of at least 30 mm×20 mm (e.g., at least 40 mm×30 mm or at least 50 mm×35 mm) (e.g., of about 54.5 mm×37 mm).

In certain embodiments, the optical chip comprises fused silica.

In certain embodiments, the array of micro optical elements has a pitch of between 100 μm and 400 μm (e.g., between 200 μm and 300 μm or about 250 μm) (e.g., wherein a variation in pitch between micro optical elements of the micro optical element array is no more than 6 μm, no more than 4 μm, or no more than 2 μm).

In certain embodiments, the array of micro optical elements is a regular array and a pitch of micro optical elements in the array in a first direction equals a pitch of micro optical elements in the array in a second direction that is perpendicular to the first direction (e.g., wherein the array comprises a square lattice of a micro optical elements).

In certain embodiments, a parallelism of each set of opposing edges of the array of micro optical elements is better than about ±0.250 mrad (e.g., no more than or about ±0.125 mrad).

In certain embodiments, the array of micro optical elements comprises from 1000 to 100,000 micro optical elements [e.g., from 20,000 to 60,000 micro optical elements or from 50,000 to 70,000 micro optical elements (e.g., about 30,000 micro optical elements or about 60,000 micro optical elements)].

In certain embodiments, each micro optical element of the array of micro optical elements has a convex surface (e.g., at least one convex surface).

In certain embodiments, the convex surface of each micro optical element has a shape obtained by the revolution of a conic section [e.g., with a radius of curvature of between 200 µm and 300 µm].

In certain embodiments, the convex surface of each micro optical element has a conic constant from −1.8 to −2.2 (e.g., about −2 or about −2.05 or between about −2 and about −2.05).

In certain embodiments, each micro optical element has a spot size from 0.2 µm to 5 µm (e.g., 0.2 µm to 2 µm, 0.8 µm to 3 µm, or 1 µm to 2 µm).

In certain embodiments, a focal length of each micro optical element in the array of micro optical elements is between 100 µm and 700 µm (e.g., between 200 µm and 600 µm or 500 µm to 600 µm) (e.g., about 550 µm).

In certain embodiments, the micro optical elements in the array of micro optical elements collectively focus onto a common focal plane (e.g., wherein each element of the micro optical element array focuses onto a single point on the common focal plane).

In certain embodiments, at least the support and the actuator of the scanning stage and the optical chip are confined (e.g., fully confined) within the system such that at least the support and the actuator of the scanning stage and optical chip are protected from the sample (e.g., and the outside environment) at least in part by the imaging window when the sample is disposed on or over the imaging window.

In certain embodiments, the imaging window comprises at least one of glass, quartz, sapphire, and plastic (e.g., is a single uniform material or is a multilayer stack comprising a plurality of materials).

In certain embodiments, the imaging window is hard (e.g., scratch resistant) (e.g., at least as hard or harder than stainless steel) and/or impact resistant.

In certain embodiments, the imaging window comprises (e.g., consists essentially of) sapphire (e.g., wherein the c-axis of the sapphire is substantially parallel to an optical axis of the optical chip).

In certain embodiments, the imaging window has a high Young's modulus [e.g., a Young's modulus of at least 100 GPa (e.g., at least 200 GPa or at least 300 GPa)] (e.g., such that the imaging window does not appreciably deflect when the sample is disposed thereon or thereover).

In certain embodiments, the imaging window has a thickness of no more than 900 (e.g., no more than 800 no more than 600 no more than 400 or no more than 300 µm) (e.g., between 200 µm and 800 µm, between 400 µm and 600 µm, or about 500 µm).

In certain embodiments, the imaging window is free standing over a surface that is at least as large as the field of view (e.g., is at least as large as an area corresponding to a scan range of the scanning stage).

In certain embodiments, the transparent imaging window comprises an anti-reflection coating coated on a surface of the transparent imaging window.

In certain embodiments, the scanning stage is a three-axis positioning stage (e.g., a high precision three-axis positioning stage) or a two-axis positioning stage (e.g., high precision two-axis positioning stage).

In certain embodiments, the scanning stage has a precision of equal to or better than 5 (e.g., equal to or better than 3 equal to or better than 2 equal to or better than 1 µm).

In certain embodiments, the scanning stage is configured to bring the imaging window in close proximity to the array of micro optical elements (e.g., within 100 µm).

In certain embodiments, the scanning stage is a computer actuated scanning stage (e.g., synchronized with the detector).

In certain embodiments, the system comprises a housing that at least partially encloses the system and exposes the sample to ambient conditions (e.g., is uncovered) during imaging. In certain embodiments, the housing comprises a window support upon which a sample dish containing the sample may be disposed and held on or over the imaging window during imaging (e.g., thereby providing unobstructed access to the sample), such that the sample and the sample dish are accessible to a user during imaging (e.g., without removal of a lid). In certain embodiments, the window support is attached to the imaging window, and the window support and the imaging window are both sized and shaped to accommodate an optical interface of a sample dish (e.g., with the sample disposed on the optical interface) (e.g., during imaging).

In certain embodiments, the window support is disposed on a window support base of the housing that is recessed from an upper working surface of the housing, the imaging window is recessed below the upper working surface of the housing, and the imaging window is attached (e.g., glued) to the window support such that the imaging window projects above the window support. In certain embodiments, the imaging window is disposed at least partially in a common plane with the upper working surface.

In certain embodiments, the system comprises a computing device, wherein the computing device comprises a processor and a memory having instructions stored thereon that, when executed by the processor, cause the processor to produce (e.g., construct) an image (e.g., a confocal image) based on the back-emitted light detected by the detector. In certain embodiments, the memory has instructions stored thereon that, when executed by the processor, cause the processor to construct an image representing an optical slice of the fresh tissue sample based on the back-emitted light detected by the detector. In certain embodiments, the memory has instructions stored thereon that, when executed by the processor, cause the processor to send information regarding the detected back-emitted light (e.g., an image captured by the camera) to a receiving device (e.g., a second computing device or a display) (e.g., remote from the first computer device—e.g., outside an operating theatre in which the system is located). In certain embodiments, the memory has instructions stored thereon that, when executed by the processor, cause the processor to: connect the computing device, by the processor, with an operating theater display system (e.g., comprising one or more monitors visible in an operating theater); and output, by the processor, imaging data to the operating theater display system (e.g., in real time, e.g., wherein the imaging data comprises video data). In certain embodiments, the memory has instructions stored thereon that, when executed by the processor, cause the processor to: connect, by the processor, to a radiology picture archiving and communication system (PACS) and/or a pathology PACS; and at least one of (i) retrieve, by the processor, one or more stored images from the radiology PACS and/or the pathology PACS and (ii) store the image of the sample into the radiology PACS and/or the pathology PACS. In certain embodiments, the memory has instructions stored thereon that, when executed by the processor, cause the processor to: connect the computing device, by the processor, to a laboratory information system; and receive and/or send, by the processor, data to the laboratory information system. In certain embodiments, the memory has instructions stored thereon that, when executed by the processor, cause the processor to: connect the computing device, by the processor, to an electronic patient record system; and receive and/or send, by the processor, data to the electronic patient record system.

In certain embodiments, the computing device is configured to connect to a cloud server for storing images.

In certain embodiments, the computing device sends a signal to the controller of the scanning stage.

In certain embodiments, the memory has instructions stored thereon that, when executed by the processor, cause the processor to: determine (e.g., recognize), by the processor, an area or volume of a 2D or 3D image of the sample that is indicative of cancer and/or high cancer risk [e.g., using machine learning and/or artificial intelligence (e.g., using a training set of images)], wherein the 2D or 3D image of the sample is obtained using the system; and output, by the processor, a representation of the area or volume (e.g., for rendering and/or display) (e.g., to highlight the area or volume on the image when the representation of the area or volume is displayed simultaneously with the image).

In certain embodiments, the memory has instructions stored thereon that, when executed by the processor, cause the processor to: generate, by the processor, a fixed number of masks [e.g., based, at least in part, on one or more scan characteristics (e.g., scan size and/or scan resolution) and/or one or more system characteristics (e.g., detector resolution or detector type)], wherein the fixed number of masks is independent of (i) a number of scan points in a scan and (ii) a number of micro optical elements in the array of micro optical elements; and reconstruct, by the processor, an image based, at least in part, on the fixed number of masks (e.g., wherein no other masks are used in reconstruction).

In certain embodiments, the system comprises a kinematic support structure [e.g., comprising at least three feet (e.g., four) of adjustable height], the support structure supporting the imaging window (e.g., directly or indirectly by supporting the window support that the imaging window is attached to) such that the height and tilt of the imaging window relative to the optical chip are adjustable (e.g., wherein one or more feet of the kinematic support structure are adjustable).

In certain embodiments, the system comprises a touch screen monitor for controlling the system.

In certain embodiments, the system comprises a joystick and one or more input buttons for controlling the system [e.g., wherein the joystick and one or more input buttons are connected to the system by one or more cords (e.g., such that the joystick and one or more input buttons can be remote (e.g., separated by some distance) from other components (e.g., the imaging window) of the system)].

In certain embodiments, the sample is stained with a fluorescent stain (e.g., proflavine, acridine orange, hematoxylin or eosin).

In certain embodiments, the system is operable to image a portion of the sample [e.g., for in-operating-theatre imaging of tissue (e.g., fresh tissue) resected during surgery (e.g., cancer surgery)] in less than 10 minutes (e.g., less than 5 minutes, less than 3 minutes or less than 2 minutes).

In certain embodiments, the system comprises the system is operable to image a portion of the sample [e.g., for in-operating-theatre imaging of tissue (e.g., fresh tissue) resected during surgery (e.g., cancer surgery)] in less than 2 minutes (e.g., less than 90 seconds or less than 1 minute). In certain embodiments, the portion of the sample has an area of at least 10 $cm^2$ (e.g., at least 12 $cm^2$, at least 15 $cm^2$, or at least 17 $cm^2$).

In certain embodiments, the system comprises the sample has a volume of no more than 10 cm×10 cm×10 cm and the system is configured to image a full outer surface of the sample in an imaging time of no more than 45 minutes (e.g., no more than 30 minutes).

In certain embodiments, the system is a Class 1 laser product according to an ANSI standard and/or an IEC standard (e.g., according to ANSI Z136.1, IEC 825, and/or IEC 60825).

In another aspect, the invention is directed to a method for in-operating-theatre imaging of tissue (e.g., fresh tissue) resected during surgery (e.g., cancer surgery) for intraoperative resected tissue assessment, the method comprising: intraoperatively resecting tissue to obtain a fresh tissue sample; procuring an image of an intraoperatively resected fresh tissue sample (e.g., using the system of any one of the embodiments described herein) [e.g., wherein the procuring step is completed within 90 minutes (e.g., 60 minutes, 40 minutes, 30 minutes, 10 minutes or 5 minutes) of the resection of the fresh tissue sample]; and optionally, sending, by a processor of a first computing device, to a receiving device (e.g., a second computing device or a display) (e.g., remote from the first computer device—i.e., outside the operating theatre) the image of the fresh tissue sample.

In another aspect, the invention is directed to a method of reconstructing an image using a system (e.g., a confocal microscopy system) comprising an optical chip comprising an array of micro optical elements (e.g., micro lenses), the method comprising: generating, by a processor of a computing device, a fixed number of masks [e.g., based, at least in part, on one or more scan characteristics (e.g., scan size and/or scan resolution) and/or one or more system characteristics (e.g., detector resolution or detector type)], wherein the fixed number of masks is independent of (i) a number of scan points in a scan and (ii) a number of micro optical elements in the array of micro optical elements; and reconstructing, by the processor of the computing device, an image based, at least in part, on the fixed number of masks (e.g., wherein no other masks are used in reconstruction).

In another aspect, the invention is directed to a method for imaging a sample [e.g., in-operating-theatre imaging of fresh tissue resected during surgery (e.g., cancer surgery) for intraoperative resected tissue assessment], the method comprising: for each of a plurality of positions of a scan pattern: providing, by a photon source (e.g., laser or other light source providing light with a wavelength of 488 nm or between 450-490 nm), an illumination beam for illuminating the sample (e.g., wherein the sample is a fluorescent stained, fresh sample or a preserved sample—i.e., unsliced thereby preserving the sample for definitive assessment), wherein the sample is disposed on or over a transparent imaging window (e.g., on a sample dish disposed on or over the transparent imaging window) (e.g., in an operating theatre), directing the illumination beam via illumination optics onto the disposed on or over the transparent imaging window, wherein the illumination optics comprise: a beam splitter (e.g., dichroic mirror/filter, prism, or grating(s)) for directing the illumination beam toward the imaging window [e.g., directly or indirectly (e.g., using one or more additional mirrors)], a collimating lens for collimating the illumination beam over an area comparable in size to a field (e.g., of the sample) to be illuminated (e.g., wherein the field is at least 40 mm×30 mm), thereby providing the collimated illumination beam, wherein the collimating lens is disposed between the imaging window and the beam splitter such that the illumination beam is directed to the collimating lens by the beam splitter, and an optical chip, wherein the optical chip comprises an array of micro optical elements (e.g., comprising one or more of refractive lenses, Fresnel zone plates, micro reflective objectives, and GRIN lenses) (e.g., an array of micro lenses) for focusing the collimated illumination beam onto a focal plane above or on the imaging window (e.g., on a side of the imaging window opposite to a side on which the optical chip is disposed), wherein the focal plane lies on a surface of the sample or within the sample, wherein each micro optical element of the array of micro optical elements focuses a portion of the collimated illumination beam onto a tight focus (e.g., a small spot) [e.g., such that the array of micro optical elements forms an array of tight foci in the focal plane (e.g., for exciting fluorescence in the sample)], directing the back-emitted light from the sample to a detector (e.g., a CCD or CMOS camera) via detecting optics, wherein the detecting optics comprise: the optical chip, wherein the array of micro optical elements collects the back-emitted light that propagates (e.g., as individual collimated beams) and is directed (e.g., by a set of optics) toward the beam splitter, and an imaging lens for collimating the back-emitted light such that the back-emitted light is collimated by the imaging lens after passing through the beam splitter, and detecting, by the detector, the back-emitted light filtered by the aperture stop, wherein the detector comprises an array of detector elements, each detector element independently detecting a portion of the back-emitted light originating from a micro optical element in the array of micro optical elements; moving, by a scanning stage (e.g., comprising a support, a controller, and an actuator), a position of the optical chip relative to the transparent imaging window and the detector (e.g., wherein the position of the transparent window relative to the detector is fixed) to a next position of the plurality of positions of the scan pattern; and constructing, by a processor of a computing device, an image of the sample (e.g., representing an optical slice of the fresh tissue sample) based on the back-emitted light detected by the detector in each of the plurality of positions in the scan pattern.

In certain embodiments, the method comprises transmitting, by the processor, via a network, the image to a receiving device (e.g., a second computing device or a display) such that a pathologist in a remote location (e.g., outside of the operating theatre) can perform a pathology assessment.

In certain embodiments, the sample is stained with a fluorescent stain (e.g., proflavine, acridine orange, hematoxylin or eosin).

In certain embodiments, wherein imaging a portion of the sample [e.g., for in-operating-theatre imaging of tissue (e.g., fresh tissue) resected during surgery (e.g., cancer surgery)] is performed in less than 10 minutes (e.g., less than 5 minutes, less than 3 minutes or less than 2 minutes).

In certain embodiments, imaging a portion of the sample [e.g., for in-operating-theatre imaging of tissue (e.g., fresh tissue) resected during surgery (e.g., cancer surgery)] is performed in less than 2 minutes (e.g., less than 90 seconds or less than 1 minute). In certain embodiments, the portion of the sample has an area of at least 10 cm$^2$ (e.g., at least 12 cm$^2$, at least 15 cm$^2$, or at least 17 cm$^2$).

In certain embodiments, the sample has a volume having dimensions of no greater than 10 cm×10 cm×10 cm and the system is configured to image a full outer surface of the sample in an imaging time of no more than 45 minutes (e.g., no more than 30 minutes).

In certain embodiments, the method comprises, prior to providing the illumination beam for illuminating the sample: staining the sample with a fluorescent stain; and placing the sample in/on the sample dish.

In certain embodiments, the sample has a thickness that is within a range of 0.5 mm-10 cm (e.g., that is within a range of 3 mm-5 mm, 5 mm-10 mm, 7 mm-15 mm, 10 mm-25 mm, 15 mm-30 mm, or 25 mm-10 cm, and/or that is no less than 0.5 mm, no less than 1 mm, no less than 3 mm, or no less than 5 mm).

In certain embodiments, the method is performed using the system of any of the embodiments described herein.

In certain embodiments, the method comprises analyzing the image of the sample (e.g., automatically, semi-automatically, or manually) for identification of disease (e.g., cancer) for purposes of tissue removal and/or preservation in a surgical procedure (e.g., for intraoperative margin assessment in breast conserving surgery).

In certain embodiments, limitations described with respect to one aspect of the invention may be applied with respect to another aspect of the invention (e.g., features of various embodiments of the systems described herein may be applied in various embodiments of the methods described herein, and features of various embodiments of the methods described herein may be applied in various embodiments of the systems described herein).

In another aspect, the present invention is directed to a microscopy system for imaging of samples (e.g., in-operating theater confocal imaging of samples), comprising: an exposed (e.g., to air) transparent imaging window, the transparent imaging window providing a surface onto or over which a sample (e.g., a fluorescent-stained fresh sample) (e.g., an unsliced sample preserved for definitive assessment in follow-up testing) may be disposed in order to image the sample (e.g., wherein illumination light and back-emitted light pass through the imaging window); and a housing that at least partially encloses the microscopy system, wherein the housing comprises: an upper working surface, a window support base that is recessed below the upper working surface, and an imaging window support (e.g., comprising an opening) disposed on the window support base, wherein the imaging window is disposed on [e.g., attached (e.g., glued or sealed) onto] the imaging window support (e.g., over the opening).

In certain embodiments, the imaging window is centered in the imaging window support. In certain embodiments, the window support comprises an opening and the transparent imaging window is larger in area than the opening.

In certain embodiments, the sample (e.g., and a sample dish on which the sample is disposed) is accessible (e.g., laterally) to a user during imaging (e.g., without removal of a cover).

In certain embodiments, the upper working surface and the imaging window support base are formed from a continuous piece of material (e.g., metal or plastic).

In certain embodiments, the window support comprises a tapered edge (e.g., and has a circular cross-section). In certain embodiments, the tapered edges tapers outward from the transparent imaging window (e.g., is shaped like a frustum with a hollow channel). In certain embodiments, the tapered edge comprises polished metal. In certain embodiments, the polished metal is polished aluminum. In certain embodiments, the tapered edge has a surface roughness ($R_a$) of no more than 5 micrometers, no more than 3 micrometers, no more than 2 micrometers, or no more than 1 micrometer. In certain embodiments, the surface roughness ($R_a$) is no more than 1 micrometer.

In certain embodiments, the window support is attached to the imaging window, and the window support and the imaging window are both sized and shaped to accommodate an optical interface of a sample dish (e.g., with the sample disposed on the optical interface) (e.g., during imaging). In certain embodiments, the imaging window support and/or the imaging window accommodate an optical interface of a sample dish when the sample dish is mounted on the microscopy system (e.g., during imaging).

In certain embodiments, the imaging window is recessed below the upper working surface. In certain embodiments, the imaging window is disposed at least partially above the imaging window support. In certain embodiments, the imaging window is disposed at least partially in a common plane with the upper working surface. In certain embodiments, the image In certain embodiments, a distance between the optical interface and the upper working surface is no more than 5 mm (e.g., no more than 4 mm, no more than 3 mm, no more than 2 mm or no more than 1 mm).

In certain embodiments, a tool may rest simultaneously on the optical interface and the upper working surface in a substantially flat orientation.

In another aspect, the present invention is directed to a system for imaging multiple surfaces of a tissue specimen (e.g., comprising cancer, such as breast cancer). The system comprises: an imaging system [e.g., a fluorescent microscopy device (e.g., comprising a light source, a sample area, a plurality of focusing elements, and/or a plurality of detector elements] to obtain sample information from the tissue specimen; a processor; and a memory having instructions stored thereon. The instructions, when executed by the processor, cause the processor to: display a first graphical user interface (e.g., a specimen location GUI); receive one or more first user inputs (e.g., via the specimen location GUI), wherein the first user input comprises graphical or data field information including location data associated with the location of the tissue specimen when the tissue specimen was within a body or anatomical structure; receive one or more second user inputs (e.g., via an activation widget) wherein the one or more second user inputs comprises instructions to activate the imaging system; receive, from the imaging system, sample information; generate, from the sample information, image data (e.g., fluorescent image data); display, on a second graphical user interface (e.g., an image GUI), the image data [e.g., as a color image (e.g., a false color image)]; display a third graphical user interface (e.g., a specimen surface orientation GUI); receive one or more subsequent user inputs (e.g., via the specimen surface orientation GUI) wherein the one or more subsequent user input comprises graphical or data field information including orientation data associated with the orientation of the tissue specimen (e.g., in relation to standard anatomical planes); associate (e.g., tag) the image data with the location data and the orientation data; and store, in one or more databases, the image data, the location data, and the orientation data [e.g., wherein the image data is stored in a first database and associated with the location data and the orientation data stored in a second database (e.g., wherein the first database is the second database)].

In another aspect, the present invention is directed to a system for imaging multiple surfaces of a tissue specimen (e.g., comprising cancer, such as breast cancer). The system comprises: a processor; and a memory having instructions stored thereon. The instructions, when executed by the processor, cause the processor to: display a first graphical user interface (e.g., a specimen location GUI); receive one or more first user inputs (e.g., via the specimen location GUI), wherein the first user input comprises graphical or data field information including location data associated with the location of the tissue specimen when the tissue specimen was within a body or anatomical structure; receive one or more second user inputs (e.g., via an activation widget) wherein the one or more second user inputs comprises instructions to activate an imaging system to produce an image; receive, from the imaging system, sample information; generate, from the sample information, image data (e.g., fluorescent image data); display, on a second graphical user interface (e.g., an image GUI), the image data [e.g., as a color image (e.g., a false color image)]; display a third graphical user interface (e.g., a specimen surface orientation GUI); receive one or more subsequent user inputs (e.g., via the specimen surface orientation GUI) wherein the one or more subsequent user input comprises graphical or data field information including orientation data associated with orientation of the tissue specimen (e.g., in relation to standard anatomical planes); associate (e.g., tag) the image data with the location data and the orientation data; and store, in one or more databases, the image data, the location data, and the orientation data [e.g., wherein the image data is stored in a first database and associated with the location data and the orientation data stored in a second database (e.g., wherein the first database is the second database)].

In certain embodiments, the instructions, when executed by the processor, cause the processor to generate the image data, wherein the image data is converted to a false color image (e.g., wherein the image data is displayed on a purple/pink color scale, e.g., mimicking a hematoxylin and eosin stained optical microscopy image).

In certain embodiments, the specimen location GUI comprises graphical representations of an anatomical structure [e.g., one or both female (or male) breasts].

In certain embodiments, the specimen surface orientation GUI includes one or more graphical representations of locations relative to one or more anatomical planes (e.g., cranial and/or caudal directions in a vertical axis and/or frontal, dorsal, lateral, and/or medial directions in a horizontal (transverse) plane) to indicate the orientation of the tissue specimen [e.g., wherein the one or more graphical representations of locations comprise representations of complex orientations (e.g., comprising one or more of a cranial and caudal component and/or comprising one or more of a frontal, medial, dorsal, and lateral component)].

In certain embodiments, the instructions, when executed by the processor, cause the processor to: display an annotation GUI; and receive, via the annotation GUI, one or more subsequent user inputs, wherein the subsequent user input comprises graphical or data field information including graphical or textual annotations to a displayed image. Based on the received user input the annotations are associated with the image, stored in the database and, according to the user input through the annotation GUI, can be shown or hidden on the image display. In certain embodiments, the subsequent user input comprises graphical or data field information including graphical information delineating a region of interest. The delineations may define external borders of a region of interest, they may also define one or several internal cavities within a region of interest. In certain embodiments, the subsequent user input comprises graphical or data field information allowing to change previously entered graphical or textual annotations to a displayed image, including modifications to a delineated region of interest (for example, a change to the position of external borders of a delineated region, or a change to the borders of an internal cavity of such a region).

In certain embodiments, the instructions, when executed by the processor, cause the processor to: receive, via the image GUI, one or more subsequent user inputs, wherein the subsequent user input comprises information to select and to zoom/magnify a region of an image generated from the image data to create a region of interest; transform the image data (e.g., automatically, e.g., without user interaction) of the region of interest to adjust contrast and/or brightness; and display, on the image GUI, the adjusted image data of the region of interest.

In another aspect, the present invention is directed to a method for imaging a specimen. The method comprises: (i) marking a specimen that has been resected from a tissue (e.g., in a body or anatomical structure, e.g., in a subject, e.g., a patient) (e.g., using one or more surgical sutures) (e.g., to indicate an orientation of the specimen) (e.g., with respect to the body or anatomical structure); (ii) preparing the specimen for imaging (e.g., staining the specimen with an agent, e.g., a contrast agent); (iii) mounting the specimen on an imaging system (e.g., a fluorescence scanner) in a first position; (iv) launching one or more graphical user interfaces (GUIs) on a computing device associated with the imaging system (e.g., to control the imaging system and/or receive image data from the imaging system; (v) indicating, via a specimen location GUI, a location of the specimen [e.g., a location of the specimen within the tissue (e.g., with respect to the body or anatomical structure)] to generate specimen location information; (vi) imaging (e.g., using a fluorescence scanner) the specimen using the imaging system to generate an image; (vii) indicating, via a specimen surface orientation GUI, an orientation of the specimen [e.g., an orientation of the specimen within the tissue (e.g., with respect to the body or anatomical structure)] to generate specimen orientation information; (viii) tagging the image with the specimen location information and the specimen orientation information [e.g., wherein step (v), step (vii), and step (viii) are performed in any order (e.g., with respect to any other steps)]; (ix) mounting the specimen on the imaging system (e.g., a fluorescence scanner) in a second position; and (x) performing steps (iv)-(viii) on the specimen in the second position.

In certain embodiments, imaging comprises converting the image and/or displaying the image as a false color image (e.g., wherein the image data is displayed on a purple/pink color scale, e.g., mimicking a hematoxylin and eosin stained optical microscopy image).

In certain embodiments, indicating a location of the specimen, e.g., location of the specimen within the tissue (e.g., with respect to the body or anatomical structure) comprises indicating a location on a graphical representations of an anatomical structure (e.g., one or both female (or male) breasts).

In certain embodiments, indicating an orientation of the specimen comprises indicating an orientation on one or more graphical representations of locations relative to one or more anatomical planes (e.g., cranial, caudal, frontal, dorsal, lateral, and/or medial planes).

In certain embodiments, the method comprises annotating the image with graphical and/or textual annotations. In certain embodiments, annotating the image comprises delineating a region of interest. Delineating a region of interest (e.g., area of interest) may comprise defining external borders of a region of interest. Delineating may also comprise defining one or several internal cavities within a region of interest. In certain embodiments, the subsequent user input comprises graphical or data field information allowing to change previously entered graphical or textual annotations to a displayed image, including modifications to a delineated region of interest (for example, a change to the position of external borders of a delineated region, or a change to the borders of an internal cavity of such a region). Based on received user input, annotations may be associated with a displayed image, stored in a database and, for example according to user input through an annotation GUI, can be shown or hidden on the image display.

In certain embodiments, the method comprises: selecting, zooming/magnifying a region of the image to create a region of interest; transforming (e.g., automatically, e.g., without user interaction) the region of interest of the image to adjust contrast and/or brightness; and displaying the adjusted region of interest of the image.

In another aspect, the present invention is directed to a method for imaging multiple surfaces of a tissue specimen (e.g., comprising cancer, such as breast cancer). The method comprises: displaying, by a processor of a computing device, a first graphical user interface (e.g., a specimen location GUI); receiving, by the processor of the computing device, one or more first user inputs (e.g., via the specimen location GUI), wherein the first user input comprises graphical or data field information including location data associated with the location of the tissue specimen when the tissue specimen was within a body or anatomical structure; receiving, by the processor of the computing device, one or more second user inputs (e.g., via an activation widget) wherein the one or more second user inputs comprises instructions to activate an imaging system to produce an image; receiving, by the processor of the computing device, from the imaging system, sample information; generating, by the processor of the computing device, from the sample information, image data (e.g., fluorescent image data); displaying, by the processor of the computing device, on a second graphical user interface (e.g., an image GUI), the image data [e.g., as a color image (e.g., a false color image)]; displaying, by the processor of the computing device, a third graphical user interface (e.g., a specimen surface orientation GUI); receiving, by the processor of the computing device, one or more subsequent user inputs (e.g., via the specimen surface orientation GUI) wherein the one or more subsequent user input comprises graphical or data field information including orientation data associated with orientation of the tissue specimen (e.g., in relation to standard anatomical planes); associating (e.g., tagging), by the processor of the computing device, the image data with the location data and the orientation data; and storing, by the processor of the computing device, in one or more databases, the image data, the location data, and the orientation data [e.g., wherein the image data is stored in a first database and associated with the location data and the orientation data stored in a second database (e.g., wherein the first database is the second database)].

In certain embodiments, the method comprises generating, by the processor of the computing device, the image data, wherein the image data is converted to a false color image (e.g., wherein the image data is displayed on a purple/pink color scale, e.g., mimicking a hematoxylin and eosin stained optical microscopy image).

In certain embodiments, the specimen location GUI comprises graphical representations of an anatomical structure (e.g., one or both female (or male) breasts).

In certain embodiments, the specimen surface orientation GUI includes one or more graphical representations of locations relative to one or more anatomical planes (e.g., cranial and/or caudal directions in a vertical axis and/or frontal, dorsal, lateral, and/or medial directions in a horizontal (transverse) plane) to indicate the orientation of the tissue specimen [e.g., wherein the one or more graphical representations of locations comprise representations of complex orientations (e.g., comprising one or more of a cranial and caudal component and/or comprising one or more of a frontal, medial, dorsal, and lateral component)].

In certain embodiments, the method comprises: displaying, by the processor of the computing device, an annotation GUI; and receiving, by the processor of the computing device, via the annotation GUI, one or more subsequent user inputs, wherein the subsequent user input comprises graphical or data field information including graphical or textual annotations to a displayed image. In certain embodiments, based on the received user input the annotations are associated with the image, stored in the database and, according to the user input through the annotation GUI, can be shown or hidden on the image display.

In certain embodiments, the subsequent user input comprises graphical or data field information including graphical information delineating a region of interest. Delineating may comprise defining external borders of a region of interest. Delineating may also comprise defining one or several internal cavities within a region of interest. In certain embodiments, the subsequent user input comprises graphical or data field information allowing to change previously entered graphical or textual annotations to a displayed image, including modifications to a delineated region of interest (for example, a change to the position of external borders of a delineated region, or a change to the borders of an internal cavity of such a region).

In certain embodiments, the method comprises: receiving, by the processor of the computing device, via the image GUI, one or more subsequent user inputs, wherein the subsequent user input comprises information to select and to zoom/magnify a region of an image generated from the image data to create a region of interest; transforming, by the processor of the computing device, the image data (e.g., automatically, e.g., without user interaction) of the region of interest to adjust contrast and/or brightness; and displaying, by the processor of the computing device, on the image GUI, the adjusted image data of the region of interest.

Definitions

In order for the present disclosure to be more readily understood, certain terms used herein are defined below. Additional definitions for the following terms and other terms may be set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Image: As used herein, the term "image", for example, as in a two- or three-dimensional image of resected tissue (or other sample), includes any visual representation, such as a photo, a video frame, streaming video, as well as any electronic, digital, or mathematical analogue of a photo, video frame, or streaming video. Any system or apparatus described herein, in certain embodiments, includes a display for displaying an image or any other result produced by a processor. Any method described herein, in certain embodiments, includes a step of displaying an image or any other result produced by the method. Any system or apparatus described herein, in certain embodiments, outputs an image to a remote receiving device [e.g., a cloud server, a remote monitor, or a hospital information system (e.g., a picture archiving and communication system (PACS))] or to an external storage device that can be connected to the system or to the apparatus. In some embodiments, an image is produced using a fluorescence imaging system, a luminescence imaging system, and/or a reflectance imaging system. In some embodiments, an image is a two-dimensional (2D) image. In some embodiments, an image is a three-dimensional (3D) image. In some embodiments, an image is a reconstructed image. In some embodiments, an image is a confocal image. An image (e.g., a 3D image) may be a single image or a set of images.

3D, three-dimensional: As used herein, "3D" or "three-dimensional" with reference to an "image" means conveying information about three spatial dimensions. A 3D image may be rendered as a dataset in three dimensions and/or may be displayed as a set of two-dimensional representations, or as a three-dimensional representation. In certain embodiments, a 3D image is represented as voxel (e.g., volumetric pixel) data.

In certain embodiments, a system or apparatus outputs 3D images comprising voxels or otherwise has its output converted to 3D images comprising voxels for analysis. In certain embodiments, a voxel corresponds to a unique coordinate in a 3D image (e.g., a 3D array). In certain embodiments, each voxel exists in either a filled or an unfilled state (e.g., binary ON or OFF).

Mask: As used herein, a "mask" is a graphical pattern that identifies a 2D or 3D region and is used to control the elimination or retention of portions of an image or other graphical pattern. In certain embodiments, a mask is represented as a binary 2D or 3D image, wherein each pixel of a 2D image or each voxel of a 3D image is assigned one of two values of a binary set of values (e.g. each pixel or voxel may be assigned a 1 or a 0, e.g. each pixel or voxel may be assigned a Boolean "true" or "false" value). In some embodiments, a mask is applied to a camera frame during reconstruction.

User: As used herein, a user is any person who uses an imaging system disclosed herein. A user may be, for example, but not limited to, a surgeon, a surgical staff (e.g., a nurse or medical practitioner in an operating room), a lab technician, a scientist, or a pathologist. It is understood that when an action is described as being performed by a surgeon, in some embodiments, a user who is not a surgeon performs an equivalent function.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Drawings are presented herein for illustration purposes, not for limitation. The foregoing and other objects, aspects, features, and advantages of the invention will become more apparent and may be better understood by referring to the following description taken in conjunction with the accompanying drawings, in which:

FIG. 5A and FIG. 5B are plan views representing an illustrative rectangular optical chip comprising an array of micro lenses disposed in a square lattice, according to illustrative embodiments of the invention;

FIG. 8C is a schematic of a cross section of the mounting surface shown in FIG. 8A;

FIG. 17 is screenshot showing an illustrative specimen location interface for breast conservation surgery, according to illustrative embodiments of the invention;

FIG. 20 is a block diagram of an example network environment for use in the methods and systems described herein, according to illustrative embodiments of the invention; and FIG. 21 is a block diagram of an example computing device and an example mobile computing device, for use in illustrative embodiments of the invention.

DETAILED DESCRIPTION OF CERTAIN EMBODIMENTS

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim. Headers are provided for the convenience of the reader and are not intended to be limiting with respect to the claimed subject matter.

Figure 1:
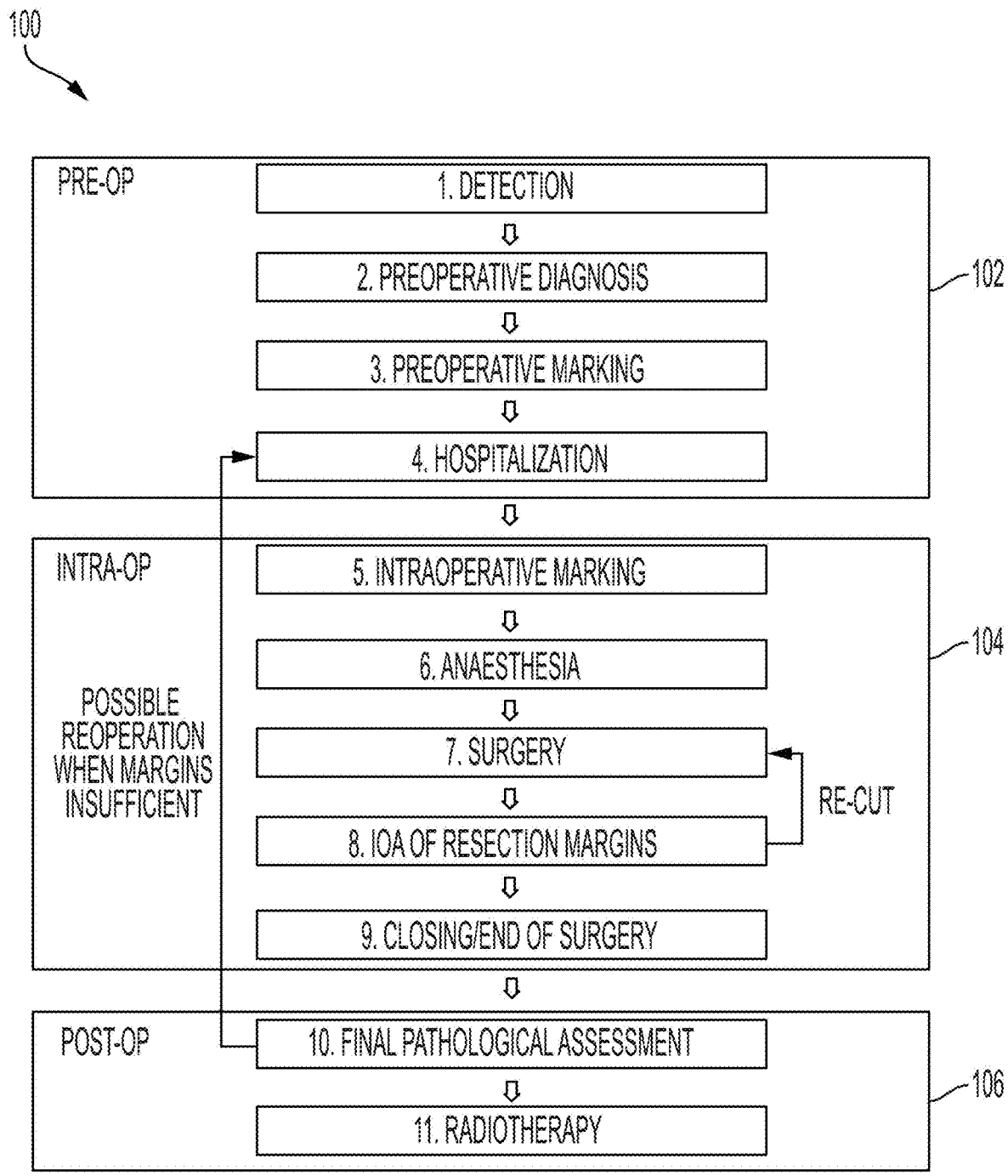
FIG. 1 is an illustrative surgical workflow in which a system in accordance with the present disclosure can be used, according to illustrative embodiments of the invention.

In some embodiments, an imaging system is used in a surgical procedure during intraoperative assessment of a resected tissue sample. Referring now to FIG. 1, an illustrative surgical procedure 100 includes a pre-operative sub-procedure 102, an intra-operative sub-procedure 104, and a post-operative sub-procedure 106. In certain embodiments, an imaging system is used to make an intraoperative assessment of a resected tissue sample in order to determine whether the tissue sample has sufficient margins. In certain embodiments, a re-cut (e.g., cavity shaving) is made when margins are determined to be insufficient using images produced by an imaging system during intraoperative assessment. In some embodiments, a second operation is performed (e.g., a reoperation) after a final pathological assessment is performed. By providing fast and high-resolution imaging of resected fresh tissue samples, an imaging system can reduce the rate of reoperation for a given disease. For example, lumpectomies currently result in reoperation in approximately 30% of cases, which could be reduced if pathological quality imaging occurs during surgery.

In some embodiments, systems and methods disclosed herein are used to image a surface of a tissue sample (e.g., resected during surgery). In some embodiments, a sample is freely accessible (e.g., exposed to a user) such that a full mapping of the tissue sample surface may be achieved. For example, in some embodiments, an entire surface of a sample can be imaged in a period of time (e.g., less than 30 minutes or less than 20 minutes) with no dead zones. In contrast, typical frozen section analysis may image less than 10% of a sample surface (e.g., less than 5% of a sample surface) in an equivalent time or an even longer period of time (e.g., because only a few micrometer scale slices are taken from approximately every centimeter of a sample).

In some embodiments, samples to be imaged are relatively large (e.g., having dimensions up to 10 cm×10 cm×10 cm). For example, typical breast cancer tissue samples (lumps) can be as large as 8 cm and thus have an area to image (full surface) up to 400 cm$^2$ (e.g., approximately equivalent to an 8 cm×8 cm×8 cm volume). In some embodiments, an imaging system can image up to 18 cm$^2$ (e.g., up to 10 cm$^2$, up to 12 cm$^2$, or up to 15 cm$^2$) in a period of time of no more than 3 minutes (e.g., no more than 2 minutes, no more than 90 seconds, or no more than one minute). Accordingly, in some embodiments, no more than 50 images (e.g., no more than 40 images or no more than 30 images) and thus less than 60 minutes (e.g., less than 40 minutes or less than 30 minutes) are needed to image the entire surface of a large sample. In certain embodiments, a full sample surface is imaged during an intraoperative assessment.

Imaging Systems

An imaging system can be a fluorescence, luminescence, reflectance or other optical imaging modality system. In certain embodiments, an imaging system comprises a transparent imaging window, an optical module, and, optionally, a computing device. In certain embodiments, an optical module comprises a beam splitter, a photon source, a detector, an optical chip, and may comprise other illumination and detecting optics that guide an illumination beam from a photon source to sample and back-emitted lighted emitted from the sample to a detector. An optical module may comprise one or more of a focusing lens, a collimating lens, an imaging lens, one or more apertures, one or more filters. A transparent imaging window provides a surface for mounting a sample during imaging (e.g., with a sample dish disposed therebetween). A detector comprising an array of detector elements detects back-emitted light from a sample in order to form an image of the sample. A detector may be, for example, a CCD or CMOS camera. In some embodiments, a detector is a CMOS camera. An imaging system may comprise a scanning stage for moving a portion of an imaging system along a scan pattern during imaging in order to form an image of a sample. A scanning stage may be attached to an optical chip, a portion of an imaging system comprising an optical chip (e.g., an optical subsystem), or a transparent imaging window.

Figure 2:
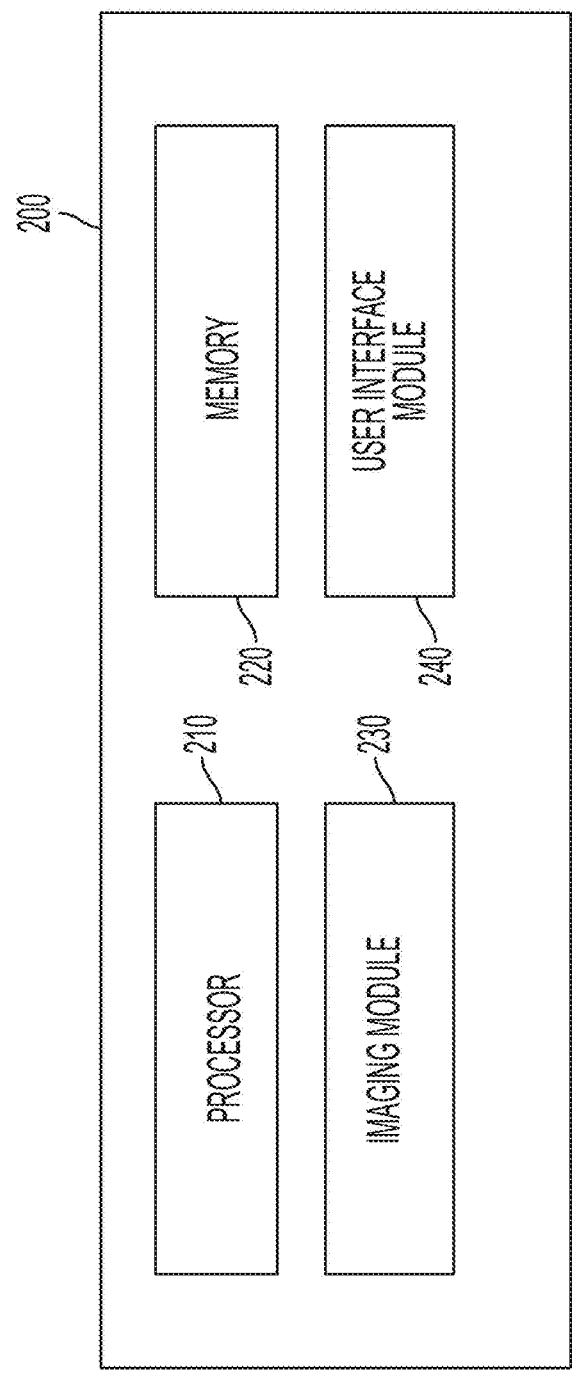
FIG. 2 is a system diagram showing various components in an illustrative system for imaging tissue specimen, according to illustrative embodiments of the invention.

FIG. 2 is a system diagram showing various components in an illustrative system 200 for imaging tissue specimen, according to illustrative embodiments of the invention. In certain embodiments, the imaging system includes a processor 210, a memory 220, an imaging module 230, and a user interface module 240. Specimen and sample are used interchangeably herein. A specimen may be a biological sample (e.g., tissue, such as resected fresh tissue). Non-biological specimens are also contemplated.

The processor 210 can process instructions for execution within the computing device 200, including instructions stored in the memory 220 to display graphical information for a GUI on an external input/output device, such as the user interface module 240. In other implementations, multiple processors may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where one or more functions are described as being performed by "a processor", this encompasses embodiments wherein the one or more functions are performed by any number of processors (e.g., one or more processors) of any number of computing devices (e.g., one or more computing devices) (e.g., in a distributed computing system).

The memory 220 stores information within the imaging system 200. In some implementations, the memory 220 is a volatile memory unit or units. In some implementations, the memory 220 is a non-volatile memory unit or units. The memory 220 may also be another form of computer-readable medium, such as a magnetic or optical disk.

The imaging module 230 captures images of the tissue specimen which is subject to analysis. In certain embodiments, the imaging module 230 includes an optical module, an optical chip, a scanning stage, and a transparent imaging window, as described further herein and in the subsections below.

The user interface module 240 can have a display device [e.g., a CRT (cathode ray tube) or LCD (liquid crystal display) monitor] for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input (e.g., using a touch screen).

Optical Modules

An optical module of an imaging system provides an illumination beam for illuminating a sample and optics for detection of back-emitted light from a sample. In some embodiments, in order to facilitate fast imaging of samples, an optical module comprises an optical chip comprising an array of micro optical elements that each individually image a portion of a sample. An illumination beam may interact with (e.g., pass through) optics before illuminating a sample. Illumination optics may include one or more of a focusing lens, a first aperture, a beam splitter, a collimating lens and an optical chip. For example, an illumination beam may be emitted from a photon source and then pass through a focusing lens and a first aperture before reflecting off of a beam splitter and then subsequently be collimated by a collimating lens and pass through an optical chip onto a sample. A sample may emit or reflect "back-emitted light" in response to illumination by an illumination beam. Such light may then be directed toward a detector by detection optics. For example, back-emitted light may pass back through an optical chip and a beam splitter before passing through a second aperture, an imaging lens, an emission filter and subsequently being incident on a detector. In this way, a beam splitter filters out an illumination beam and back-emitted light in order to form an image from back-emitted light incident on a detector.

Various optics may be used to guide an illumination beam through an array of micro optical elements and back-emitted light onto a detector. Certain illustrative arrangements and characteristics of optical components that may exist in an optical module are described herein in the subsequent paragraphs. Specifically, certain illustrative spatial arrangements of optics are described and illustrated, but it is understood that such description is not an exhaustive description of all possible arrangements.

A photon source can be a laser or other monochromatic light source. In some embodiments, a photon source is a single channel (i.e., single-wavelength) source (e.g., a laser that emits light between about 450 and about 490 nm in wavelength). In some embodiments, a photon source is a 488 nm laser. In some embodiments, a photon source is a multi-channel (i.e., multi-wavelength) source. In some embodiments, a photon source is a laser and, optionally, the laser emits at least one of (i) a Gaussian beam and (ii) a beam with a half-power beam width of less than 1.5 mm in diameter. In some embodiments, a photon source emits a wavelength of between 450 nm and 500 nm (e.g., between 480 nm and 490 nm or about 488 nm). In some embodiments, a photon source is a laser that has a power of at least 5 mW (e.g., at least 20 mW, at least 50 mW, at least 80 mW, at least 100 mW, at least 150 mW, or at least 200 mW). In some embodiments, a photon source is a laser that has a power of less than 400 mW (e.g., less than 300 mW, less than 200 mW, less than 150 mW, less than 100 mW, less than 80 mW, less than 50 mW, less than 20 mW, less than 5 mW, or less than 1 mW).

In some embodiments, a system is arranged and constructed such that the system is a Class 1 laser product according to an American National Standards Institute (ANSI) standard and/or an International Electrotechnical Commission (IEC) standard for laser safety (e.g., according to ANSI Z136.1, IEC 825, or IEC 60825). For example, a system may comprise a laser, a transparent imaging window, and optics (e.g., illumination and/or detection optics) with the laser and optics at least partially contained within a housing such that any laser light transmitted through the transparent imaging window does not produce exposure (e.g., to a user, such as a surgeon) exceeding a limit for a Class 1 laser product as defined by an ANSI standard and/or IEC standard. For example, a system may have an open-top architecture (e.g., as shown in FIG. 8A-8C, 10A-10B, or 11A-11B, e.g., the system may or may not use an optical chip) that exposes a user to some light from an illumination beam, but not to such an extent that the amount (e.g., flux) of light exceeds a limit for a Class 1 laser product as defined by an ANSI standard and/or IEC standard. For example, a user may safely access a sample being imaged and/or to be imaged by a system that is a Class 1 laser product (e.g., in order to reposition and/or change the sample). In some embodiments, a photon source itself is a Class 1 laser product. In some embodiments, a photon source itself produces radiation in excess of a limit for a Class 1 laser product, but laser light transmitted through a transparent imaging window does not produce exposure (e.g., to a user, such as a surgeon) exceeding a limit for a Class 1 laser product as defined by an ANSI standard and/or IEC standard. A system that is a Class 1 laser product may be safer to operate, require less training prior to use, and/or be more easily (e.g., quickly) deployed in a new environment (e.g., because of, for example, less rigorous certification requirements are).

In certain embodiments, a photon source has a reduced temporal coherence. For example, a photon source can be a light-emitting diode (LED) or super luminescent diode (SLED) instead of a laser. Reduced temporal coherence can reduce imaging artifacts (e.g., interference patterns) between a sample dish and a transparent imaging window caused by index mismatch at one or more interfaces, with or without also using an imaging artifact reducing fluid therebetween. A photon source with reduced temporal coherence can still have high spatial coherence. In certain embodiments, a photon source with a reduced temporal coherence is used in combination with an anti-reflection coating on a transparent imaging window, a mounting surface of a sample dish, or both.

In some embodiments, an imaging system comprises a focusing lens disposed in an optical path of an illumination beam provided by a photon source. A focusing lens may have a focal length of between 1 mm and 2 mm (e.g., between 1.3 mm and 1.7 mm, between 1.4 mm and 1.5 mm, or about 1.45 mm). A focusing lens may have a lens diameter of between 2 mm and 3 mm (e.g., between 2.2 mm and 2.8 mm or about 2.4 mm). An imaging system may comprise a first aperture disposed in an optical path of an illumination beam between a focusing lens and a beam splitter (e.g., such that the focusing lens lies between a photon source and the first aperture along the optical path). In some embodiments, a first aperture has a diameter of between 0.5 mm and 1.5 mm (e.g., about 1.0 mm).

A beam splitter may be a dichroic mirror or dichroic filter, a prism, or a grating. In certain embodiments, a beam splitter is a dichroic mirror. In some embodiments, a dichroic mirror has a reflection band that is in a range of between 400 nm and 600 nm (e.g., between 450 nm and 500 nm) and a transmission band that is in a range between 450 nm and 1000 nm (e.g., between 500 nm and 850 nm). In some embodiments, a dichroic mirror has an area of at least 100 mm² and/or no more than 1200 mm² (e.g., about 900 mm²).

In some embodiments, an imaging system comprises a collimating lens in an optical path of an illumination beam between a beam splitter and an optical chip. Light between a collimating lens and an optical chip is collimated. In some embodiments, a collimating lens has a clear aperture larger than an imaging system field of view. For example, a collimating lens having a circular clear aperture of at least 60 mm in diameter may be used with an imaging system having a field of view of 48 mm×36 mm. In some embodiments, a collimating lens is a cemented doublet lens (e.g., a cemented achromatic doublet lens). In some embodiments, a collimating lens has a focal length of at least 100 mm (e.g., at least 150 mm or at least 200 nm). In some embodiments, a collimating lens has a diameter of at least 50 mm (e.g., at least 60 mm, at least 70 mm or at least 75 mm). In some embodiments, a collimating lens has a diameter of about 75 mm.

A focusing lens and collimating lens form a beam expander for an illumination beam provided by a photon source. Focal lengths of a focusing and a collimating lens may be chosen according to photon source diameter and desired illumination uniformity. It is desirable that illumination intensity remains more or less constant on an optical chip over an illumination profile (e.g., the entire field of view of an imaging system). For example, in some embodiments, for a laser having a Gaussian beam of 1 mm FWHM, focal length of a collimating lens should be about 60× larger than that of a focusing lens to provide an illumination profile with less than 50% drop over an illumination profile (e.g., field of view) of 48 mm×36 mm (60 mm diagonal).

An optical chip comprises an array of micro-optical elements. For example, the array may be an array of micro lenses (e.g., refractive lenses), Fresnel zone plates, microreflective objects (e.g., lenses), gradient-index (GRIN) lenses, or a combination thereof. An array of micro-optical elements comprises a plurality of micro-optical elements. For example, in some embodiments, an array of micro optical elements comprises from 1000 to 100,000 micro optical elements (e.g., from 20,000 to 60,000 micro optical elements or from 50,000 to 70,000 micro optical elements). In some embodiments, an array of micro optical elements consists of about 30,000 micro optical elements or about 60,000 micro optical elements.

A field of view of an imaging system may be based on a size of an optical chip and/or detector. In some embodiments, an optical chip is slightly larger than a field of view of an imaging system so that the optical chip can be mounted without obstructing the target field of view. For example, a 54.5×37.0 mm chip size may be required to produce a 48 mm×36 mm field of view. Resolution and overall sensor size of a detector may determine, at least in part, characteristics of an optical chip (e.g., a number of micro optical elements in an array or pitch of the array). Each micro optical element may correspond to more than a detector element (e.g., pixel) in a detector. For example, in some embodiments, each micro optical element in an array of micro optical elements in an optical chip corresponds to an area of at least 2×2 detector elements, an area of at least 3×3 detector elements, an area of at least 4×4 detector elements, an area of at least 5×5 detector elements, or more. In some embodiments, an array of micro optical elements is a rectangular array and each micro optical element in the array corresponds to a non-square array of detector elements in the detector. A field of view formed by an optical chip (e.g., including range of motion of the optical chip or a transparent window that moves over the optical chip) may be at least 10×10 mm, at least 20×20 mm, at least 30×30 mm, at least 40×30 mm, at least 50×30 mm, at least 45×35 mm or larger.

A detector may be a high-resolution camera, for example, having a high resolution. A high resolution camera, such as a CCD or CMOS camera, may have a resolution of 320×240 or better (e.g., 640×480 or better). Moreover, to facilitate fast imaging, a detector may have a high frame rate. For example, in some embodiments, a detector has a frame rate of at least 200 fps, at least 300 fps, at least 400 fps, or at least 500 fps. For example, a detector may be a high resolution camera (e.g., CMOS camera) that has a 640×480 resolution and a 500 fps frame rate. In some embodiments, a detector comprises more detector elements than the number of micro optical elements in an array of micro optical elements in an optical chip. For example, an area between 2×2 pixels and 5×5 pixels in size receives back-emitted lighted from a single micro optical element during a scan. In some embodiments, a ratio of micro optical elements in the array of micro optical elements to detector elements in the array of detector elements is from 1:1 to 1:100, 1:1 to 1:10, 1:5 to 1:12, 1:5 to 1:80, 1:20 to 1:70, 1:30 to 1:60, or 1:40 to 1:50 (e.g., about 1:1, 1:2, 1:3, 1:4, 1:6, 1:8, 1:9 or 1:12, e.g., to the nearest whole number, or within a range of any two of these values).

In some embodiments, an imaging system comprises an imaging lens for collimating back-emitted light from a sample. In some embodiments, the back-emitted light is collimated by the imaging lens after passing through a beam splitter. In some embodiments, an imaging lens is a cemented doublet lens (e.g., a cemented achromatic doublet lens). In some embodiments, an imaging lens has a focal length of between 10 mm and 30 mm (e.g., between 15 mm and 25 mm, between 18 mm and 22 mm, or about 19 mm). In some embodiments, an imaging lens has a lens diameter of between 6 mm and 15 mm (e.g., between 10 mm and 13 mm or about 12.7 mm).

In some embodiments, a second aperture is disposed in an optical path of back-emitted light between a beam splitter and a detector. The second aperture may further be disposed in the optical path of the back-emitted light between the imaging lens and the beam splitter. In some embodiments, a second aperture has a diameter of between 1 mm and 5 mm (e.g., between 2 mm and 4 mm). In some embodiments, a second aperture has a diameter of about 3 mm.

In some embodiments, a dichroic mirror is positioned between a collimating lens and a second aperture along an optical path of back-emitted light (e.g., where the beam is not collimated). The closer a dichroic mirror is to a second aperture, the smaller the dichroic mirror can be in size without vignetting and, thus, the less expensive it is to produce. Similarly, the larger the focal length of a collimating lens, the smaller the dichroic mirror can be in size without vignetting and, thus, the less expensive it is to produce. For example, for an imaging system field of view of 48 mm×36 mm built with a dichroic mirror of 36 mm×25 mm (e.g., corresponding to a standard size in fluorescence microscopy), a collimating lens with a focal length of 200 mm ensures there is no vignetting on the dichroic mirror.

An imaging system may comprise a filter to filter out (e.g., eliminate or decrease) undesired light, thereby preventing that undesired light from being incident on a detector. In some embodiments, a filter (e.g., an emission filter) is disposed in an infinity space and is disposed between an imaging lens and the detector (e.g., in an optical path of back-emitted light). In such embodiments, a filter can be significantly smaller and less expensive than if positioned together with a beam splitter between a collimating lens and an optical chip. Having an emission filter between a second aperture and a detector can also simplify alignment of an imaging system, for the reflection of laser light on the optical chip can remain visible in the plane of the second aperture. In some embodiments, an opaque enclosure between the detector and the emission filter makes the device even more robust to stray light. In some embodiments, an additional opaque enclosure between an emission filter and a second aperture further makes the device even more robust to stray light. In some embodiments, a filter is a long-pass filter (e.g., having a cut-off wavelength of at least 400 nm, at least 450 nm, at least 500 nm, or at least 600 nm).

In some embodiments, a focal length ratio of a collimating lens to an imaging lens is selected so that the magnification makes possible to image the light collected by an optical chip on a detector. For example, in some embodiments, for an imaging system with a 48 mm×36 mm field of view built with a 4.8 mm×3.6 mm detector, a focal length of a collimating lens should be at least 10× larger than that of a focusing lens. Larger focal lengths for a collimating lens and imaging lens are generally desirable in order to limit the Petzval curvature.

In some embodiments, an optical chip, a collimating lens, a second aperture, an imaging lens and a detector are in a 4f optical configuration: with the optical chip in the focal plane of the collimating lens, the second aperture in the common focal plane of the collimating lens and the imaging lens and with the detector in the focal plane on the other side of the imaging lens. In some embodiments, an optical chip is located between a collimating lens focal plane and a collimating lens itself. In some embodiments, this makes the overall device more compact. In some embodiments, the distance between a second aperture and an imaging lens can be smaller than the imaging lens focal length with the distance between the imaging lens and a detector adjusted accordingly.

Figure 3A:
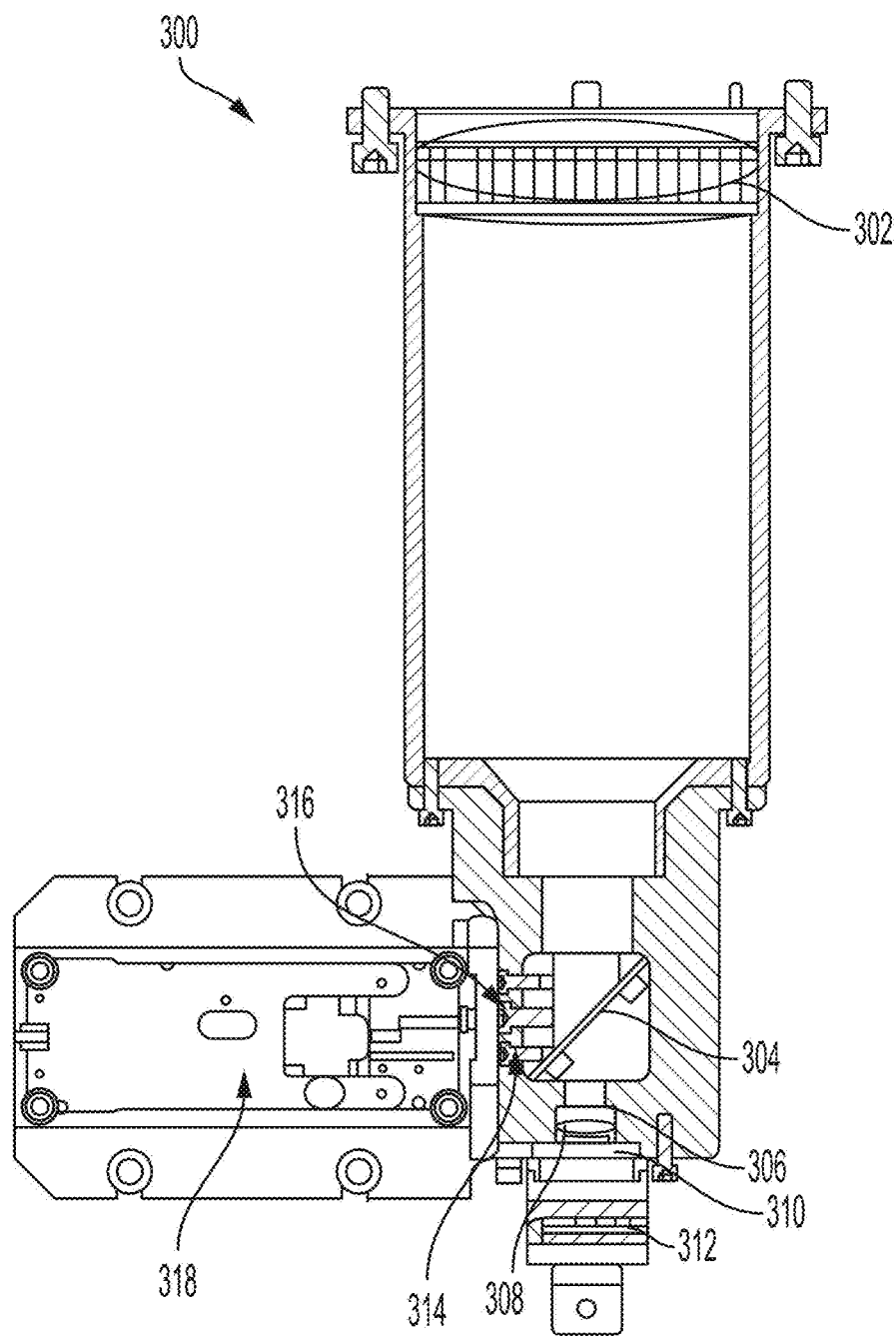
FIG. 3A is a schematic cross section of an illustrative optical module used in an imaging system, according to illustrative embodiments of the invention.
Figure 3B:
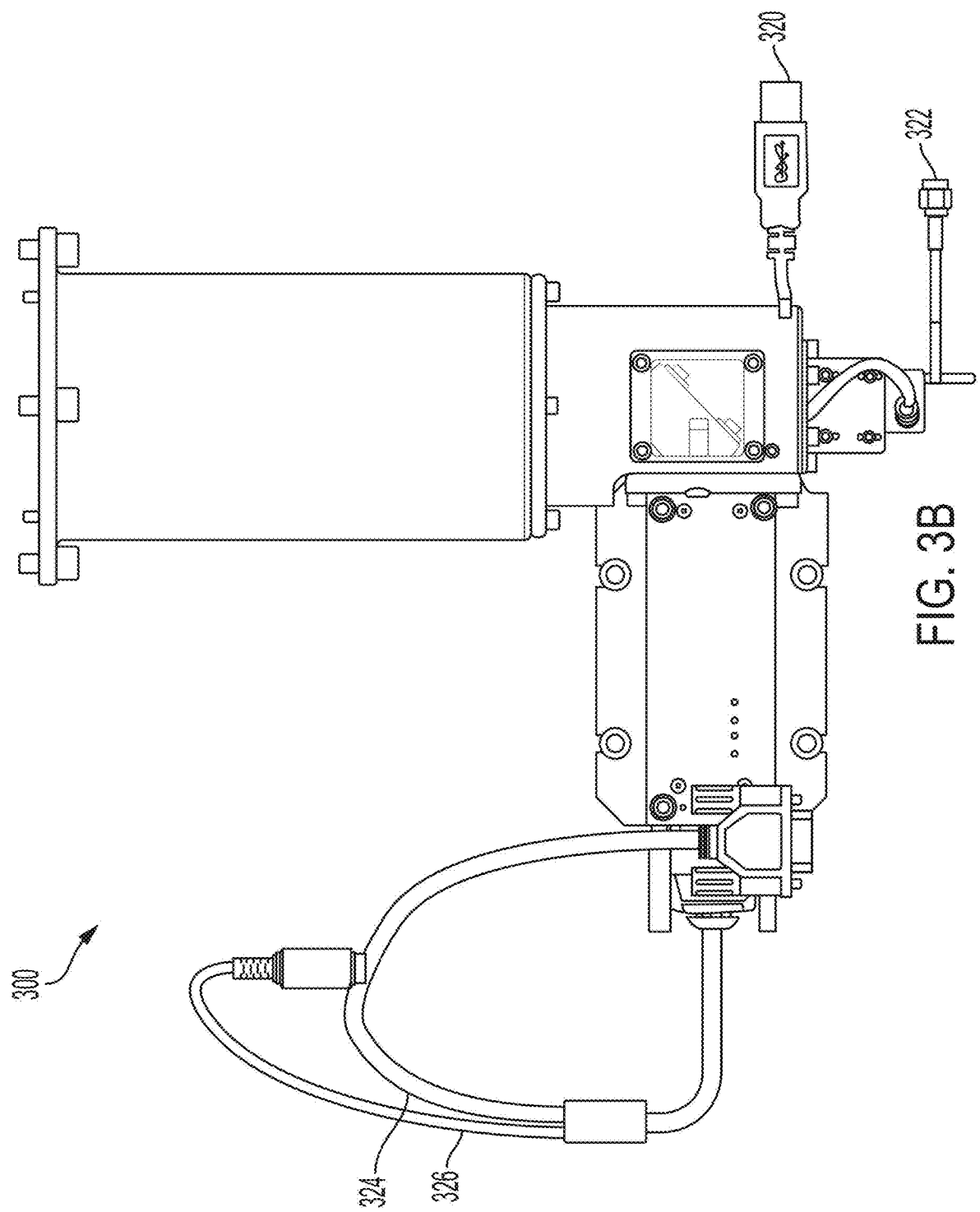
FIG. 3B is a second view of the illustrative optical module shown in FIG. 3A that shows input and output connections to components of the illustrative optical module.
Figure 3C:
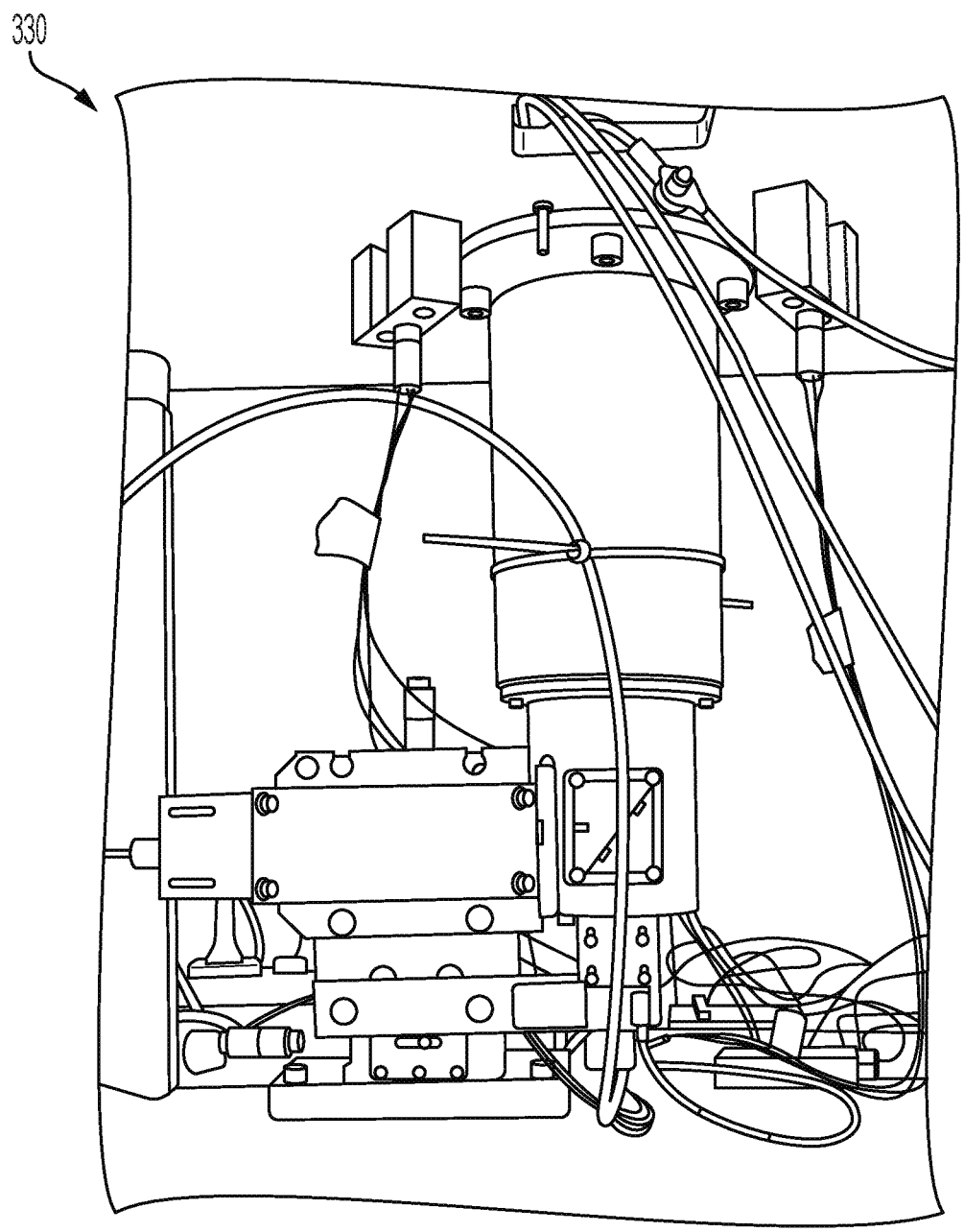
FIG. 3C is a view of an illustrative optical module comprising illumination and detecting optics that is mounted to an imaging system, according to illustrative embodiments of the invention.

Referring now to FIG. 3A and FIG. 3B, an illustrative optical module 300 comprising illumination and detecting optics is shown. The illustrative optical module 300 comprises a photon source 318 (in this case a laser), a focusing lens 316, a first aperture 314, a beam splitter 304 (in this case a dichroic mirror), a collimating lens 302, a second aperture 306, an imaging lens 308, a filter (e.g., an emission filter) 310, a detector 312 (in this case a CMOS camera). Not shown in FIG. 3A is an optical chip that is disposed above the collimating lens 302. FIG. 3B shows connections to the optical module 300 that are used during imaging. For example, the laser and detector may be connected to a computing device of the imaging system comprising the optical module 300. Optical module 300 comprises signal input 324 for control of photon source 318 by a computer (e.g., a DB9 connector for serial control) and power input 326, detector frame output 320, and connector 322 (in this case a coaxial output) for connecting a controller of a scanning stage to detector 312 to sync frame acquisition to positions along a scan pattern. In some embodiments, a detector frame output is a Universal Serial Bus (USB) output, wherein USB is used in order to support sufficient bandwidth for a high-frame rate detector (e.g., a 500 frames per second (fps) detector). FIG. 3C is a view 330 of an illustrative optical module comprising illumination and detecting optics that is mounted to an imaging system.

Optical Chips

An optical chip comprises an array of micro optical elements. An array of micro optical elements may be disposed on a surface of an optical chip. For example, the micro optical elements may be disposed on a surface of a substrate of an optical chip. In some embodiments, an optical chip comprises an array of micro optical elements attached to a holder around the periphery of the array (e.g., is not disposed on a substrate). Generally, the outer perimeter of an optical chip can have any shape. In some embodiments, an optical chip is a rectangle (e.g., a square or a non-square). For example, in some embodiments, an array is integral with a substrate of an optical chip. An array of micro optical elements can be non-integral, but attached to a substrate of an optical chip. An array of micro optical elements may comprise at least 25,000 micro lenses (e.g., with a radius of curvature (ROC) of between 200 μm and 300 μm). In some embodiments, micro lenses have a conic constant of between −1.8 and −2.2 or between about −2 and about −2.05. An absorptive and/or reflective layer may be provided on an optical chip between micro optical elements in an array (e.g., to act as an aperture). An optical chip may be made of fused silica. Micro optical elements may be arranged in a regular array on an optical chip (e.g., a square lattice). In some embodiments, an array of micro optical elements has a pitch of between 200 μm and 300 μm. In some embodiments, an optical chip has a non-regular array, for example, having a different pitch in an x-direction and a y-direction. In some embodiments, an optical chip has a high numerical aperture for high resolution imaging and more efficient background rejection.

In some embodiments, the surface of an optical chip between and/or around micro optical elements of a micro optical element array are coated with an absorptive and/or reflective layer. The absorptive and/or reflective layer may be, for example, a chromium layer, an aluminum layer, or a dielectric mirror layer. In some embodiments, an absorptive and/or reflective layer fully covers inter-lens area of an optical chip on the surface on which an array of micro optical elements is disposed. A material in an absorptive and/or reflective layer may have an optical density of no less than 1, no less than 2, or no less than 3. In some embodiments, a chromium layer that has an optical density of no less than 3 is coated on inter-lens area of an optical chip. In some embodiments, an absorptive and/or reflective layer acts as an aperture for each micro optical element and a diameter (e.g., a lens diameter) of each micro optical element is no smaller than a diameter of a corresponding aperture defined by the absorptive and/or reflective layer.

In some embodiments, an optical chip has a thickness of less than 2.0 mm (e.g., less than 1.5 mm or about 1.5 mm). In some embodiments, an array of micro optical elements has an area of at least 30 mm×20 mm (e.g., at least 40 mm×30 mm or at least 50 mm×35 mm) (e.g., of about 54.5 mm×37 mm). In some embodiments, an array of micro optical elements has a pitch of between 100 μm and 400 μm (e.g., between 200 μm and 300 μm or about 250 μm) (e.g., wherein a variation in pitch between micro optical elements of the micro optical element array is no more than 6 no more than 4 or no more than 2 μm). In some embodiments, an array of micro optical elements is a regular array and a pitch of micro optical elements in the array in a first direction equals a pitch of micro optical elements in the array in a second direction that is perpendicular to the first direction. For example, micro optical elements may be arranged in a square lattice. In some embodiments, a parallelism of each set of opposing edges of the array of micro optical elements is better than about ±0.250 mrad (e.g., no more than or about ±0.125 mrad). In some embodiments, a parallelism of an array of micro optical elements relative to edges of an optical chip is better than about ±0.250 mrad (e.g., no more than or about ±0.125 mrad). Without wishing to be bound by any particular theory, generally, increased parallelism of edges of an optical chip as well as of an array of micro optical elements to edges of an optical chip can improve resulting image quality.

In some embodiments, each micro optical element of an array of micro optical elements has at least one convex surface. For example, each micro optical element may be a planoconvex lens or a biconvex lens. A convex surface of each micro optical element may have a shape obtained by the revolution of a conic section (e.g., with a radius of curvature of between 200 µm and 300 µm). In some embodiments, a convex surface of each micro optical element has a conic constant from −1.8 to −2.2 (e.g., about −2 or about −2.05 or between about −2 and about −2.05).

In some embodiments, each micro optical element in an array of micro optical elements focuses light onto an area (spot) smaller than a pitch (e.g., the pitch) of the array. Accordingly, during imaging, a scan pattern along which either a sample or an optical chip is moved can be chosen to fill the unit cell area of the array. As such, a smaller pitch can reduce the range of motion made during a scan. In some embodiments, each micro optical element of an array has a spot size from 0.2 µm to 5 µm. For example, the spot size may be 0.2 µm to 2 µm, 0.8 µm to 3 µm, or 1 µm to 2 µm. In some embodiments, a focal length of each micro optical element in an array of micro optical elements is between 100 µm and 700 µm. For example, between 200 µm and 600 µm or 500 µm to 600 µm. In some embodiments, a focal length of each micro optical element in an array is about 550 µm. In some embodiments, micro optical elements in an array of micro optical elements collectively focus onto a common focal plane. For example, each element of an micro optical element array may focus onto a single point on the common focal plane.

A smaller pitch of an array of micro optical elements can result in faster image acquisition (e.g., for a given scan step). For a given numerical aperture, a small pitch means a short micro optical element focal length and therefore a short distance between an optical chip and its image plane. An imaging window of an imaging system needs to fit between an optical chip and a focal plane (e.g., imaging plane) of an optical chip. In some embodiments, an optical interface of a sample dish additionally needs to fit between an optical chip and a focal plane of the optical chip. Therefore, a pitch of an array micro optical elements may be chosen to balance image acquisition speed and focal length of the array. For example, in some embodiments, an optical chip with an array of micro optical elements having a 200-300 micrometer pitch and a focal length of 500 to 600 micrometers makes for reasonably fast imaging while leaving enough space for a thick imaging window (e.g., that does not appreciably deflect) and, optionally, a disposable optical interface.

Figure 4:
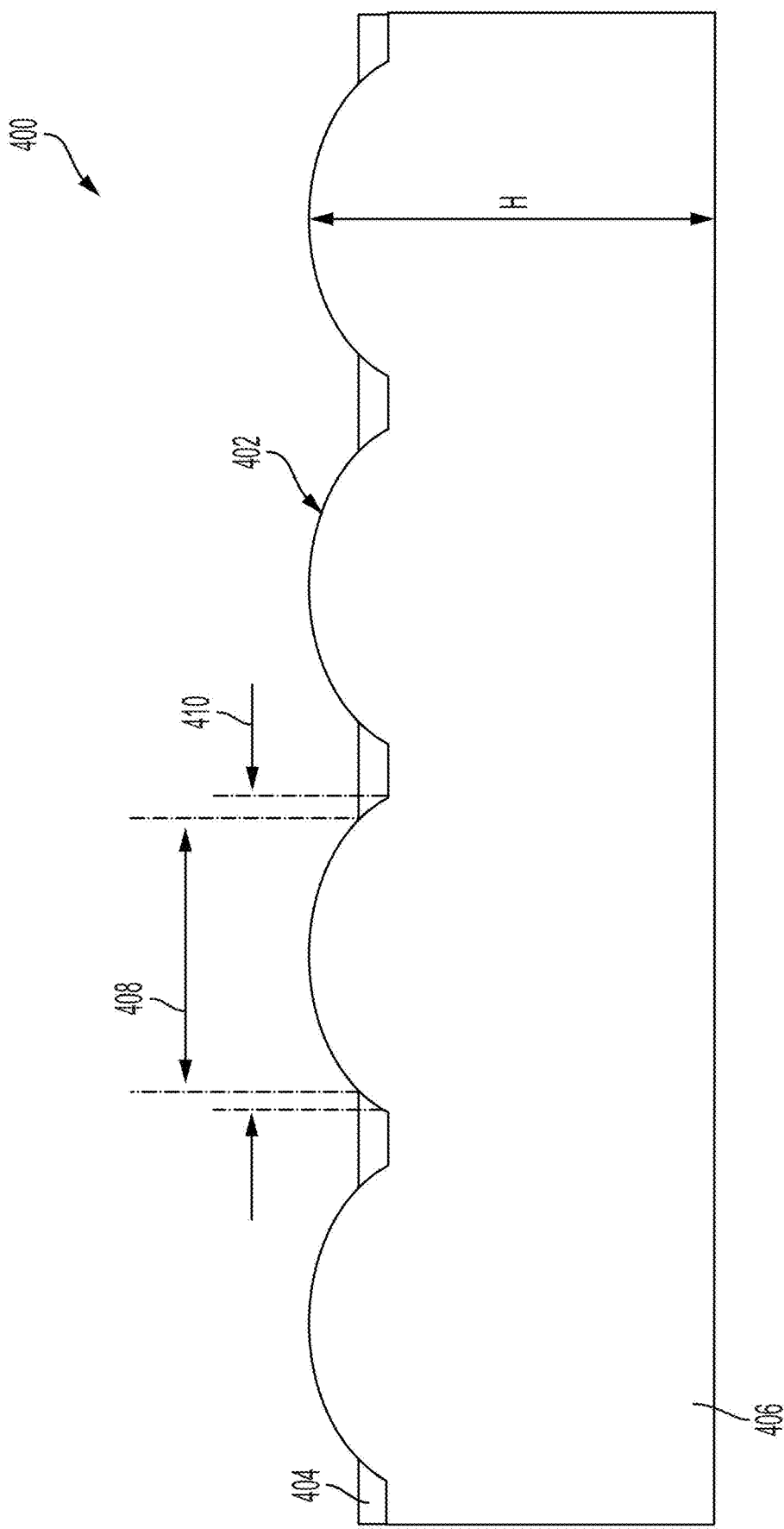
FIG. 4 is a schematic of a portion of an illustrative optical chip, according to illustrative embodiments of the invention.

FIG. 4 shows a diagram of a cross section of a portion of an illustrative optical chip 400. Optical chip 400 comprises a substrate 406 and an array of micro optical elements. Each micro optical element 402 is a convex microlens. The convex microlenses 402 are integral with the substrate 406 such that the substrate 406 and microlenses 402 are together one continuous material. For example, they may be formed simultaneously during fabrication. The thickness (H) of optical chip 400 can be taken as the distance between the top of the micro optical elements and the opposite surface of the substrate, as shown. Thickness of an optical chip may be less than 2.0 mm (e.g., less than 1.5 mm or about 1.5 mm). An optical chip may have a total thickness variation and/or total flatness deviation of less than 20 µm (e.g., less than 15 µm, less than 10 µm, or less than 5 µm). Optical chip 400 is coated with a reflective layer 404 of chromium. Reflective layer 404 is disposed in inter-lens area between micro optical elements 402. It is understood that a reflective layer disposed in an inter-lens area may extend partially onto one or more lenses near the periphery of the lens(es) as shown in FIG. 5A and FIG. 5B. If a reflective layer 404 extends partially over micro optical elements near peripheries of the micro optical elements, a micro optical element diameter 410 is larger than a reflective layer aperture 408 formed by reflective layer 404.

FIG. 5A and FIG. 5B schematically illustrate two views of illustrative optical chip 600 that comprises an array of micro optical elements 502. FIG. 5A shows a plan view of the entirety of optical chip 500 (individual micro optical elements and optional reflective/absorptive layer are not shown in FIG. 5A). Optical chip 500 has a rectangular cross section having dimensions W and L (i.e., with W≠L). In some embodiments, W=L. Optical chip 500 has high parallelism with edges of optical chip 500 having a parallelism of better than about ±0.250 mrad (e.g., no more than or about ±0.125 mrad). FIG. 5B shows a portion of optical chip 500 including a portion of array of micro optical elements 502. An array of micro optical elements disposed on a surface of optical chip 500 may comprise at least 1,000 micro optical elements, at least 5,000 micro optical elements, at least 10,000 micro optical elements, at least 20,000 micro optical elements, at least 30,000 micro optical elements, at least 50,000 micro optical elements, at least 60,000 micro optical elements, or at least 100,000 micro optical elements. Array of micro optical elements 502 is highly parallel relative to edges of optical chip 500. Array 502 has a parallelism relative to edges of an optical chip of better than about ±0.250 mrad (e.g., no more than or about ±0.125 mrad). Array 502 is a regular array. In some embodiments, an array of micro optical elements is non-regular.

Scanning Stages

In certain embodiments, an imaging system comprises a scanning stage used in scanning along a scan pattern in order to form an image. In certain embodiments, a scanning stage comprises a stage support, an actuator, and a controller. A support may be attached to an optical chip or a transparent imaging window. An actuator actuates to move a stage support along a scan pattern. A scanning stage may be a piezo-actuated stage (i.e., comprising a piezoelectric actuator). An imaging system may optionally comprise a coarse translation stage that may be attached to an imaging window. For example, such a configuration can allow for mosaic images to be constructed for very large samples or may be used to assist in sample positioning over an optical chip for imaging.

In some embodiments, a scanning stage is a three-axis positioning stage (e.g., a high precision three-axis positioning stage). For example, wherein the x- and y-axes are used in scanning and the z-axis is used to appropriately focus a sample. In some embodiments, a scanning stage is a two-axis positioning stage (e.g., a high precision two-axis positioning stage). In some embodiments, a scanning stage has a precision of equal to or better than 5 µm (e.g., equal to or better than 3 µm, equal to or better than 2 µm, or equal to or better than 1 µm). In some embodiments, a scanning stage is configured to bring an imaging window in close proximity to an array of micro optical elements (e.g., within 100 µm). In some embodiments, a scanning stage is a computer actuated scanning stage (e.g., synchronized with the detector).

Conventional microscopy devices image a field of view that is limited in part by the microscope objective: the better the resolution, the smaller the field of view. To image tissue specimens that are larger than the field of view, devices generally rely on a translation stage to moves the specimen relative to the microscope and stitch together images at different locations on the sample to produce a stitched mosaic image of the specimen. In many cases, one of two approach is used for such translation. In the first approach, a sample is in motion and the system is thus subject to image artifacts (image blurring, specimen displacement or deformation, etc.). In the second approach, the full mass of the microscope is in motion, requiring powerful motion stages and limiting the speed and precision. In both approaches, there generally are external moving parts, which poses risks to users (e.g., in an operating theater setting).

In contrast, moving an optical chip relative to an imaging window and detector along a scan pattern can reduce the mass in motion during imaging. For example, in some embodiments, an optical chip weighs less than the other optics used in imaging as well as less than the combined weight of a sample, sample holder (e.g., sample dish), and imaging window such that scanning by moving the optical chip minimizes mass in motion during scanning (e.g., imaging). In contrast, conventional imaging systems typically use a translation stage to move a sample relative to the system (e.g., by moving the sample itself or moving the whole imaging system while the sample is fixed). This can lead to image artifacts (e.g., due to inertia from continuous movement of a large mass during imaging). In some embodiments, artifacts caused by motion (e.g., caused by inertia) (e.g., image blurring or sample displacement or deformation) are reduced or eliminated when a scanning stage scans an optical chip along a scan pattern. Moreover, In some embodiments, a scanning stage moves a sample (e.g., by moving an imaging window) relative to an optical chip and a detector.

Transparent Imaging Windows

A transparent imaging window physically separates a sample (e.g., disposed on a sample dish) from optics of the imaging system optics. An illumination beam propagates through a transparent imaging window to illuminate a sample and back-emitted light from the sample propagates through the transparent imaging window in the opposite direction and is then detected. An imaging window may be free standing over a surface that is at least as large as the field of view of any imaging system. For example, an imaging window may be at least as large as an area corresponding to a scan range of an optical chip attached to a scanning stage.

In some embodiments, a sample is disposed on a sample dish during imaging. The sample dish may be very well controlled (relative to a desired or standardized thickness) (e.g., both throughout the surface of an optical interface of the sample dish and from one optical interface to another in a set of sample dishes) such that an autofocus or focus adjustment routine is not necessary prior to imaging.

In some embodiments, an imaging window comprises a clear, transparent and non-scattering material (e.g., glass or sapphire) to allow high resolution imaging. A transparent imaging window is at least 50% transparent to at least one of an illumination beam provided by a photon source and back-emitted light from a sample (e.g., both). For example, a transparent imaging window may be at least 60% transparent, at least 70% transparent, at least 80% transparent, at least 90% transparent, or at least 95% transparent to at least one of an illumination beam provided by a photon source and back-emitted light from a sample (e.g., both). In some embodiments, an imaging window comprises (e.g., consists essentially of) a hard material to prevent it from being scratched by contact with foreign objects. In some embodiments, an imaging window comprises a material that is harder than stainless steel (e.g., sapphire), since many surgical and lab tools that could enter in contact with the imaging window are made of stainless steel. An imaging window may comprise an impact resistant material (e.g., sapphire) to prevent the imaging window from breaking in case of accidental impact with a foreign object. An imaging window comprises a clear aperture over which the imaging window is freestanding (e.g., is not mechanically supported) that is at least as large as a field of view of an imaging system. In some embodiments, a clear aperture of an imaging window is as large or larger than an area scanned by an optical chip (e.g., an any scanning stage support attached thereto) during imaging.

Large tissue samples can be relatively heavy (for example, a 8 cm×8 cm×5 cm tissue may weigh about 300 grams) and thus exert appreciable force on an imaging window. Any deflection due to sample weight can change a position of a sample relative to a focal plane of an optical chip. For a given load, a thicker a material will deflect less, and a material with a higher Young modulus will also deflect less. In certain embodiments, an imaging window is thick (e.g., no more than 900 µm, no more than 800 µm, no more than 600 µm, no more than 400 µm, or no more than 300 µm) (e.g., between 200 µm and 800 µm, between 400 µm and 600 µm, or about 500 µm) and comprises a material with a high Young's modulus (e.g., sapphire) in order to limit its deflection under the load exerted by a sample. In some embodiments, an imaging window has a Young's modulus of at least 100 GPa (e.g., at least 200 GPa or at least 300 GPa), such that the imaging window does not appreciably deflect when the sample is disposed thereon (or thereover).

In certain embodiments, a transparent imaging window comprises (e.g., is coated with) an anti-reflection coated (e.g., permanently) on a surface of the transparent imaging window such that during imaging the anti-reflection coating is disposed between the transparent imaging window and an optical interface of a sample dish (e.g., is in contact with an imaging artifact reducing fluid disposed between the dish and the window). The anti-reflection coating may be engineered to reduce reflections caused by an illumination beam that has a normal (perpendicular) incidence angle to the transparent imaging window. In this way, an anti-reflection coating can reduce imaging artifacts (e.g., interference patterns) that would otherwise arise during imaging from index mismatch at an interface with the transparent imaging window. A transparent imaging window comprising an anti-reflection coating may be used with or without an imaging artifact reducing fluid disposed between a sample dish and the window.

In some embodiments, a disposable protection (e.g., a sample dish) is placed and/or mounted onto an imaging area before a surgical procedure. For imaging, a sample is then directly placed onto an optical interface of the sample dish. In some embodiments, a sample is disposed directly on an imaging window during imaging.

In some embodiments, optics of an imaging system (e.g., an optical chip) are protected from the environment (e.g., dust, liquids, users, biohazardous materials), at least in part, by an imaging window, permanently fixed (e.g., glued) to an imaging window support of a housing that at least partially encloses the imaging system. In some embodiments, an imaging window is made of sapphire. In some embodiments, an imaging window is made of sapphire with a c-axis parallel to an optical axis of micro optical elements in an array of micro optical elements (e.g., of an optical chip) and accordingly does not exhibit birefringence effects and is highly transparent to a broad spectrum and thus suitable for high resolution microscopy imaging.

A transparent imaging window may at least partially confine optical elements of an imaging system. Since optical elements, such as an optical chip, can be very sensitive and be damaged or destroyed easily, confinement from contaminates, for example, is desirable. In some embodiments, at least a support and an actuator of a scanning stage and an optical chip are confined (e.g., fully confined) within a system such that at least the support and the actuator of the scanning stage and optical chip are protected from a sample (e.g., and the outside environment) at least in part by the imaging window when the sample is disposed on or over the imaging window.

In some embodiments, an imaging system comprises a housing that at least partially encloses the system and exposes the sample to ambient conditions (e.g., is uncovered) during imaging. In some embodiments, the housing comprises a window support upon which a sample dish containing the sample may be disposed and held on or over the imaging window during imaging (e.g., thereby providing unobstructed access to the sample), such that the sample and the sample dish are accessible to a user during imaging (e.g., without removal of a lid). In some embodiments, a window support is connected to an imaging window, and the window support and the imaging window are both sized and shaped to accommodate an optical interface of a sample dish (e.g., with the sample disposed on the optical interface) (e.g., during imaging). In some embodiments, an imaging window is recessed below an upper surface of a housing and the imaging window is attached (e.g., glued) to the window support such that the imaging window projects above the window support.

In some embodiments, a sample is not inserted in any cartridge, container or holder prior to being placed on or over an imaging window for imaging. In some embodiments, can be imaged as soon as it is placed on a sample dish and the sample dish mounted (e.g., placed) on an imaging system, thereby simplifying pre-imaging procedures and reducing time from obtaining a sample to producing an image (e.g., providing a faster more convenient workflow). An imaging system that has an exposed imaging window (e.g., used with an unenclosed sample dish) can provide fast and simple access to a sample (e.g., for repositioning).

Fresh tissue samples generally have a non-regular shape. So for a given face (or area) of a sample to be imaged, it is possible that a tissue sample does not hold upright by itself and needs external support to hold it in proper position for imaging. Since tissue samples greatly vary in shape, size and mechanical properties, it is unlikely that a single sample holder design allows to efficiently position a sample on any one of its faces. Accordingly, in some embodiments, a sample is not inserted in any cartridge, container or holder prior to being placed on an imaging system for imaging. In some embodiments, a large zone above and around the sample imaging area is kept unobstructed to manipulate the tissue sample and equipped with tool pads to position tools such as standard forceps to hold the tissue sample in place during the imaging process. In some embodiments, an image plane of an optical chip is always located at the same axial position with respect to where the sample is positioned. Without wishing to be bound to any particular theory, the combination of (i) an exposed imaging window, (ii) a large unobstructed zone above and around the sample, and/or (iii) the ability to hold the sample in place using tools can facilitate the efficient and effective manipulation of the sample (e.g., for more user-friendly imaging with improved results).

In certain embodiments, a sample remains motionless (e.g., is not intentionally moved) during imaging. For example, in a system having an open-top architecture (e.g., as shown in FIG. 6A, 8A-8C, 10A-10B, or 11A-11B) with an outer housing (e.g., with all optics contained therein), motion may be limited to parts that are contained within the outer housing. For example, a scanning stage and optical chip moved by the scanning stage during scanning may be contained within such an outer housing. A motionless sample can reduce the weight in motion during scanning. In certain embodiments, there are no moving parts around a transparent imaging window, thereby reducing or eliminating the likelihood of pinching or trapping of a user's hand in a system, contaminating the system by trapping loose matter (e.g., sample debris), or damaging the system by knocking or misaligning a moving part.

In some embodiments, a system has an open-top architecture (e.g., as shown in FIG. 6A-6B, 8A-8B, or 11A-11B and described elsewhere herein) but does not comprise an optical chip (e.g., comprises conventional optics, such as a single objective lens whose image plane is scanned by an illumination beam during imaging). That is, an open-top architecture may provide benefits, including, for example, easy sample manipulation and/or isolation of moving parts and/or sensitive optical elements, to a system that uses conventional optics (e.g., without an optical chip).

A sample disposed on a sample dish may be exposed to a user (e.g., a surgeon) when the sample dish is mounted onto an imaging system such that the user may easily manipulate the sample, for example, using a tool such as standard surgical forceps or a hand of the user. Accordingly, images can be generated using microscopy techniques with reduced setup times due to fast mounting and sample (re-)positioning. Therefore, imaging systems disclosed herein can reduce the amount of time required to perform microscopy imaging and thereby (i) increase the number of procedures in which microscopy is used as an intraoperative assessment technique and (ii) decrease the likelihood of patient complications due to prolonged medical imaging. In certain embodiments, an exposed working area around a sample allows a user (e.g., a surgeon) to use forceps to position and/or orient a sample and leave the forceps holding the sample in place during imaging in order to maintain a desired position and/or orientation of the sample. In certain embodiments, tissue flattening is desirable and an exposed working area allows a flattening tool to be used during imaging.

Figure 6A:
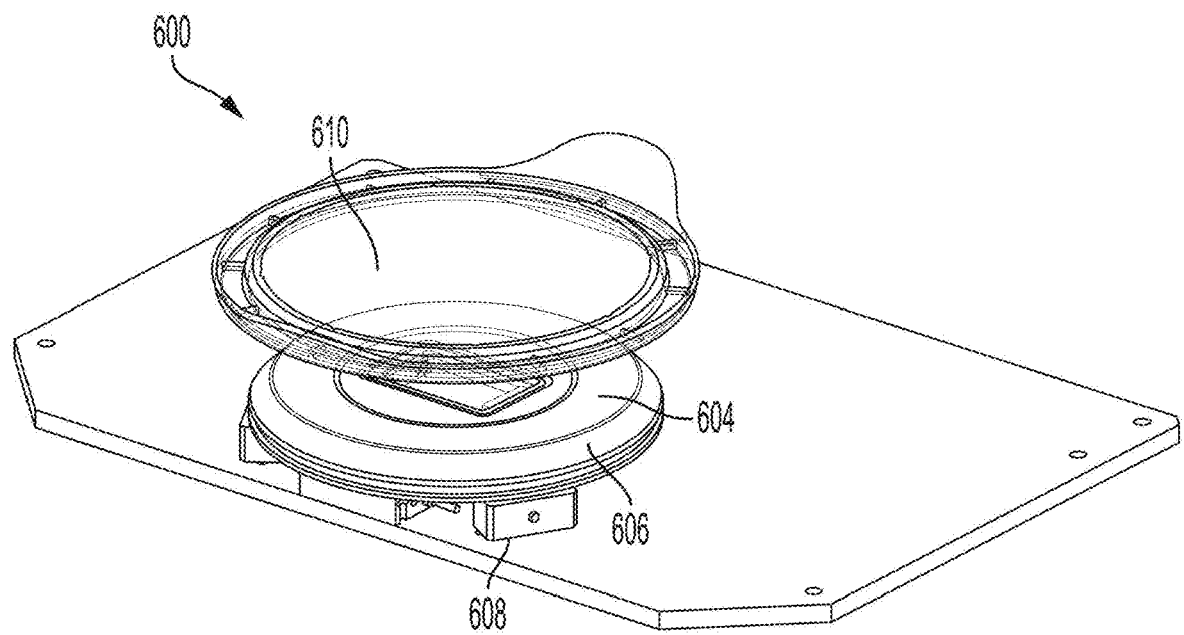
FIG. 6A shows an illustrative sample dish mounting surface of an imaging system comprising an imaging window, according to illustrative embodiments of the invention.
Figure 6B:
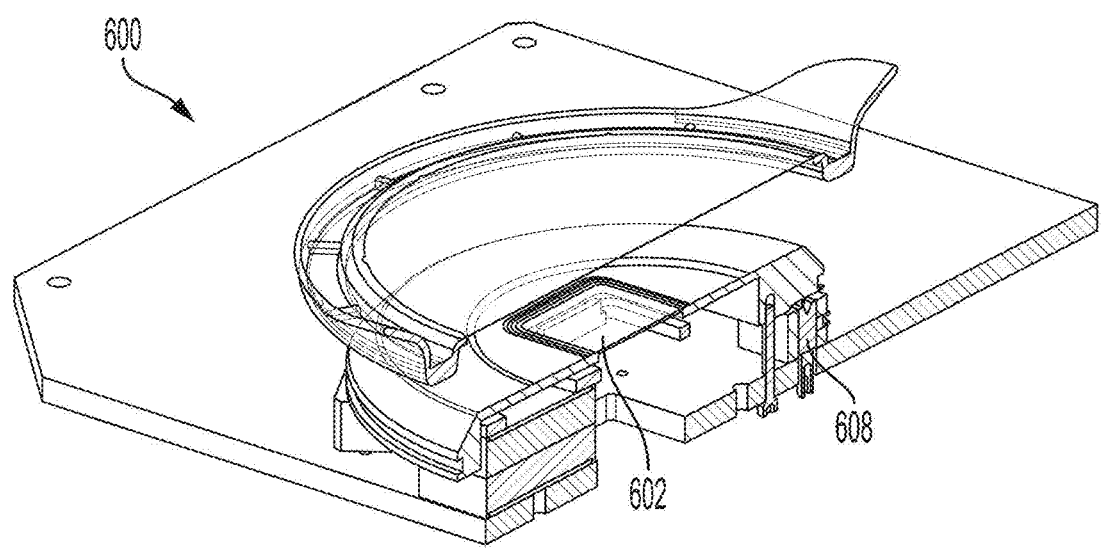
FIG. 6B shows a cut-away cross section of FIG. 6A.

FIGS. 6A and 6B show illustrative sample dish 610 being mounted onto illustrative imaging system 600. Imaging system 600 comprises transparent imaging window 602, which is attached to window support 604. As can be seen in FIG. 6B, a portion of transparent imaging window 602 is freestanding and provides an unobstructed optical path for an illumination beam and back-emitted light. A portion of transparent imaging window 602 that is not freestanding provides an interface for attaching (e.g., adhering) transparent imaging window 602 to window support 604. Imaging window 602 is centered in window support 604. Window support 604 has tapered edge 606. Tapered edge 606 may be made from polished metal (e.g., polished aluminum). Window support 604 is shaped like a frustum with a central hollow channel. Tapered edge 606 accommodates a ditch-shaped support member 608 of sample dish that may be used to retain fluids that are excreted from a sample. Sample dish 610 contacts window support 604 only at an optical interface of the sample dish when mounted on imaging system 600. In some embodiments, an optical interface and a support member (e.g., a ditch-shaped support member 608) of a sample dish contacts an imaging system [e.g., at a transparent imaging window and a window support (e.g., and one or more tapered edges of the window support)] when the sample dish is mounted on the imaging system.

In certain embodiments, an imaging system comprises a transparent imaging window and a window support that supports the transparent imaging window. The window support may comprise one or more tapered edges. One or more tapered edges may have an advantage, in certain embodiments, in that they allow a sample dish mounted thereon to be self-centering. One or more tapered edges may be tapered such that they taper outward (e.g., from a transparent imaging window). For example, a window support may be shaped like a frustum (e.g., a frustum with a hollow channel). An example of a tapered edge of a window support that tapers outward is shown in FIG. 6A and also FIG. 8A. (A sample dish is mounted on the window support in FIG. 8A, thereby partially obscuring the tapered edge.) In some embodiments, if a sample dish is self-centering to a centered position in that if it is placed slightly off-center (e.g., within 3 cm, within 2 cm, or within 1 cm of the centered position), the dish will slide into its natural centered position. A sample dish may be slightly tilted when initially placed off-center. For example, there may initially be a gap between an optical interface of a sample dish and a transparent imaging window that is eliminating when the dish self-centers. In some embodiments, a window support provides self-centering functionality for a sample dish with or without a sample pre-disposed thereon. For example, in some embodiments, a sample dish placed slightly off-center will self-center and then a sample is disposed on a sample surface of the dish (e.g., a sample surface of an optical interface).

Without wishing to be bound to any particular theory, a window support may be self-centering at least in part due to a low coefficient of friction between a sample dish and a window support that facilitates sliding. For example, in some embodiments, a window support, or at least one or more tapered edges thereof, comprises or is made from a metal, such as a polished metal. For example, a window support, or at least one or more tapered edges thereof, may comprise or be made from polished aluminum. In certain embodiments, a tapered edge of a window support has a surface roughness ($R_a$) of no more than 5 micrometers, no more than 3 micrometers, no more than 2 micrometers, or no more than 1 micrometer. In some embodiments, the surface roughness ($R_a$) is no more than 1 micrometer.

In some embodiments, a sample dish is sized and shaped to be self-centering. For example, a sample dish may comprise a support member (e.g., a ditch-shaped support member) with an inner lip and an outer lip, wherein the inner lip is closer to an optical interface of the sample dish than the outer lip (e.g., is closer to a tapered edge of a window support of an imaging system when the sample dish is mounted on the imaging system). The inner lip may be sloped outward away from the center of the sample dish (e.g., in order to align, at least partially, with a tapered edge of a window support). In some embodiments, an inner perimeter of a has a characteristic dimension (e.g., diameter) approximately equal in size and shape to an upper surface of a window support so that when a sample dish is mounted on an imaging system, the sample dish naturally fits snuggly over the window support in a centered position. In some embodiments, such a sizing and shaping of a sample dish assists in the sample dish self-centering to a centered position if initially placed slightly off-center (e.g., within 3 cm, within 2 cm, or within 1 cm of a centered position). In some embodiments, only an outer surface of an inner lip is sloped. A sloped support member (e.g., a sloped inner lip) may be sloped outward and, optionally, may have a constant slope.

A support member may be made from injection molded plastic. For example, a support member may be made from cyclo-olefin polymer (COP). In some embodiments, a support member or portion thereof (e.g., an outer surface of an inner lip) has a surface roughness (Ra) of no more than 6 micrometers, no more than 4 micrometers, no more than 3 micrometers, or no more than 2.5 micrometers. In some embodiments, the surface roughness (Ra) is no more than 3 micrometers. A low surface roughness can result from using a mold with low surface roughness when injection molding, for example. A low surface roughness of a sample dish (e.g., a support member) can help reduce a coefficient of friction between a sample dish and a window support, for example if a window support comprises a tapered edge made of polished metal.

In some embodiments, an imaging system comprises a kinematic support structure [e.g., comprising at least three feet (e.g., four) of adjustable height], the support structure supporting the imaging window (e.g., directly or indirectly by supporting the window support that the imaging window is attached to) such that the height and tilt of the imaging window relative to the optical chip are adjustable (e.g., wherein one or more feet of the kinematic support structure are adjustable). A kinematic support structure may be based on a Maxwell kinematic coupling or a Kelvin kinematic coupling. Referring again to FIGS. 6A and 6B, illustrative imaging system 600 comprises a kinematic support structure for adjusting height and tilt of an imaging window relative to an optical chip based on Maxwell kinematic coupling.

Figure 7A:
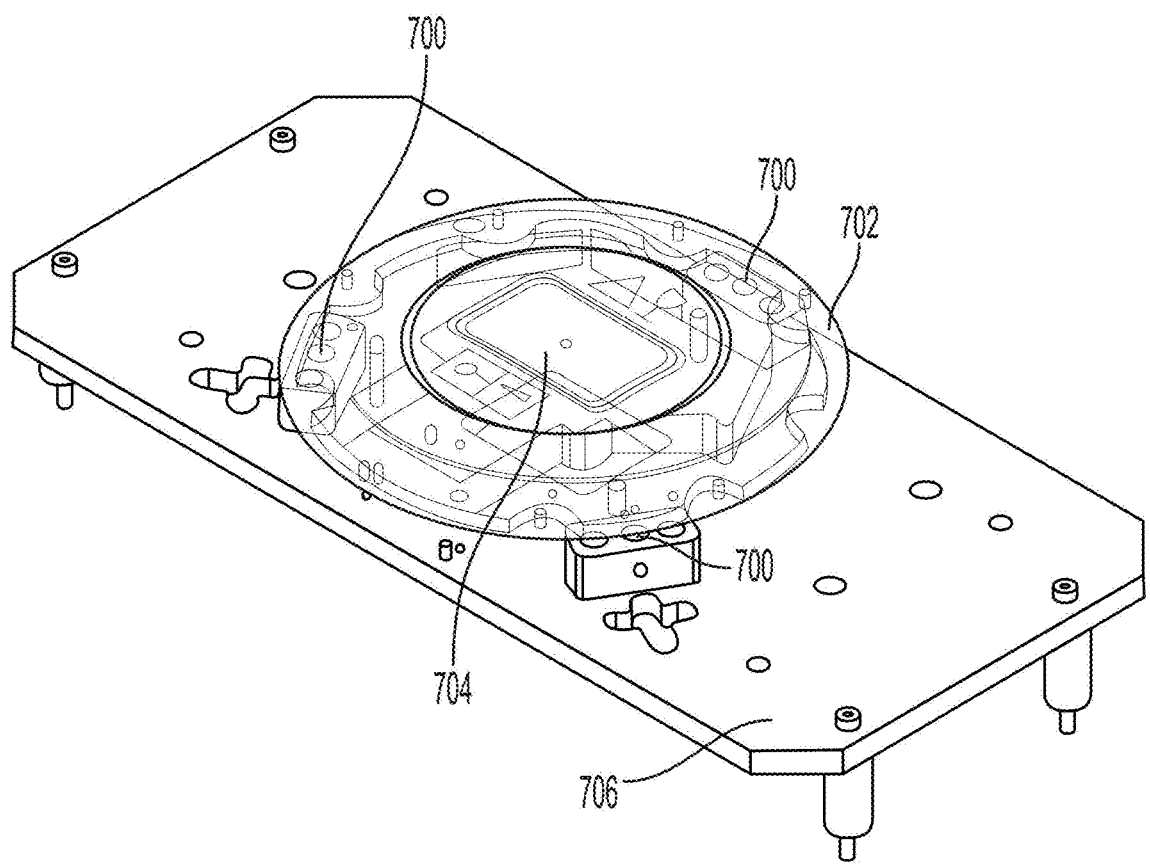
FIG. 7A shows an imaging window supported by a kinematic support structure, according to illustrative embodiments of the invention.
Figure 7B:
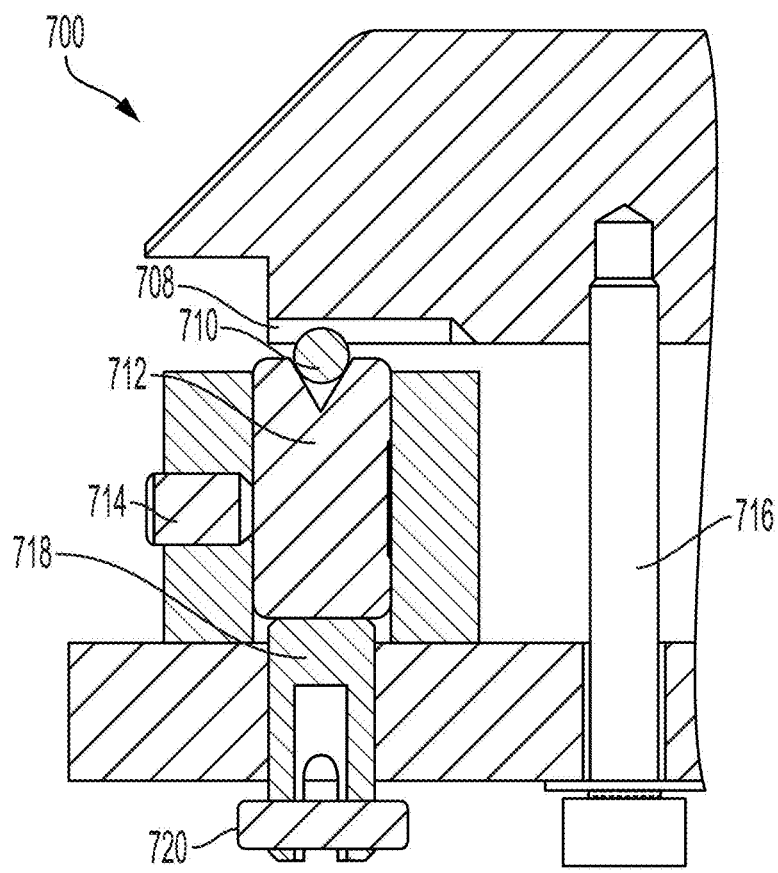
FIG. 7B shows a cross section of a foot of the kinematic support structure supporting the window support shown in FIG. 7A, according to illustrative embodiments of the invention.

FIG. 7A shows an imaging window 704 supported by a kinematic support structure. The kinematic support structure indirectly supports imaging window 704 by directly contacting window support 702. The kinematic support structure of FIG. 7A has three feet 700. A close up of one foot 700 is shown in FIG. 7B. V-shaped groove 708 in window support 702 is oriented to the center of imaging window 704 (e.g., such that the long axis of the groove intersects the center of imaging window 704), while the foot has a ball-shaped curved surface 710 that sits down into groove 708. Ball 710 is at the tip of piston 712, itself activated by fine-thread screw 718. Fine-thread screws serve as motion actuators, while pistons in their cylinders ensure proper motion guiding. Adjustment is made with respect to baseplate 706, to which is also attached a scanning stage (not shown). An optical chip is solidary to the scanning stage, so adjustment of the imaging window can be made with respect to the optical chip. During calibration (e.g., factory calibration), the height and tilt may be adjusted by moving up or down the 3 fine-thread screws. When nominal position is reached, the position of each foot can then be locked by one or more of the following means: lateral set screw 714 to lock piston 712 in place, lock nut 720 to lock fine-thread screw, and a retaining screw 716. In some embodiments, all of these means are located inside a housing that at least partially encloses optics of an imaging system and are thus not accessible to the user. A retaining screw may also be used to prevent an imaging window support from being removed (e.g., by a user).

Figure 8A:
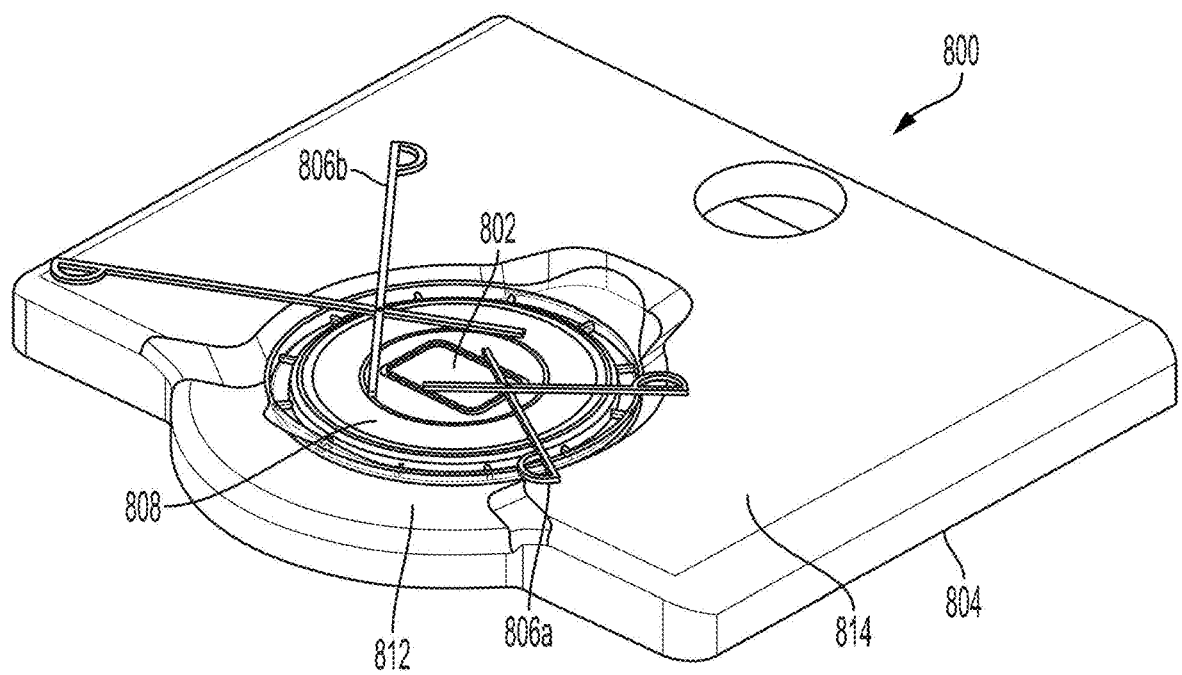
FIG. 8A shows a mounting surface of a microscope, according to illustrative embodiments of the invention.
Figure 8B:
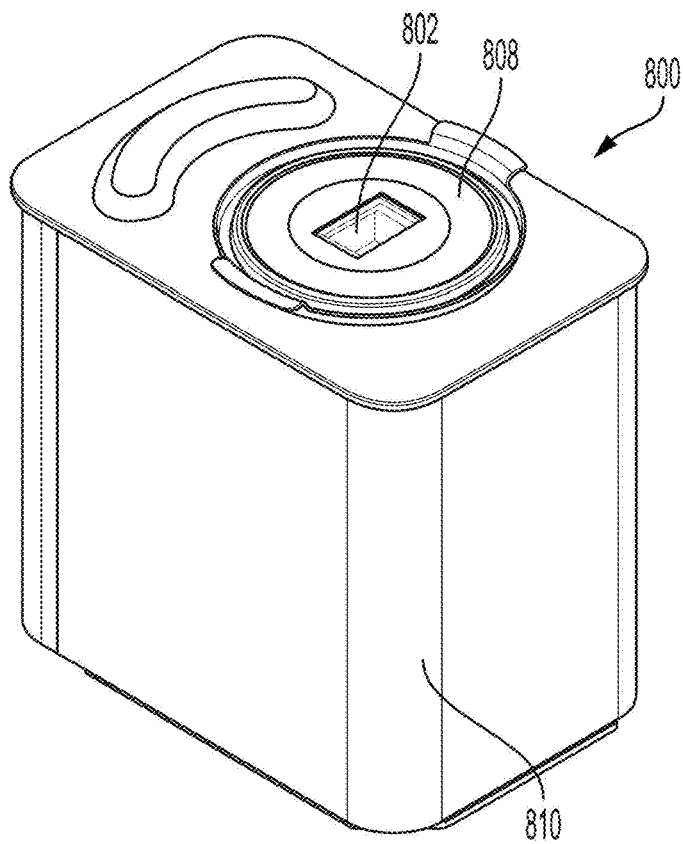
FIG. 8B is a zoomed out schematic of the mounting surface shown in FIG. 8A.

FIGS. 8A, 8B, and 8C show illustrative imaging system 800 with sample dish 808 disposed thereon. Illustrative imaging system 800 may comprise an optical chip or may not (e.g., may utilize a singular objective lens or other conventional optics). Illustrative imaging system 800 has an exposed working area (e.g., working surface and sample) that is available to a user during imaging (i.e., the exposed working area is not covered). A sample can be disposed on sample dish 808 without the need for an additional sample holder. Sample dish 808 comprises an optical interface that is exposed to a user of imaging system 800 during imaging such that the user can use forceps 806a-b can be used to position and/or orient a sample. Moreover, forceps 806a-b can remain in a desired position while imaging the sample due to the exposed interface. Transparent imaging window 802 can be seen through sample dish 808. Housing 804 comprises an imaging window support base 812 and upper working surface 814. Imaging window support base 812 is recessed from upper working sample 814 such that when sample dish 808 is mounted onto imaging system 800, the sample dish is positioned at or slightly below upper working surface 814. Such an arrangement allows easy lateral access to a sample from all sides of a sample, even during imaging. Moreover, since the imaging window support base 812 is recessed from upper working surface 814 and the exposed surface of sample dish 808 is near (e.g., at or slightly below) the same plane as upper working surface 814, tools (e.g., forceps) can easily be used and left in place during imaging (e.g., to hold a sample in a particular position). As shown in FIG. 8B, housing body 810 of housing 804 further contains at least a portion of an optical module of imaging system 800.

FIG. 8C, a cross section, shows imaging window 802 with sample dish 808 mounted thereon. Transparent imaging window 802 protrudes slightly from window support 818 of housing 804 such that sample dish 808 only contacts imaging system 800 at transparent imaging window 802. Window support 818 is shown without a tapered edge. Imaging window 802 is attached (e.g., glued) to window support 818 at an interface that exists between an overlapping portion of the imaging window and the window support. Optical chip 816 and other optical elements of an optical module (not shown) are confined, at least in part, by transparent imaging window 802 and window support 818.

Figure 8D:
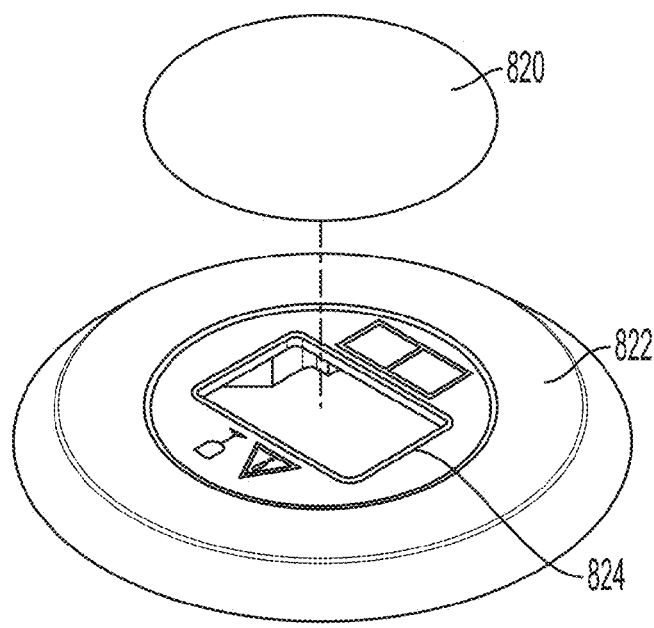
FIG. 8D shows a blow up of a window support and transparent imaging window, according to illustrative embodiments of the invention.

FIG. 8D shows a blowup of a portion of a microscope. Transparent imaging window 820 is disposed over imaging window support 822 which comprises opening 824. Transparent imaging window 820 may be attached (e.g., glued) to imaging window support 822. Imaging window support 822 is part of a housing of the microscope. In certain embodiments, a transparent imaging window is disposed at least partially above the transparent imaging window support such that a surface of the transparent imaging window is more than 30 micrometers (e.g., at least 100 micrometers) above a surface of the transparent imaging window support. In some embodiments, a transparent imaging window support comprises an opening having an area no more than 50% larger (e.g., no more than 40% larger or no more than 25% larger) than a field of view of the microscope (e.g., over which the illumination beam may be scanned). In some embodiments, an imaging artifact reducing fluid is disposed on a transparent imaging window during imaging with a substantially uniform thickness over at least a portion of the transparent imaging window that is at least as large as the area of the opening. In some embodiments, a transparent imaging window has an aperture that has the area of the opening.

Figure 8E:
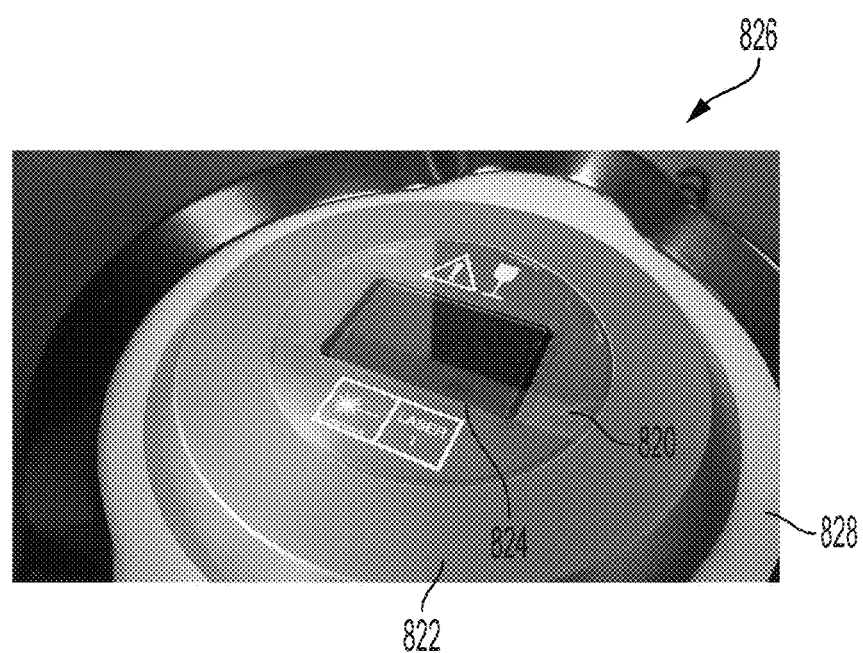
FIG. 8E is a photograph of a portion of a microscope, according to illustrative embodiments of the invention.

FIG. 8E is a photograph of a portion of an illustrative microscope. Housing 826 comprises imaging window support base 828 and imaging window support 822. Imaging window support 822 comprises opening 824. Transparent imaging window 820 is disposed on [e.g., attached (e.g., glued) to] imaging window support 822. In certain embodiments, an opening of an imaging window support is the same size (or substantially the same size) as a transparent imaging window. Imaging window support base 828, imaging window support 822, imaging window 820, and the rest of housing 826 form a waterproof seal that keeps any fluid away from (i.e., contains, at least in part) optics of the microscope, which are disposed below imaging window support 822). In some embodiments, a portion of an imaging artifact reducing fluid leaks from between a transparent imaging window and a transparent optical interface (e.g., thereby reducing its substantially uniform thickness) and is contained, at least in part, by an imaging window support base of a housing to which a transparent imaging window support is attached (e.g., wherein optics of the microscope are contained, at least in part, by the transparent imaging window support base of the housing such that the portion of the imaging artifact reducing fluid that has leaked cannot contact the optics). In some embodiments, an imaging window is centered in an imaging window support. In some embodiments, a window support comprises an opening and a transparent imaging window is larger in area than the opening.

Computing Devices

In certain embodiments, an imaging system comprising a computing device, wherein the computing device that is used to produce (e.g., construct) an image (e.g., a confocal image) based on back-emitted light detected by a detector of the imaging system. For example, in some embodiments, during imaging, an optical chip of an imaging system moves over a scan pattern and data derived from back-emitted light striking a detector at positions along the scan pattern is processed by a computing device to form an image for viewing by a user (e.g., on a display of the imaging system). In some embodiments, motion (e.g., of an optical chip or a sample) over a scan pattern during imaging is continuous. In some embodiments, motion (e.g., of an optical chip or a sample) over a scan pattern during imaging is "stop-and-go" such that motion temporarily ceases while image data is acquired and then resumes to the next position in the scan pattern. In some embodiments, a computing device constructs an image representing an optical slice of the fresh tissue sample based on the back-emitted light detected by the detector. In addition to computing images from data received from a detector, a computing device may provide additional connectivity (e.g., to healthcare or laboratory IT systems) and functionality to an imaging system. For example, an imaging system may comprise a display that allows a user to change imaging settings such as scan rate, scan size, scan step size, illumination intensity, or other similar scan settings. A computing device may be used as a controller for a scanning stage.

A computing device of an imaging system may not be local, relative to optics of the imaging system. For example, in some embodiments an imaging system sends information regarding the detected back-emitted light (e.g., an image captured by the camera) to a receiving device (e.g., a second computing device or a display) (e.g., remote from the first computer device—e.g., outside an operating theatre in which the system is located). In some embodiments, a computing device is configured to connect to a cloud server for storing images.

In some embodiments, an imaging system is controlled by a user, at least in part, by a touchscreen monitor. In some embodiments, an imaging system is controlled by user, at least in part, by a keyboard and mouse. In some embodiments, an imaging system is controlled by a user, at least in part, by a joystick and one or more hardware buttons. In some embodiments, a joystick and one or more hardware buttons are remote from the imaging system (e.g., in order to preserve sterility). For example, a device can be operated at a distance. If remote control comprising a joystick and one or more hardware buttons is covered with sterile bag, the remote control can be operated by a surgeon in the sterile area of the operating theater, even if an imaging system itself is not sterile and is located in a non-sterile area.

In some embodiments, an imaging system is connected to one or more remote monitors (e.g., to display images thereon) (e.g., an operating theater display system). An imaging system may be connected to a remote monitor by video cable or by wireless connection. In some embodiments, images produced by an imaging system are be displayed on an operating theater monitor(s) and are viewable from any location within the operating theater. Such a connection to a remote monitor can allow surgeons to remain near a patient (e.g., in a sterile area of an operating theater) while viewing images. Accordingly, images may be able to be viewed more easily by different specialists present at different locations in an operating theater.

In some embodiments, an imaging system connects to a radiology picture archiving and communication system (PACS) and/or a pathology PACS (e.g., thereby facilitating long term storage of images in existing hospital infrastructure, for example, for use by an interdisciplinary tumor board). In some embodiments, an imaging system connects to a laboratory information system (e.g., of a hospital) [e.g., thereby providing easy exchange of documentation, such as images or diagnostic assessments, from the imaging system to a postoperative assessment team (e.g., a pathologist)]. In some embodiments, an imaging system connects to an electronic patient record database of a hospital (e.g., to receive medical records of a patient and/or update the medical records of the patient). In some embodiments, an imaging system connects to a remote cloud server, for example, to send and receive images (e.g., for storage or archiving) or to provide collaborative capabilities. In some embodiments, a remote cloud server provides additional processing power to an imaging system.

In some embodiments, images are produced (e.g., reconstructed) based on output from a detector of an imaging system using a reconstruction technique (e.g., algorithm) that comprises: generating, by a processor of a computing device, a fixed number of masks [e.g., based, at least in part, on one or more scan characteristics (e.g., scan size and/or scan resolution) and/or one or more system characteristics (e.g., detector resolution or detector type)], wherein the fixed number of masks is independent of (i) a number of scan points in a scan and (ii) a number of micro optical elements in the array of micro optical elements; and reconstructing, by the processor of the computing device, an image based, at least in part, on the fixed number of masks (e.g., wherein no other masks are used in reconstruction).

In some embodiments, computer aided detection (CAD) is used to perform image analysis in order to identify and/or highlight areas or volumes of images indicative of cancer and/or high cancer risk. Accordingly, a user can be assisted in analyzing images produced by a system that implements a CAD technique (e.g., algorithm). CAD may utilize artificial intelligence (e.g., machine learning). Image analysis may be performed faster when using CAD (as compared to analysis performed by a trained or untrained user). In some embodiments, standardized analysis by AI model gets rid of the existing variations in analysis between different people.

A CAD technique may reach the analysis accuracy of an annotated image set from which it trained. In some embodiments, a training set is annotated by top professionals such that a CAD technique offers nearly the same or the same level of accuracy to all users. In some embodiments, automated image analysis is performed in order to recognize specific patterns (e.g., indicative of cancer and/or high risk of cancer) in images using a computer, based on an artificial model (e.g., a deep neural network).

Figure 9B:
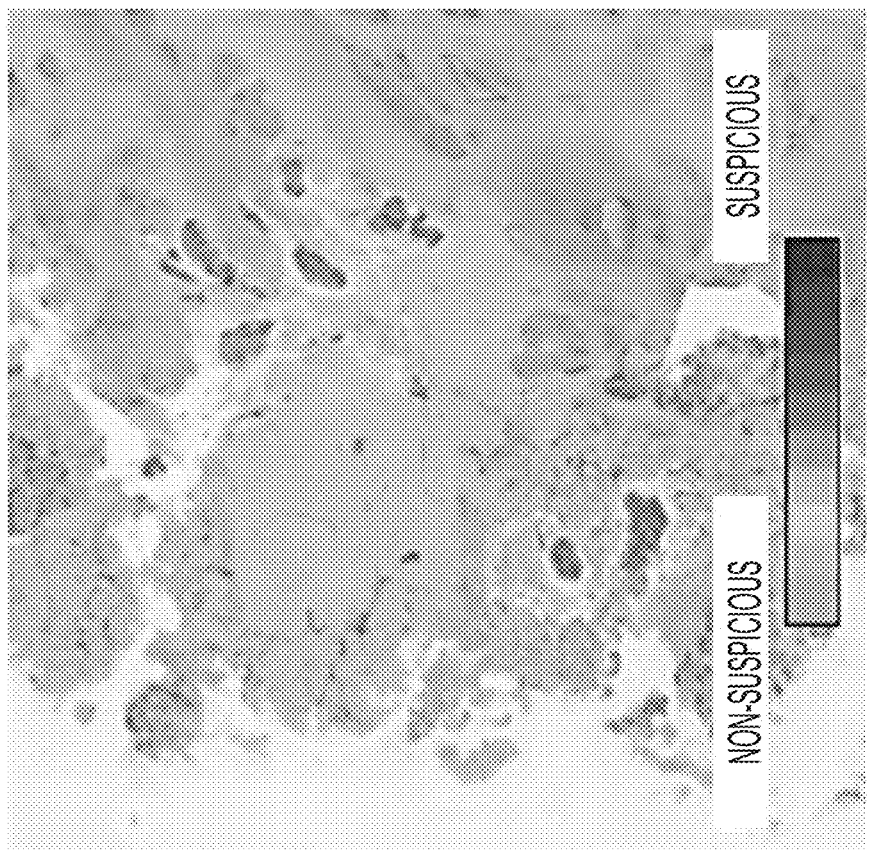
FIG. 9B is a representation of the image shown in FIG. 9A after analysis using a computer aided detection (CAD) technique (e.g., algorithm), according to illustrative embodiments of the invention.
Figure 9A:
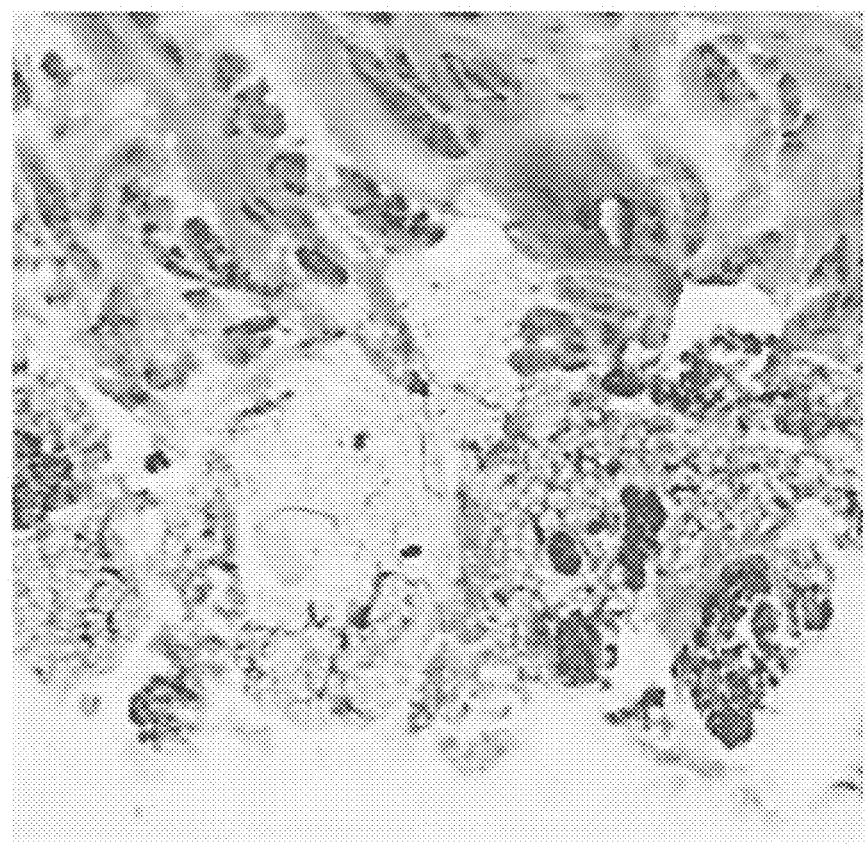
FIG. 9A is an illustrative image produced by an imaging system, according to illustrative embodiments of the invention.

Imaging large samples (e.g., up to 10 cm in size) at a microscopic resolution (e.g., resolution of between 0.5 and 10 micrometers) can generate a large amount of data. Finding a small cancer structure (e.g., much smaller than a total image area or volume) in such data can take a human significant amount of time (e.g., 10 minutes). In some embodiments, a CAD speeds up this analysis into a time frame that is more suitable for use in intraoperative setting. In some embodiments, a CAD machine learning technique is trained with images in which pathology expert delineated the cancerous areas. In some embodiments, images are annotated by a panel of pathology expert to eliminate variability between different pathologists. Without wishing to be bound by any particular theory, the more images used in a training set, the better the AI model will be at detecting specific cancer patterns. In some embodiments, a cloud server is used such that a CAD technique runs on one or more computing servers that are remote from an imaging system (e.g., in order to speed up analysis time). In some embodiments, a CAD technique runs on embedded hardware (e.g., on one or more dedicated GPU cards of a system). Running a CAD technique on embedded hardware may allow CAD to be used, for example, in the absence of internet connection and/or other wired or wireless network connection. Accordingly, in certain embodiments, an imaging system self-contained in that all image acquisition and processing occurs, or can occur, locally (e.g., on local hardware). In some embodiments, an imaging system sends and receives encrypted and/or anonymized image data to the one or more cloud servers for automated analysis. In some embodiments, images analyzed by a CAD technique are returned to an imaging system (e.g., for display) either in a binary format (e.g., an assessment of cancer or no cancer and, optionally, a cancer type). In some embodiments, a CAD technique produces a graduated heat map (e.g., indicating a level of confidence of cancer existing by area). For example, an image that may be produced using an imaging system disclosed herein is shown in FIG. 9A. FIG. 9B shows a graduated heat map generated from the image in FIG. 9A using a CAD technique.

Illustrative Imaging Systems and Methods

In an imaging system, a scanning stage is used to scan a pattern during imaging. In accordance with some embodiments, an illustrative imaging system comprises a transparent imaging window, a scanning stage, and an optical module comprising (i) a photon source, (iii) focus, imaging and collimating lenses, (iii) optionally, first and second apertures, a filter, (iv) a detector, and (v) an optical chip comprising an array of micro optical elements, wherein the scanning stage is attached to the optical chip by a support. Accordingly, in order to image a sample disposed on or over the transparent imaging window, the scanning stage actuates an actuator to move the stage support along a scan pattern thereby moving the optical chip relative to the imaging window and the detector along the scan pattern (e.g., wherein the position of the imaging window and the detector are fixed, at least during imaging). Therefore, the mass of the imaging window, sample, and optics other than the optical chip are not necessarily in motion during imaging.

In accordance with some embodiments, an illustrative imaging system comprises a transparent imaging window, a scanning stage, and an optical module comprising (i) a photon source, (iii) focus, imaging and collimating lenses, (iii) optionally, first and second apertures, a filter, (iv) a detector, and (v) an optical chip comprising an array of micro optical elements, wherein the scanning stage is attached to the transparent imaging window by a support. Accordingly, in order to image a sample disposed on or over the transparent imaging window, the scanning stage actuates an actuator to move the stage support along a scan pattern thereby moving the imaging window relative to the optical chip and the detector along the scan pattern (e.g., wherein the position of the optical chip and the detector are fixed, at least during imaging).

Figure 10A:
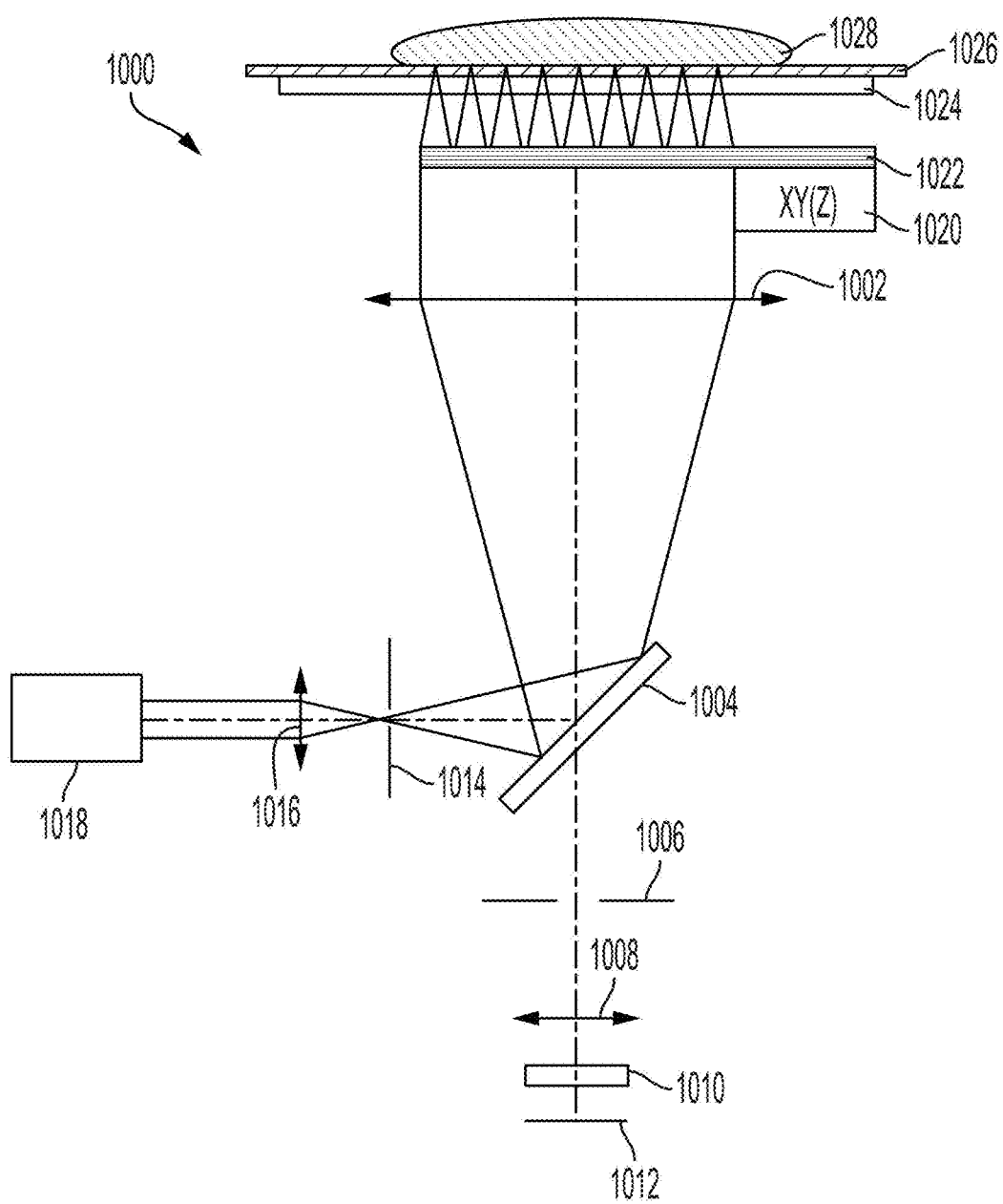
FIG. 10A is a schematic of an illustrative imaging system showing illumination of a tissue sample, according to illustrative embodiments of the invention.
Figure 10B:
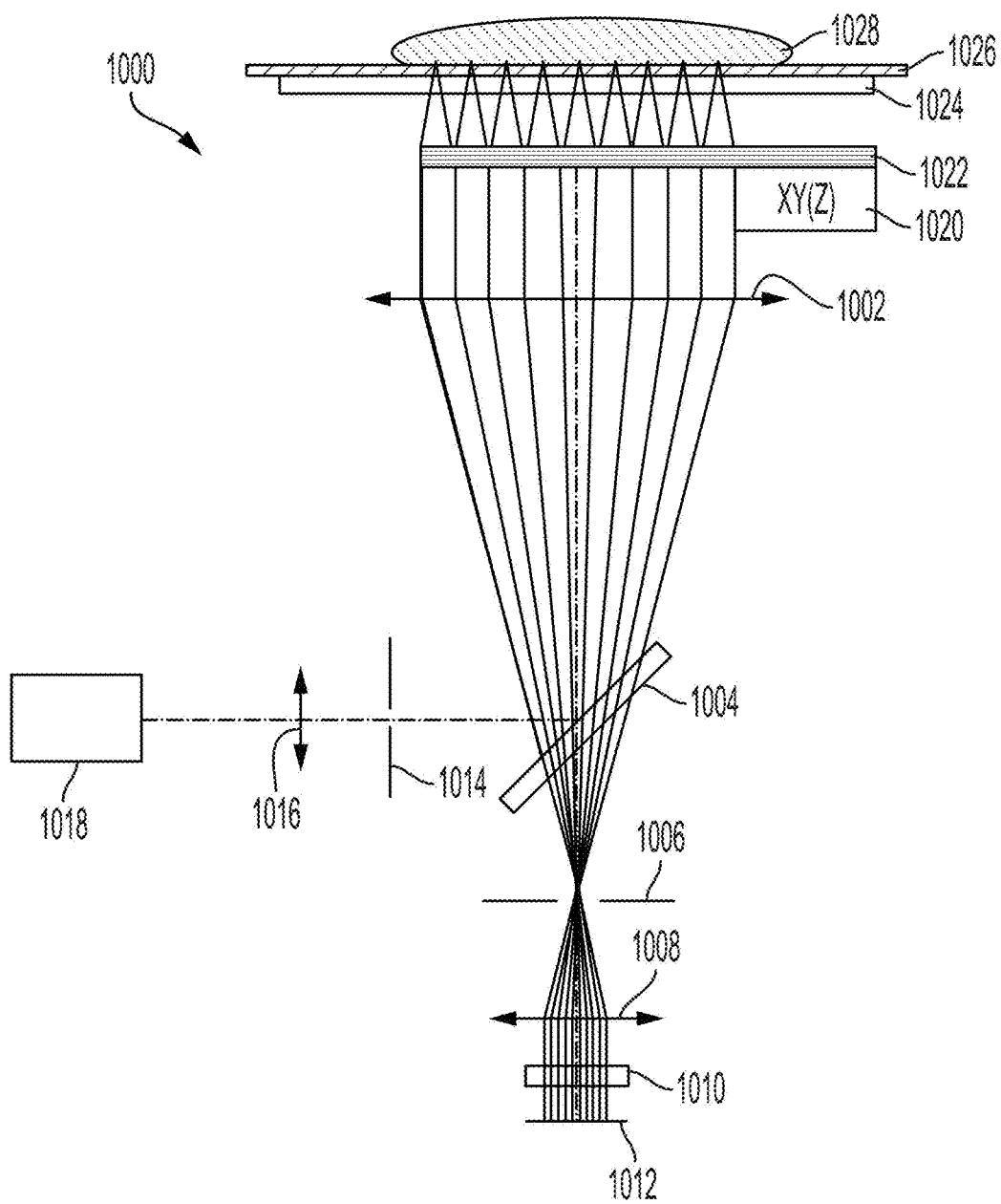
FIG. 10B is a schematic of the illustrative imaging system according to FIG. 10A showing detection of back-emitted light from a sample by a detector, according to illustrative embodiments of the invention.

FIG. 10A is a schematic of illustrative imaging system 1000 showing behavior of optics of the illustrative system during illumination of a tissue sample. FIG. 10B is a schematic illustrative imaging system 1000 showing detection of back-emitted light from a sample by a detector. Referring now to FIG. 10A, a laser 1018 that provides light with a wavelength that is between 450 nm and 490 nm provides an illumination beam to a focusing lens 1016. The illumination beam passes through the focusing lens 1016 and a first aperture 1014 before being directed by a dichroic mirror 1014. The dichroic mirror reflects the illumination beam onto a collimating lens 1002. The illumination beam is collimated by collimating lens 1002 and the collimated illumination beam propagates to an optical chip 1022. The optical chip comprises an array of micro optical elements. Micro optical elements in an array of micro optical elements may be refractive lenses, Fresnel zone plates, micro reflective objectives, GRIN lenses, or micro lenses. In certain embodiments, an optical chip comprises an array of refractive micro lenses. The micro optical elements focus light from the collimated illumination beam onto a sample through an imaging window. In this case, a sample 1028 is disposed on a disposable sample holder 1026 that is mounted directly onto an imaging window 1024. In some embodiments, a sample is disposed over an imaging window (e.g., on a sample dish) (e.g., without contacting the imaging window) during imaging. In some embodiments, sample holder 1026 is not present and a sample is mounted directly on a transparent imaging window during imaging. Use of a sample dish may reduce or eliminate the need to clean (e.g., sterilize) a transparent imaging window when changing samples. FIGS. 6A, 6B, 8A, 8B, and 8C show illustrative mounting interfaces comprising imaging windows onto which a sample dish (e.g., a disposable sample dish) is mounted in order to image a sample that could be used in imaging system 1000.

Referring again to FIG. 10A, optical chip 1022 is connected to a support of a scanning stage 1020. Scanning stage 1020 moves optical chip 1022 along a scan pattern during imaging using a controller and an actuator connected to the support. Each micro optical element of optical chip 1022 produces a tight focus (e.g., a small spot) of light from the collimated illumination beam on or in a sample during imaging on a common focal (imaging) plane that is on or in the sample.

FIG. 10B is a schematic of illustrative imaging system 1000 showing behavior of the optics shown in FIG. 10A during detection. Light from the collimated illumination beam focused onto the sample 1028 by the array of micro optical elements in the optical chip 1022 produces light (e.g., fluorescence or luminescence) in the sample 1028 that is back-emitted through imaging window 1024 towards optical chip 1022. Back-emitted light is then collected by the micro optical elements in the array in optical chip 1022 and directed towards a detector 1012. Back-emitted light passes through dichroic mirror 1004 as it is within the transmission band of the mirror. Back-emitted light then passes through a second aperture 1006 and is collimated by an imaging lens 1008. The collimated back-emitted light passes through an emission filter 1010 and then onto a detector 1012. Detector 1012 is a CMOS camera that comprises an array of detector elements (e.g., pixels in the camera) that each receive back-emitted light from a micro optical in the array of optical elements in optical chip 1022. An opaque enclosure may be disposed about an optical path of the back-emitted light that passes through filter 1010 in order to block ambient (e.g., stray) light from being incident on detector 1012.

An imaging system may be used for in-operating-theatre imaging of fresh tissue resected during surgery (e.g., cancer surgery). In some embodiments, an imaging system is operable to image a portion of a sample in less than 10 minutes (e.g., less than 5 minutes, less than 3 minutes or less than 2 minutes). In some embodiments, a system is operable to image a portion of the sample in less than 2 minutes (e.g., less than 90 seconds or less than 1 minute). IN some embodiments, the portion of the sample has an area of at least 10 cm$^2$ (e.g., at least 12 cm$^2$, at least 15 cm$^2$, or at least 17 cm$^2$). In some embodiments, a sample has a volume of no more than 10 cm×10 cm×10 cm and the system is configured to image a full outer surface of the sample in an imaging time of no more than 45 minutes (e.g., no more than 30 minutes).

Figure 11B:
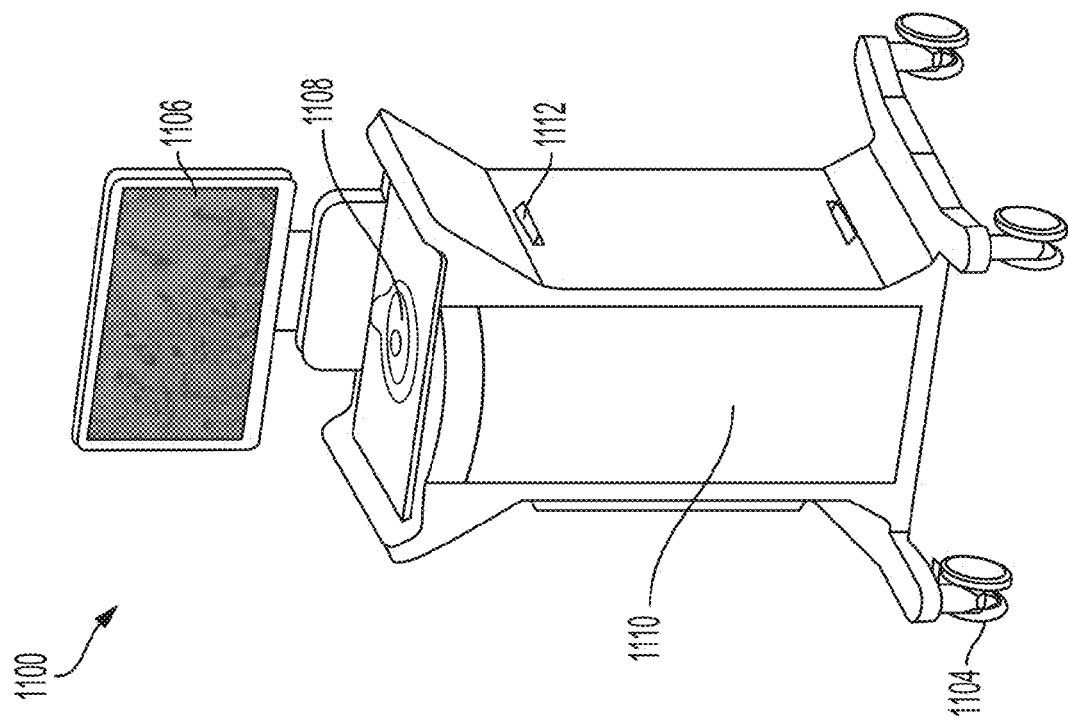
FIG. 11B is a representation of the illustrative imaging system in FIG. 11A during use, the illustrative imaging system having an exposed sample with significant lateral access, according to illustrative embodiments of the invention.
Figure 11A:
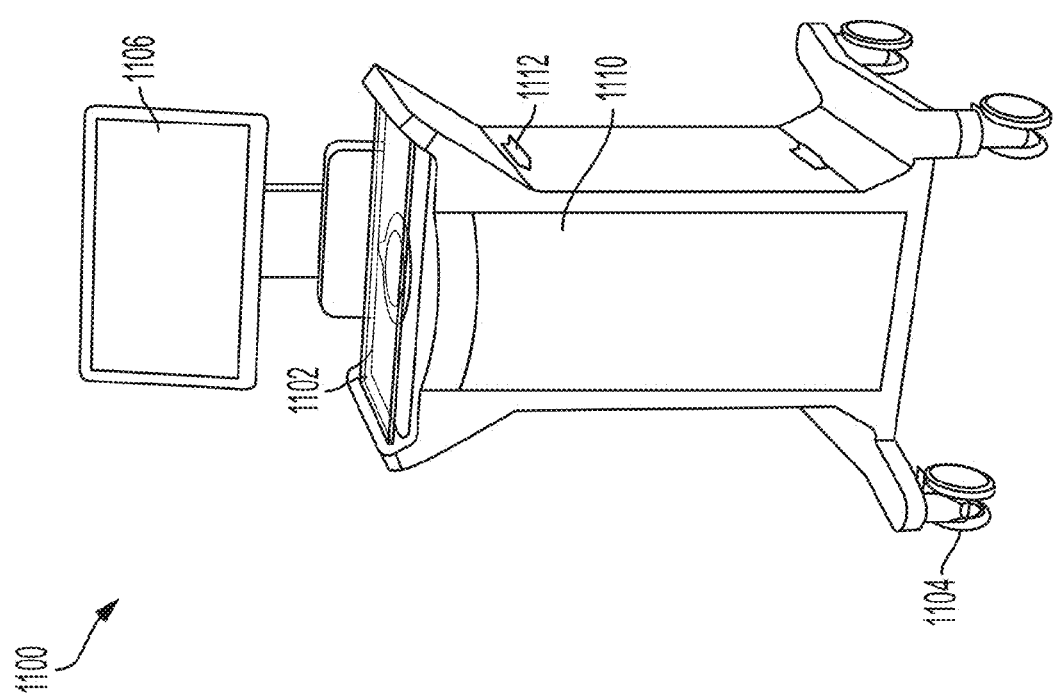
FIG. 11A is a representation of an illustrative imaging system when not in use, the illustrative imaging system comprising a display, according to illustrative embodiments of the invention.

Referring now to FIGS. 11A and 11B, illustrative imaging system 1100 comprises an outer housing 1110 that contains an optical module (not shown). Illustrative imaging system 1100 comprises a touch screen display 1106. Imaging system 1100 has four lockable wheels 1104 for easy positioning (e.g., in an operating theater or laboratory). Removable transparent cover 1002 protects working area 1108. In FIG. 11A, cover 1102 is over working area 1108 as is the case when imaging system 1100 is not in use, thereby keeping dust and other contaminants away from a transparent imaging window in the working area 1108. In FIG. 11B, working area 1108 is fully exposed, as is the case during imaging. A sample dish is mounted over the transparent imaging window of system 1100 in FIG. 11B. As can be seen in FIG. 11B, a user can easy access and manipulate a sample during imaging when cover 1102 is removed. Imaging system 1100 comprises attachment points 1112 on a side of outer housing 1110 to store cover 1102 during operation.

Figure 12:
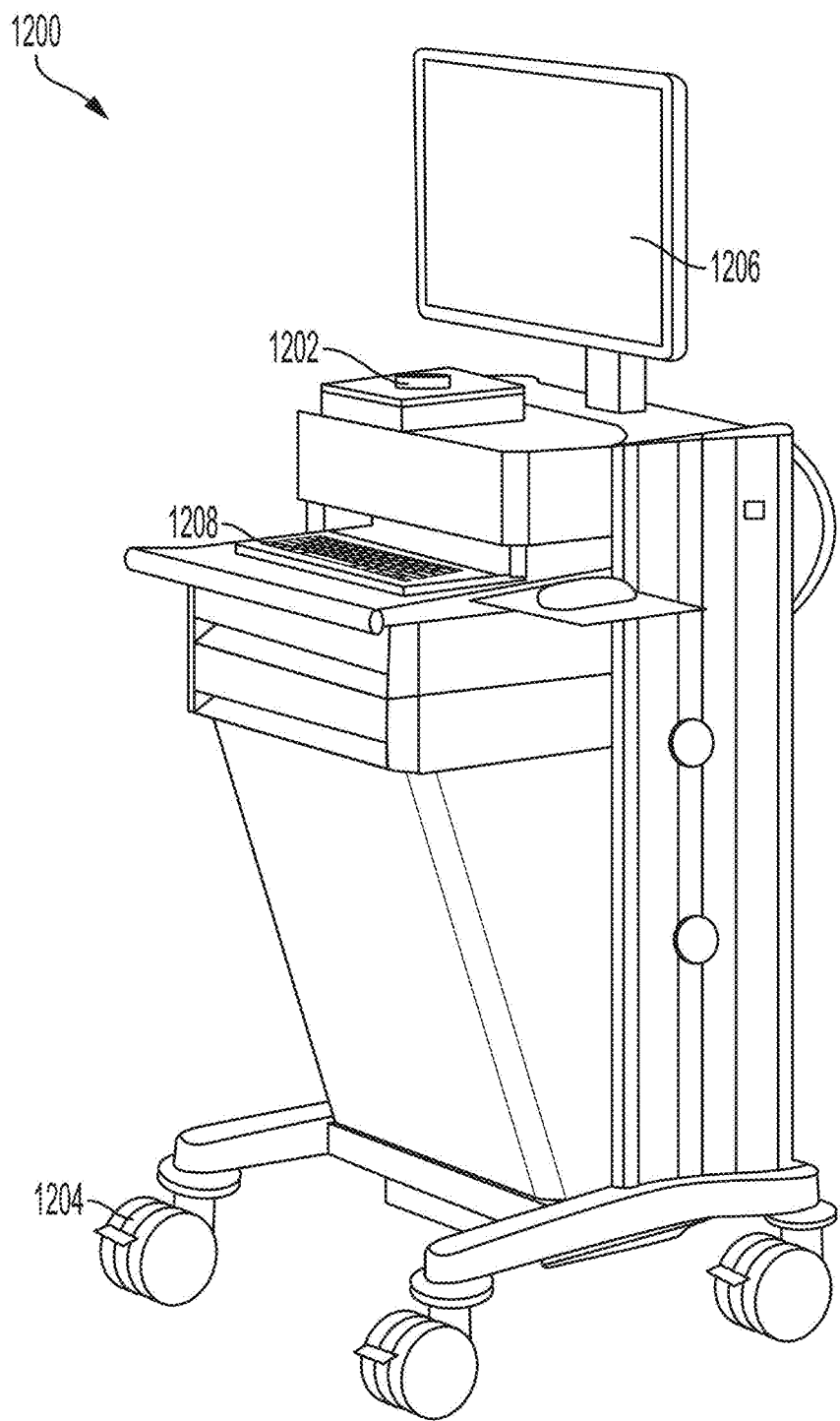
FIG. 12 is a representation of an illustrative imaging system, comprising a display, that is enclosed by a housing and operated by a keyboard and mouse, according to illustrative embodiments of the invention.

FIG. 12 shows an alternate illustrative imaging system 1200. Illustrative imaging system 1200 has four lockable wheels 1204 for easy positioning in a room (e.g., operating theater or laboratory) and a display 1206. Illustrative imaging system 1200 is controlled by keyboard and mouse 1208. The sample working area 1202 is covered by a cover that keeps dust and other contaminants away from a transparent imaging window.

Figure 13:
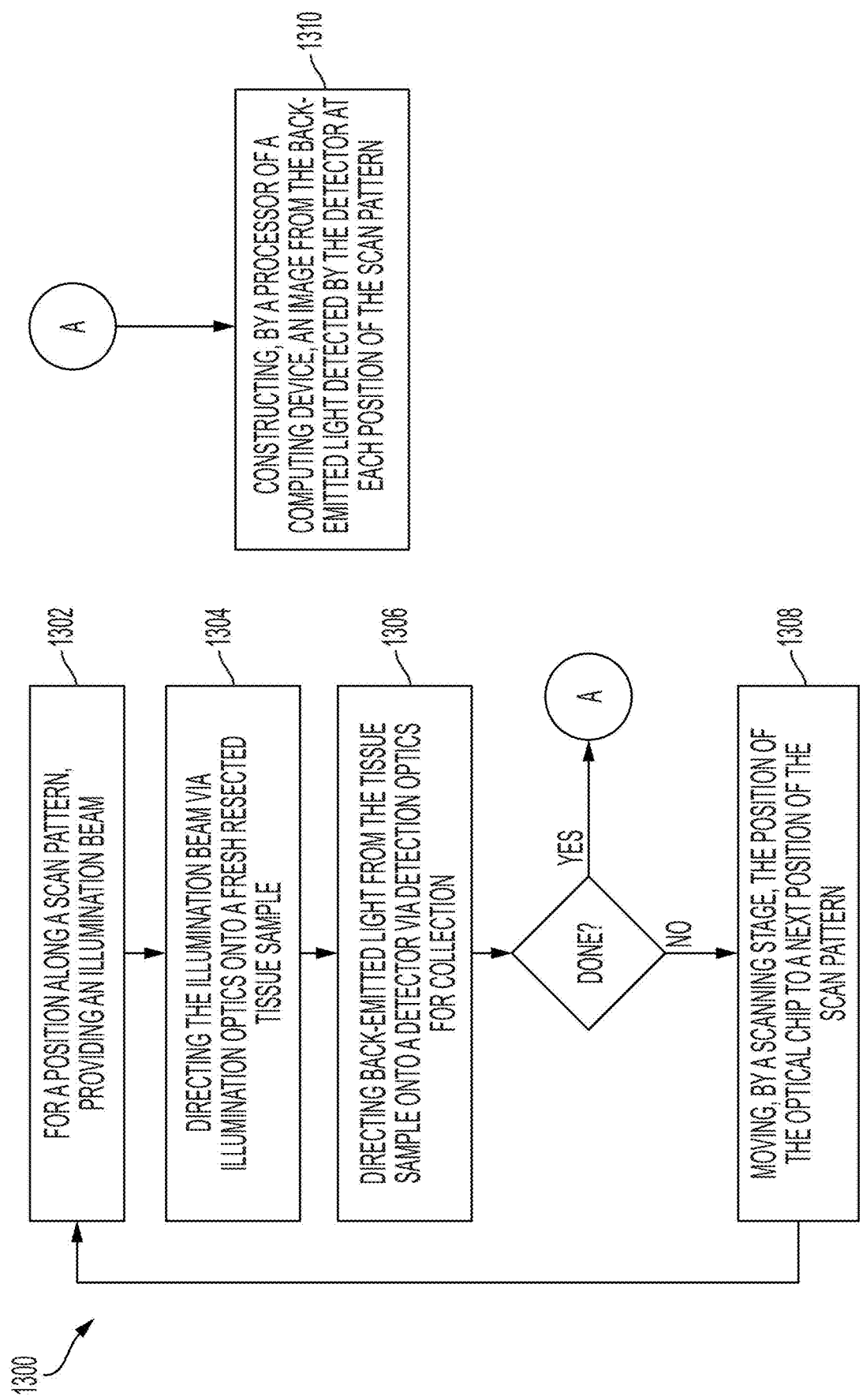
FIG. 13 is a block diagram of an illustrative method of using an imaging system, according to illustrative embodiments of the invention.

FIG. 13 is a block diagram of an illustrative method 1300 of using an imaging system to form an image. In step 1302, for a position along a scan pattern, an illumination beam is provided by a photon source. In step 1304, the illumination beam is directed by illumination optics onto a fresh resected tissue sample. In step 1306, back-emitted light from the tissue sample is directed onto a detector via detection optics. If there are remaining positions in a scan pattern for which back-emitted light has not been collected, method 1300 proceeds to step 1308, wherein an optical chip is moved to a next position in the scan pattern and steps 1302, 1304, and 1306 are repeated. Such repetition may proceed continuously or discretely. That is, an optical chip may be continually in motion along a scan pattern while back-emitted light is collected periodically. Alternatively, an optical chip may pause in a particular position while back-emitted light is collected by a detector before moving to a next position. Once a scan pattern is complete, method 1300 proceeds to final step 1310, wherein a computing device constructs an image based on the back-emitted light collected by the detector at each position of the scan pattern. In some embodiments, a detector output signal is sent to a remote computing device (e.g., that is not part of an imaging system) for processing, such as image reconstruction. In some embodiments, an image is transmitted via a network to a receiving device (e.g., a second computing device or a display) such that a pathologist in a remote location (e.g., outside of the operating theatre) can perform the pathology assessment.

In some embodiments, step 1310 comprises: generating, by a processor of a computing device, a fixed number of masks [e.g., based, at least in part, on one or more scan characteristics (e.g., scan size and/or scan resolution) and/or one or more system characteristics (e.g., detector resolution or detector type)], wherein the fixed number of masks is independent of (i) a number of scan points in a scan and (ii) a number of micro optical elements in an array of micro optical elements; and reconstructing, by the processor of the computing device, an image based, at least in part, on the fixed number of masks (e.g., wherein no other masks are used in reconstruction).

In some embodiments, method 1300 comprises, prior to providing the illumination beam for illuminating the sample, staining the sample with a fluorescent stain and placing the sample in/on the sample dish. In some embodiments, the sample is stained with a fluorescent stain (e.g., proflavine, acridine orange, hematoxylin or eosin).

In some embodiments, a method comprises using an imaging system as disclosed herein (e.g., an imaging system in accordance with FIGS. 10A and 10B) to analyze an image of a sample (e.g., automatically, semi-automatically, or manually) for identification of disease (e.g., cancer) for purposes of tissue removal and/or preservation in a surgical procedure (e.g., for intraoperative margin assessment in breast conserving surgery).

Table 1 lists optics and characteristics of the optics of an illustrative imaging system. Such an illustrative imaging system can be physically arranged in accordance with the illustrative imaging system shown in FIG. 10A and FIG. 10B, for example. Moreover, such an illustrative imaging system can be used to perform methods of imaging, for example in accordance with those illustrative methods illustrated in FIG. 13.

TABLE 1

| Optics of an Illustrative Imaging System | |
|---|---|
| FOCUSING LENS | |
| Type | Aspheric lens |
| Focal Length | 1.45 mm |
| Diameter | 2.4 mm |
| COLLIMATING LENS | |
| Type | Cemented achromatic doublet |
| Focal Length | 200 mm |
| Diameter | 75.0 mm |
| IMAGING LENS | |
| Type | Cemented achromatic doublet |
| Focal Length | 19 mm |
| Diameter | 12.7 mm |
| FIRST APERTURE | |
| Diameter | 1.0 mm |
| SECOND APERTURE | |
| Diameter | 3.0 mm |
| BEAM SPLITTER (DICHROIC MIRROR) | |
| Reflection Band | 452-490 nm |
| Transmission Band | 505-800 nm |
| Dimensions | 25.0 mm × 36.0 mm × 1.0 mm |
| FILTER | |
| Type | Longpass filter |
| Cut-off Wavelength | 500 nm |
| Dimensions | ø25.0 mm × 3.5 mm |
| CAMERA | |
| Definition | VGA (640 × 480 pixels) |
| Frame Rate | 500 fps |
| PHOTON SOURCE (LASER) | |
| Wavelength | 488 nm |
| Power | 200 mW |
| Beam Diameter | approx. 1.0 mm |

Illustrative Systems and Methods for Mapping Orientations of Resected Tissue Samples Certain embodiments of the present disclosure include systems and/or methods that allow image data associated with a specimen to be associated with a location from which the specimen was obtained (e.g., a location on a body) and/or an orientation of the specimen during acquisition of the image data by an imaging system. The image data may then be stored (e.g., in a database) along with the associated location and/or orientation data, allowing, for example, a user to efficiently track orientation of a sample when imaging more than one face of a specimen (e.g., during whole surface mapping). In certain embodiments, the imaging system may be an imaging system as described herein. In other embodiments, the imaging system may be a device known in the art (e.g., a commercially available fluorescence microscope).

Figure 14:
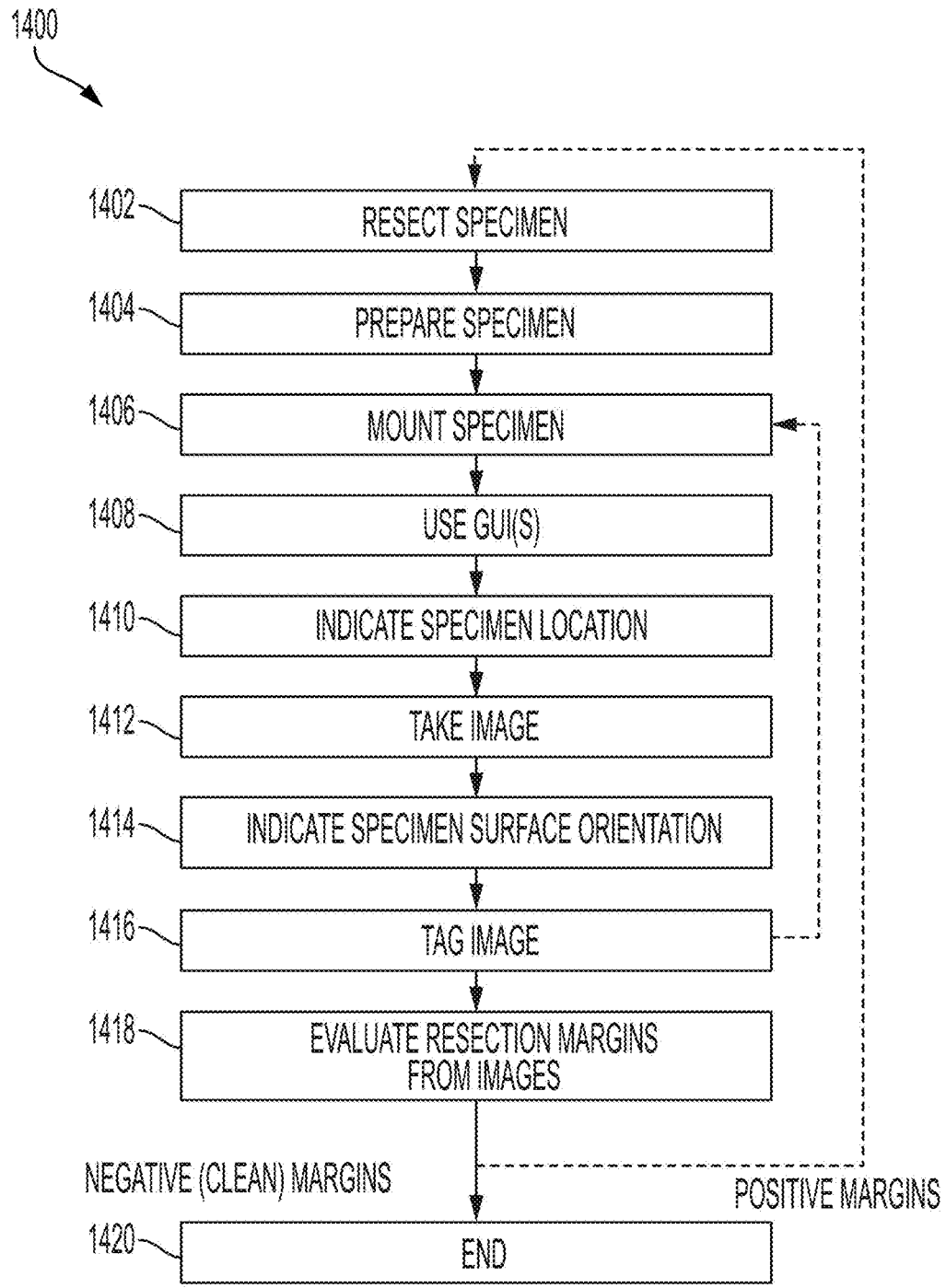
FIG. 14 is a flowchart showing an illustrative process of imaging tissue specimen, according to illustrative embodiments of the invention.

FIG. 14 is a flowchart showing an illustrative process 1400 of imaging a tissue specimen, according to illustrative embodiments of the present invention. In certain embodiments, the process 1400 is performed during a surgery within an operating room. In certain embodiments, the process 1400 is performed in a postoperative assessment procedure after a surgery in which the tissue specimen is resected. The process 1400 can start with step 1402. Illustrative process 1400 can be used to track location and orientation of a sample when imaging more than one face of a specimen (e.g., during a whole surface mapping). Location and/or orientation data (e.g., received from a GUI) may be stored in a database and associated with an image such that the location and/or orientation of a sample when an image was taken can be viewed when viewing the image (e.g., in a report, such as a PDF report). In some embodiments, location and/or orientation data is received from a GUI and stored in metadata of an image.

At step 1402, a tissue specimen can be obtained through a surgical resection procedure performed by a physician (e.g., a general surgeon, a surgical specialist, or other qualified medical service provider). In certain embodiments, the resection procedure is performed in a body or anatomical structure. In certain embodiments, the excised tissue specimen is a tissue sample comprising cancer. For example, systems and methods disclosed and described herein are useful for imaging surfaces of, inter alia, breast tissue, skin tissue, ear, nose, or throat tissue, brain tissue prostate tissue, or gastrointestinal tract (GI) tissue (e.g., comprising cancer). Location and/or orientation of samples may be recorded for each of such tissues as multiple surfaces (e.g., portions of a continuous surface) are imaged. In certain embodiments, the excised tissue specimen comprises breast cancer tissue.

At step 1404, the tissue specimen can be prepared for imaging. In certain embodiments, the tissue specimen is marked to indicate an orientation of the specimen with respect to the body or anatomical structure. For example, surgical sutures can be used to show specimen orientation, with varying suture length or number of sutures representing different aspects of the specimen. Other tools or methods can also be used in lieu of sutures (e.g., ink, e.g., a clip or clips).

In certain embodiments, the tissue specimen is stained with an agent before it is positioned in the imaging system in order to enhance image contrast. For example, the agent can be Proflavine (CAS 92-62-6) or Acridine Orange (CAS 494-38-2). Detailed tissue staining procedures are described in scientific literature, such as in Ragazzi M. et al. "Fluorescence confocal microscopy for pathologists", Modern Pathology (2014) 24, 460, and Dobbs J. L. et al. "Feasibility of confocal fluorescence microscopy for real-time evaluation of neoplasia in fresh human breast tissue", Journal of Biomedical Optics (2013) 18, 106016. In certain embodiments, an illustrative procedure for staining tissue specimens with either Proflavine or Acridine Orange is: i) swab the fresh tissue specimen briefly to remove excess blood with paper towel or compress; ii) dip the tissue specimen into the contrast agent solution (0.01% concentration) for 30 seconds; and iii) rinse by dipping the specimen few seconds in saline solution.

At step 1406, the tissue specimen can be mounted in the imaging system. In certain embodiments, the tissue specimen is positioned on the transparent imaging window covered by a sample dish. In order to obtain high quality images, it can be recommended that the face of interest of the specimen is pointed downwards on the imaging window and the region of interest of the specimen is centered over the imaging window. Embodiments of various components and configurations of an imaging window and a sample dish are described in detail in U.S. Provisional Patent Application Nos. 62/597,346, 62/579,705, and 62/675,368.

At step 1408, one or more graphical user interfaces (GUIs) can be used on a computing device associated with the imaging system to control the imaging system and/or receive image data from the imaging system.

Figure 15A:
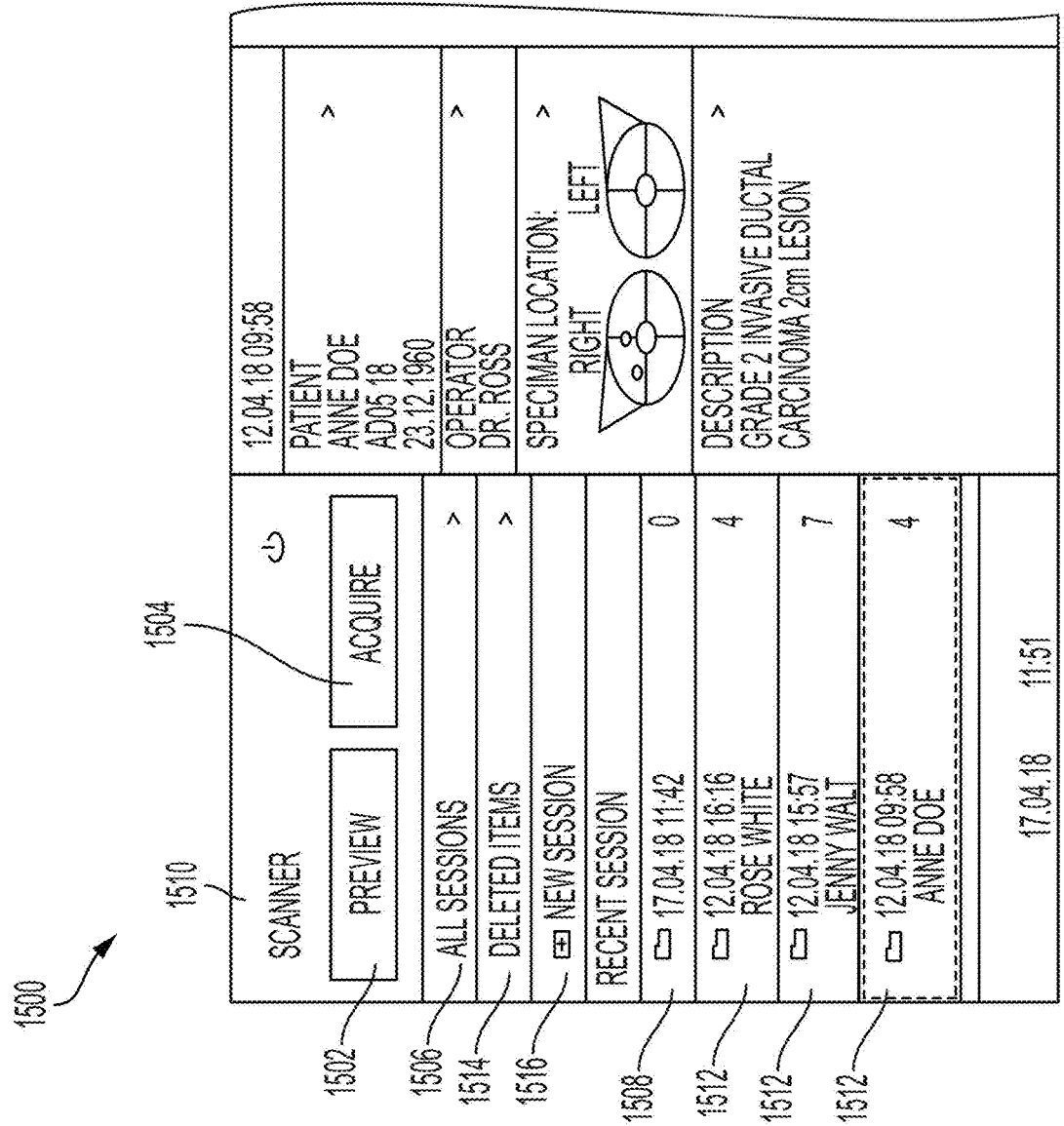
FIG. 15A is a first portion of a screenshot showing an illustrative graphic user interface (GUI) of the imaging system, according to illustrative embodiments of the invention.
Figure 15B:
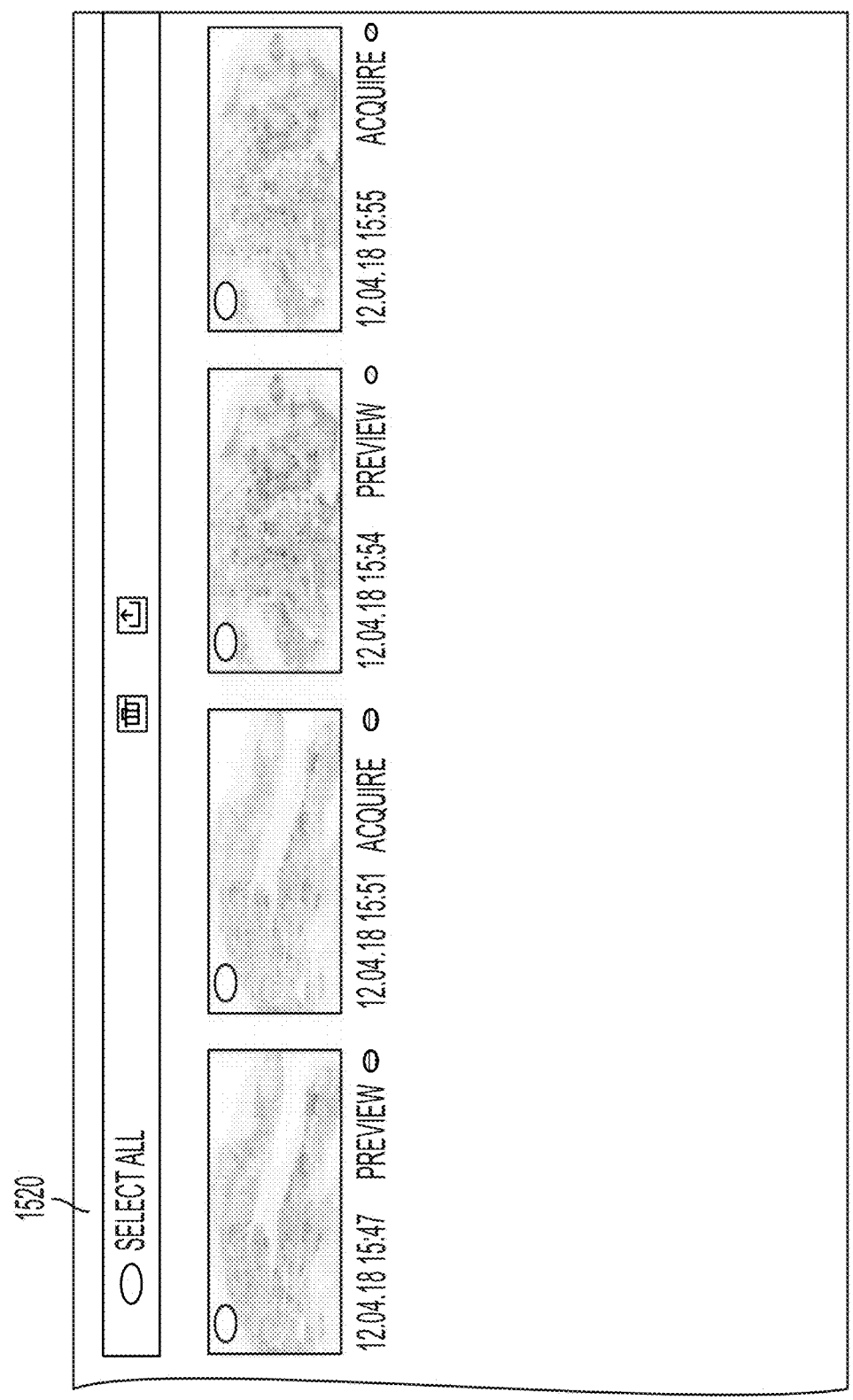
FIG. 15B is a second portion of the screenshot of FIG. 15A showing an illustrative graphic user interface (GUI) of the imaging system (e.g., where the second portion in FIG. 15B would be shown to the right of the first portion shown in FIG. 15A), according to illustrative embodiments of the invention

Referring to FIGS. 15A and 15B, an illustrative GUI 1500 of a user interface module of the imaging system can include a control panel 1510 and a gallery pane 1520. The control panel 1510 can include tools for controlling the image capturing process, such as buttons for "Preview" 1502, "Acquire" 1504, and "Cancel" (not shown in FIGS. 15A and 15B). When the "Preview" button 1502 is clicked, the system can launch a fast, low resolution imaging of the specimen. When the "Acquire" button 1504 is clicked, the system can launch a high resolution imaging of the specimen. The "Cancel" button can be used to interrupt any ongoing imaging process. The control panel 1510 can also include a progress indicator which displays the image visualization progress during an imaging process.

The control panel 1510 can include tools for handling sessions and images. In certain embodiments, the control panel 1510 presents the list 1506 of all sessions sorted top-down in reverse chronological order, so that the latest sessions appear on top of the list. Sessions in the list can be described with the date and time they have been created, with the number of images they contain and optionally, with the patient name, if documented. In certain embodiments, the control panel 1510 shows a current session 1508 to which newly captured images will belong. In certain embodiments, the control panel 1510 shows previous sessions 1512 that were performed on the system (and were not deleted). In certain embodiments, the control panel 1510 displays previously deleted content (e.g., images and sessions) 1514 which can be reviewed, restored to their original locations, or permanently deleted from the system. In certain embodiments, the control panel 1510 includes a "New Session" button 1516 for creating a new session on the system that automatically becomes the current session so all newly produced images will belong to this new session. In certain embodiments, the control panel 1510 includes a clock showing current date and time. In certain embodiments, the control panel 1510 includes a "Turn Off" button for shutting down the system.

The gallery pane 1520 can allow a user to browse through sessions and images, and manage their related contextual data. In certain embodiments, the gallery pane 1520 includes a summary view of images of a single session or a summary view of all sessions. For example a single session can comprise images of different surfaces (e.g., different portions of a continuous surface) of sample, such as a resected tissue sample. In certain embodiments, the contextual data includes one or more of date and time of when the session was created, patient data (e.g., patient name, patient ID, patient birthday, etc.), operator data (e.g., operator name, etc.), specimen location (e.g., the location in the patient where the specimen was taken from), and session description (e.g., a textual description of the session). The gallery pane can display either a summary view of images of a single session or a summary view of all sessions. Color tags can be used to represent specimen locations defined through a session's specimen location interface (e.g., interface 1700 in FIG. 17). An existing image or a newly produced image can be opened in an image examiner screen. A detailed illustrative embodiment of the configuration of the image examiner screen is shown in FIGS. 16A and 16B.

Figure 16A:
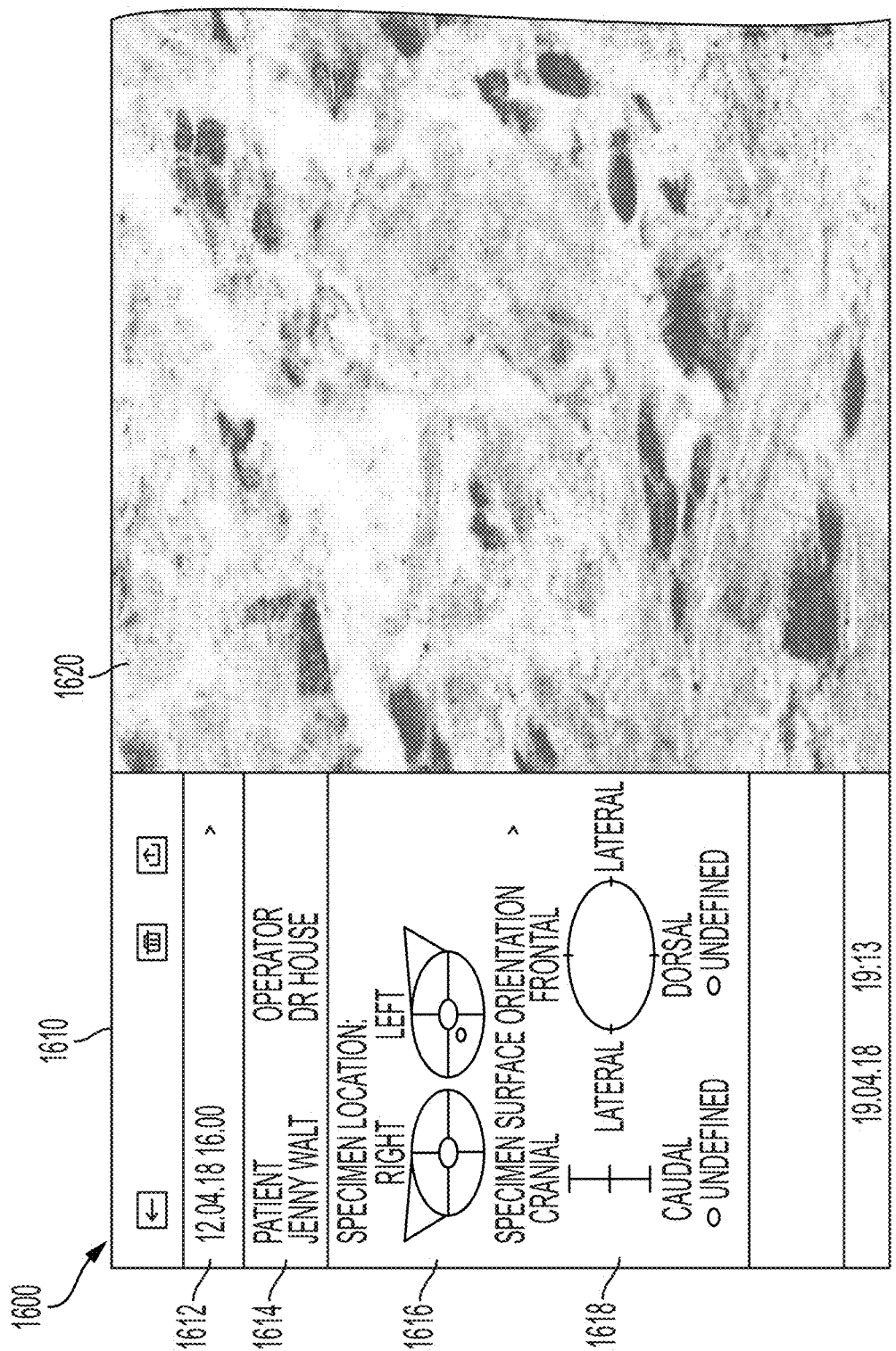
FIG. 16A is a first portion of a screenshot showing an illustrative image examiner screen, according to illustrative embodiments of the invention.
Figure 16B:
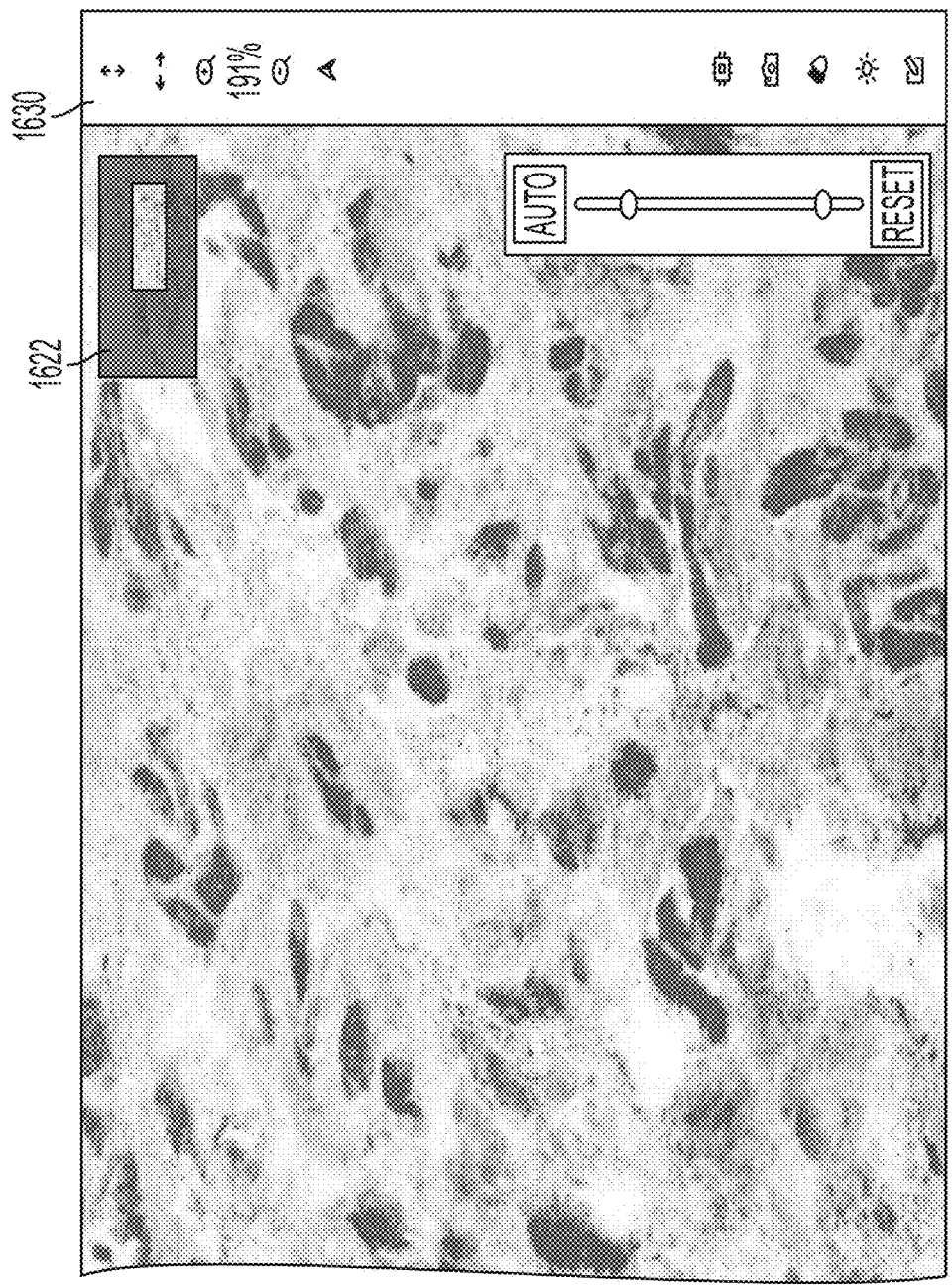
FIG. 16B is a second portion of the screenshot of FIG. 16A showing an illustrative image examiner screen, according to illustrative embodiments of the invention.

Referring to FIGS. 16A and 16B, an image examiner screen 1600 displayed using a user interface module can include an image contextual data pane 1610, an image area 1620 with navigator 1622, and an image toolbar 1630. In certain embodiments, an image contextual data pane includes one or more of an image timestamp and description interface 1612, a session (e.g., patient and operator) data interface 1614, a specimen location interface 1616, and a specimen surface orientation interface 1618. In certain embodiments, a user interface module is used to display a specimen location interface and a specimen surface orientation interface for use in receiving user input of location(s) and orientation(s), respectively.

The image examiner screen can include an image area with navigator 1622 and an image toolbar. Users can work with the image using image toolbar 1630 and navigate through the image (e.g., using regular touch screen gestures for image navigation or controls on the toolbar). For example, in certain embodiments, users can employ two fingers and pinch them inwards to zoom out or pinch them outwards to zoom in. A single touch anywhere within the image area can hide image contextual data pane and image toolbar, displaying the image area in a full screen view. A single touch on the full screen displayed image area can return the display of the previously hidden image contextual data pane and image toolbar. There can be a navigation map 1622 located in the image area. The navigation map 1622 can display, in miniature, the entire image and indicate which portion of the full image is currently displayed in the image area. The image toolbar 1630 can contain a set of tools that can be used to work with the displayed image. For example, the tools can include: fit to screen height, fit to screen width, zoom in, zoom level indicator, zoom out, orientation mark (e.g. a mark corresponding to a physical orientation mark present on the specimen imaging area), snapshot, image color mode (grayscale or color), brightness and contrast (e.g., adjustment sliders, auto adjustment, reset, etc.), annotations (e.g., adding graphical and textual annotations to the displayed image), free form annotation (e.g., adding free form annotations, adding a segment to a free form annotation, removing a segment from a free form annotation), line annotation (e.g., adding line annotations), pinpoint annotation (e.g., adding pinpoint annotations), text annotation (e.g., adding text annotations), delete annotation, and annotation visibility (e.g., showing or hiding the display of all annotations on the image). There may be an orientation marker (e.g., that can be toggled on and off) that displays a marker indicating the relation between how the image is oriented in image area 1620 and the specimen disposed on an imaging system. For example the left side of the image may correspond to the left side of a specimen as viewed from above by a user and an orientation marker may be used to demonstrate this relationship (for improved clarity to a user).

Referring back to FIG. 14, at step 1410, the system can receive a user's input of specimen location. The user can use the image contextual data pane to indicate the specimen location. In certain embodiments, a selection (e.g., input via a tap) of a specimen location interface in an image contextual data pane will open an enlarged version of the interface for user interaction (e.g., such that a user may more easily provide input to the interface). An illustrative specimen location interface 1700 for breast tissue specimens is shown in FIG. 17 (e.g., which may be an enlarged version of interface 1616). The specimen location interface 1700 can include a schematic view of two circles 1702 and 1704 representing the right the left breasts. Generally, when used for a particular type of specimen, the mapping interface 1700 may have schematics illustrating a relevant anatomical feature (e.g., organ). For example, when imaging specimens of ear tissue, a mapping interface 1700 may show a simplified schematic representation of an ear or likewise for a prostate or brain. A user interface module may allow a user to select a type of specimen that is being imaged so that the mapping interface 1700 shows the correct schematic. As such, in certain embodiments, users may freely update a mapping interface 1700 between surgical procedures (e.g., in an operating room). Data may be stored (e.g., in a database) that indicates which schematic is to be shown to a user when viewing images (e.g., in a report). The user can add to the interface a location indicating position where the specimen imaged during the current session is (or will be) located [e.g., that is then received and stored in a database (e.g., and associated with one or more images)]. In certain embodiments, a user can also add locations for specimens that were imaged in previous sessions (e.g., by opening a previously recorded image and using a specimen location interface 1700). In certain embodiments, each new image is associated with data indicating the location of the last image by default (e.g., unless revised by a user using a specimen location interface). Location data (e.g., as input in a specimen location interface) may be stored in a database and associated with an image and/or may be stored as image metadata.

At step 1412, an image of the surface of the tissue specimen can be obtained by the system. In certain embodiments, there are two modes to produce an image, including a "Preview" mode which allows rapid, low resolution imaging and an "Acquire" mode which allows high resolution imaging. Detailed embodiments of taking images using an imaging system are described in U.S. Provisional Patent Application Nos. 62/597,346 and 62/579,705.

In certain embodiments, images are presented using false coloring to mimic histological staining (e.g., a hematoxylin and eosin stain) which may have, for example, a pink/purple color scheme. In this way, a user may view images in a familiar color scheme that mimics traditional microscopy images as opposed to a fluorescent color scheme that may be generated by an imaging module. Use of false coloring may facilitate fast and easy interpretation of images. In certain embodiments, fluorescent images generated by an imaging system are converted to a purple/pink color scale that doctors are used to seeing from optical microscopy of stained samples. In certain embodiments, users are able to switch the color mode to grayscale.

In certain embodiments, the images generated by the system are very large. To locate an area of interest (e.g., a region of interest) on a displayed image, users can use zoom in and zoom out functions either with pinching gestures on a touch sensitive display or with dedicated zoom controls from the image toolbar. Contrast and brightness may be determined, by default for an entire image area. This may lead some areas of an image to appear too bright or dark and/or low contrast for easy interpretation. In certain embodiments, a user can use a built-in auto contrast/brightness function that only adjusts contrast and brightness for a portion of a large image that is displayed (e.g., when zoomed in). In certain embodiments, such a local contrast/brightness adjustment feature may not overwrite original image data, but rather may be exported as a new image to allow for later viewing. Metadata or associated data from the original image may be copied and/or associated with the new image when it is saved such that a user viewing the new image with modified contrast/brightness can view annotations, time stamp data, location data, orientation data, or any other such data that was associated with the original image. Users can also use the built-in auto contrast/brightness function to adjust the contrast and brightness of a displayed area of interest.

Delineating a region of interest (e.g., area of interest) may comprise defining external borders of a region of interest. Delineating may also comprise defining one or several internal cavities within a region of interest. In certain embodiments, the subsequent user input comprises graphical or data field information allowing to change previously entered graphical or textual annotations to a displayed image, including modifications to a delineated region of interest (for example, a change to the position of external borders of a delineated region, or a change to the borders of an internal cavity of such a region). Based on received user input, annotations may be associated with a displayed image, stored in a database and, for example according to user input through an annotation GUI, can be shown or hidden on the image display.

Figure 18:
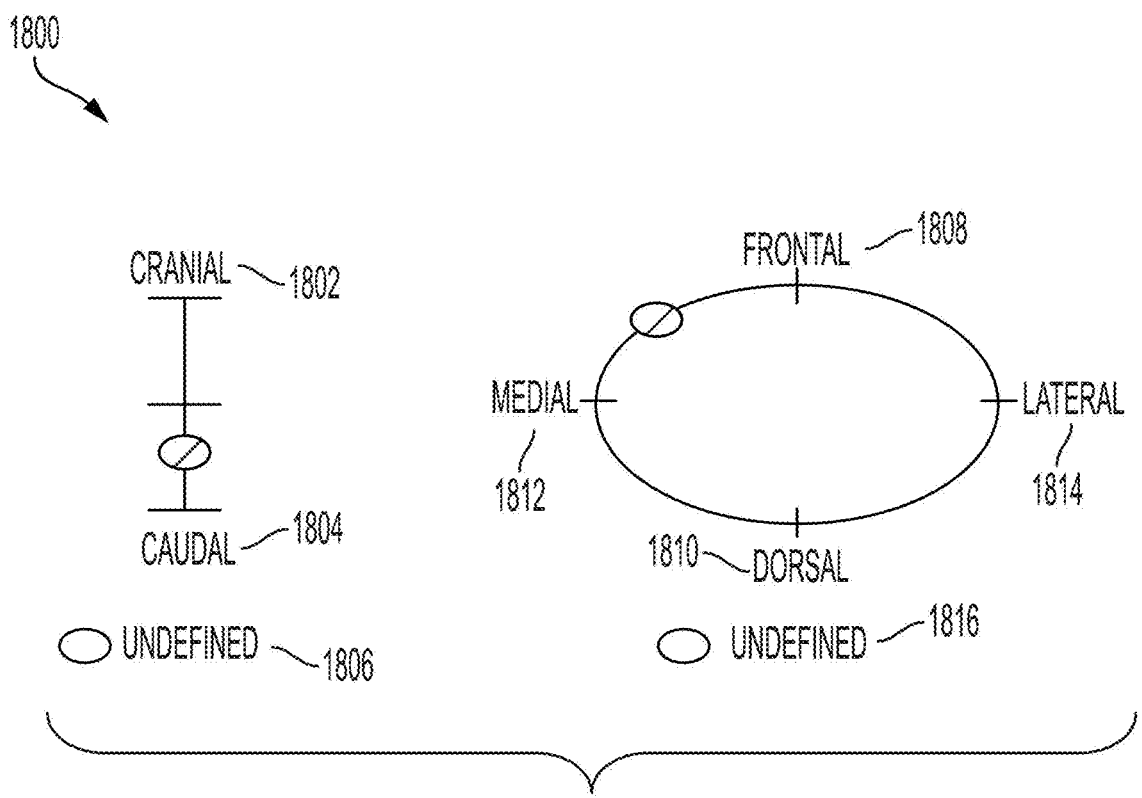
FIG. 18 is a screenshot showing an illustrative interface for marking specimen surface orientation, according to illustrative embodiments of the invention.

At step 1414, the system can receive the user's input of specimen surface orientation within the tissue (e.g., with respect to the body or anatomical structure). The user can use the image contextual data pane to indicate the specimen location. In certain embodiments, a selection (e.g., tap) of a specimen surface orientation interface in an image contextual data pane will open an enlarged version of the interface for user interaction (e.g., such that a user may more easily provide input to the interface). An illustrative specimen surface orientation interface 1800 is shown in FIG. 18 (e.g., which may be an enlarged version of interface 1618 shown in FIGS. 16A and 16B). Different surface orientations can be represented by various anatomical terms including "Cranial" 1802 and "Caudal" 1804 in the vertical (or longitudinal) axis, as well as "Frontal" 1808, "Dorsal" 1810, "Medial" 1812, and "Lateral" 1814 in the horizontal (or transverse) plane. The user can also label the specimen surface as "Undefined" 1806 in the vertical axis and/or "Undefined" 1816 in the horizontal plane. Orientation data (e.g., as input in a specimen surface orientation interface) may be stored in a database and associated with an image and/or may be stored as image metadata.

As shown in FIG. 18, in certain embodiments, complex orientations can be input and stored. Specimen surface orientation interface 1800 allows a user to input an orientation in a horizontal (transverse) plane using a circular element. Therefore, orientations that are partially between, for example, a frontal and medial or dorsal and lateral orientation can be accurately recorded. In certain embodiments, specimen (e.g., resected tissue samples) are relatively soft and can deform slightly when mounted for imaging and/or do not have well defined faces (e.g., are not strictly cubic or rectangular solids). For example, a resected tissue sample may appear ellipsoidal in shape. Therefore, when imaged, such a sample may not be disposed with strictly a frontal, medial, dorsal, or lateral orientation. Complex orientation interface elements (e.g., the circle shown in FIG. 18) allow users to input complex orientations easily for better records that may facilitate improved image analysis by a user. For example, when imaging in order to determine margins of a resected tissue sample (e.g., during a breast conservation procedure), accurate recordation of sample orientation may allow a user to resect additional tissue more precisely should positive (e.g., cancer containing) margins be found (i.e., by more accurately determining where in a patient the positive margins correspond).

In certain embodiments, a specimen surface orientation interface allows a user to input an orientation in a horizontal (transverse) plane by selecting one of at least 180 different orientations (e.g., at least 360 or at least 720 orientations) in the horizontal (transverse) plane. In certain embodiments, a specimen surface orientation interface allows a user to input different orientations in a horizontal (transverse plane) that have one or more of a frontal, medial, dorsal, and lateral component. In certain embodiments, a specimen surface orientation interface allows a user to input an orientation in a vertical axis along a continuous gradient between (and including) cranial and caudal orientations. In certain embodiments, a specimen surface orientation interface allows a user to input different orientations (e.g., of a large plurality of possible orientations) in a vertical axis each having one or more of a cranial and a caudal component.

At step 1416, tags and/or annotations can be added to the generated image. The user can tap an annotation toolbar button to activate the corresponding control, which may be used, for example, for free form annotation (e.g., adding free form annotations, adding a segment to a free form annotation, removing a segment from a free form annotation), line annotation (e.g., adding line annotations), pinpoint annotation (e.g., adding pinpoint annotations), and text annotation (e.g., adding text annotations). Tags and/or annotations may be made using input received from a user through one or more GUIs.

After the system generates the image of the specimen surface and annotations are added to the image, the user can reposition the specimen on the imaging window so that another surface of the specimen can be imaged. Steps 1406 to 1414 can then be repeated for the next surface of interest (e.g., on the same or different specimen).

Figure 19:
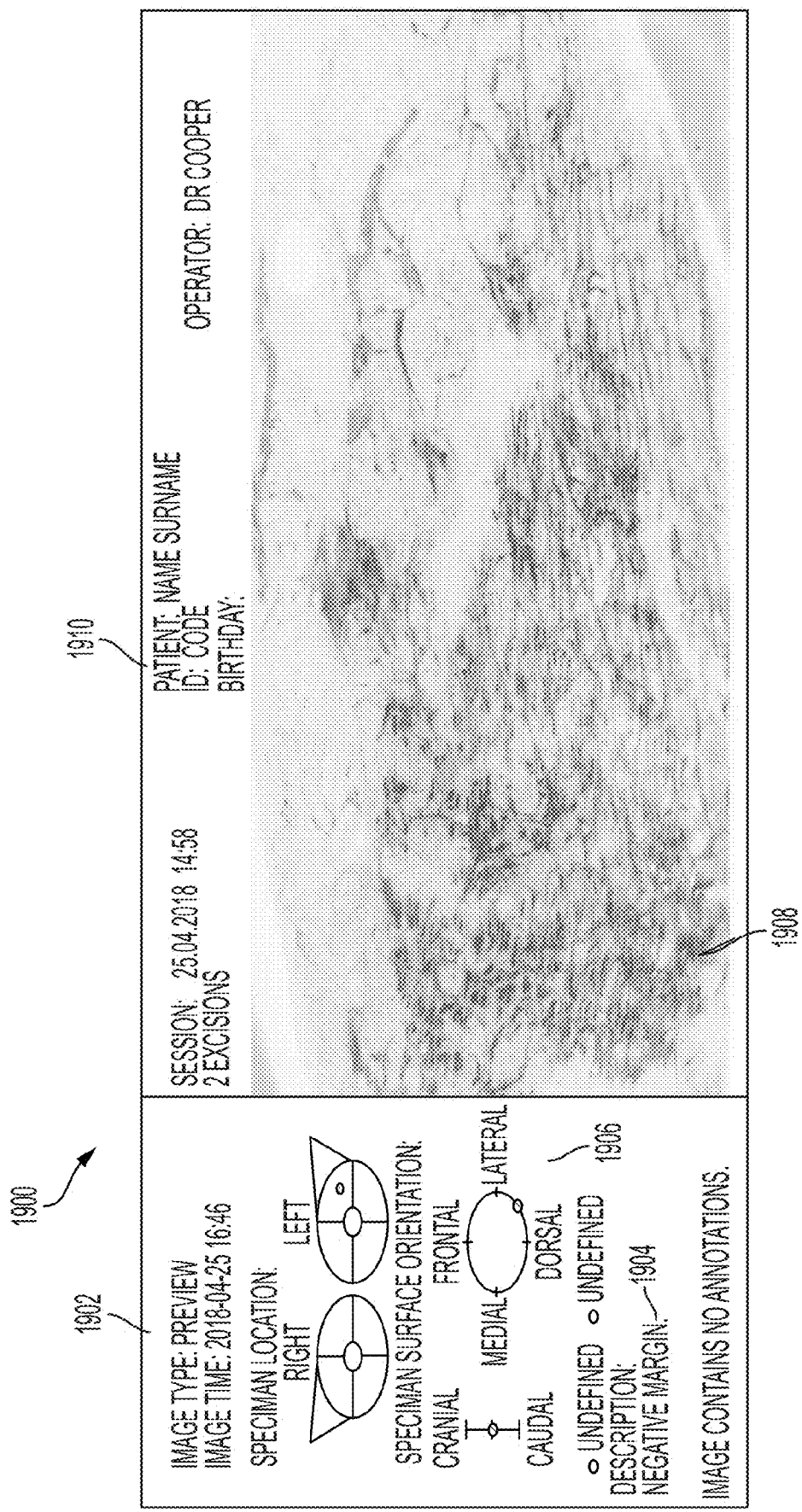
FIG. 19 is a screenshot of a page of an illustrative report that can be generated using a user interface module, according to illustrative embodiments of the invention.

After any number of images are taken, a report can be generated that summarizes the images [e.g., a session of images (e.g., corresponding to a single specimen)]. A report may generate as a file (e.g., in a proprietary format to be read by a user interface module used for image analysis) and/or as a document (e.g., PDF). FIG. 19 is a screenshot of a page 1900 of an illustrative report. Page 1900 includes image data 1902 representing the image type ("Preview") and a time stamp. Page 1900 includes description 1904, location and orientation information 1906, session data 1910, and image 1908. As can be seen in FIG. 19, in illustrative page 1900, image 1908 is of a surface of a sample resected from a location in an upper right quadrant of a left breast with an orientation midway between cranial and caudal in the vertical axis and nearest a dorsal orientation (although partly towards a lateral orientation) in a horizontal (transverse) plane. In certain embodiments, each page of a document report contains a different image and its associated data. As shown in page 1900, the image does not contain any annotations (e.g., highlights or markings). A document report may be generated by pulling image data (e.g., from an image session) and all associated data (e.g., location and/or orientation data, description data, and/or annotation data) and compiling a multi-page document that conveniently displays the image data with its corresponding associated data.

Illustrative Computing Systems and Computing Devices

Illustrative embodiments of systems and methods disclosed herein were described above with reference to computations performed locally by a computing device. However, computations performed over a network are also contemplated. FIG. 20 shows an illustrative network environment 2000 for use in the methods and systems described herein. In brief overview, referring now to FIG. 20, a block diagram of an illustrative cloud computing environment 2000 is shown and described. The cloud computing environment 2000 may include one or more resource providers 2002*a*, 2002*b*, 2002*c* (collectively, 2002). Each resource provider 2002 may include computing resources. In some implementations, computing resources may include any hardware and/or software used to process data. For example, computing resources may include hardware and/or software capable of executing algorithms, computer programs, and/or computer applications. In some implementations, illustrative computing resources may include application servers and/or databases with storage and retrieval capabilities. Each resource provider 2002 may be connected to any other resource provider 2002 in the cloud computing environment 2000. In some implementations, the resource providers 2002 may be connected over a computer network 2008. Each resource provider 2002 may be connected to one or more computing device 2004a, 2004b, 2004c (collectively, 2004), over the computer network 2008.

The cloud computing environment 2000 may include a resource manager 2006. The resource manager 2006 may be connected to the resource providers 2002 and the computing devices 2004 over the computer network 2008. In some implementations, the resource manager 2006 may facilitate the provision of computing resources by one or more resource providers 2002 to one or more computing devices 2004. The resource manager 2006 may receive a request for a computing resource from a particular computing device 2004. The resource manager 2006 may identify one or more resource providers 2002 capable of providing the computing resource requested by the computing device 2004. The resource manager 2006 may select a resource provider 2002 to provide the computing resource. The resource manager 2006 may facilitate a connection between the resource provider 2002 and a particular computing device 2004. In some implementations, the resource manager 2006 may establish a connection between a particular resource provider 2002 and a particular computing device 2004. In some implementations, the resource manager 2006 may redirect a particular computing device 2004 to a particular resource provider 2002 with the requested computing resource.

FIG. 21 shows an example of a computing device 2100 and a mobile computing device 2150 that can be used in the methods and systems described in this disclosure. The computing device 2100 is intended to represent various forms of digital computers, such as laptops, desktops, workstations, personal digital assistants, servers, blade servers, mainframes, and other appropriate computers. The mobile computing device 2150 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 2100 includes a processor 2102, a memory 2104, a storage device 2106, a high-speed interface 2108 connecting to the memory 2104 and multiple high-speed expansion ports 2110, and a low-speed interface 2112 connecting to a low-speed expansion port 2114 and the storage device 2106. Each of the processor 2102, the memory 2104, the storage device 2106, the high-speed interface 2108, the high-speed expansion ports 2110, and the low-speed interface 2112, are interconnected using various busses, and may be mounted on a common motherboard or in other manners as appropriate. The processor 2102 can process instructions for execution within the computing device 2100, including instructions stored in the memory 2104 or on the storage device 2106 to display graphical information for a GUI on an external input/output device, such as a display 2116 coupled to the high-speed interface 2108. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (e.g., one or more processors) of any number of computing devices (e.g., one or more computing devices). Furthermore, where a function is described as being performed by "a processor", this encompasses embodiments wherein the function is performed by any number of processors (e.g., one or more processors) of any number of computing devices (e.g., one or more computing devices) (e.g., in a distributed computing system).

The memory 2104 stores information within the computing device 2100. In some implementations, the memory 2104 is a volatile memory unit or units. In some implementations, the memory 2104 is a non-volatile memory unit or units. The memory 2104 may also be another form of computer-readable medium, such as a magnetic or optical disk.

The storage device 2106 is capable of providing mass storage for the computing device 2100. In some implementations, the storage device 2106 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 2102), perform one or more methods, such as those described above. The instructions can also be stored by one or more storage devices such as computer- or machine-readable mediums (for example, the memory 2104, the storage device 2106, or memory on the processor 2102).

The high-speed interface 2108 manages bandwidth-intensive operations for the computing device 2100, while the low-speed interface 2112 manages lower bandwidth-intensive operations. Such allocation of functions is an example only. In some implementations, the high-speed interface 2108 is coupled to the memory 2104, the display 2116 (e.g., through a graphics processor or accelerator), and to the high-speed expansion ports 2110, which may accept various expansion cards (not shown). In the implementation, the low-speed interface 2112 is coupled to the storage device 2106 and the low-speed expansion port 2114. The low-speed expansion port 2114, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 2100 may be implemented in a number of different forms, as shown in the figure. For example, it may be implemented as a standard server 2120, or multiple times in a group of such servers. In addition, it may be implemented in a personal computer such as a laptop computer 2122. It may also be implemented as part of a rack server system 2124. Alternatively, components from the computing device 2100 may be combined with other components in a mobile device (not shown), such as a mobile computing device 2150. Each of such devices may contain one or more of the computing device 2100 and the mobile computing device 2150, and an entire system may be made up of multiple computing devices communicating with each other.

The mobile computing device 2150 includes a processor 2152, a memory 2164, an input/output device such as a display 2154, a communication interface 2166, and a transceiver 2168, among other components. The mobile computing device 2150 may also be provided with a storage device, such as a micro-drive or other device, to provide additional storage. Each of the processor 2152, the memory 2164, the display 2154, the communication interface 2166, and the transceiver 2168, are interconnected using various buses, and several of the components may be mounted on a common motherboard or in other manners as appropriate.

The processor 2152 can execute instructions within the mobile computing device 2150, including instructions stored in the memory 2164. The processor 2152 may be implemented as a chipset of chips that include separate and multiple analog and digital processors. The processor 2152 may provide, for example, for coordination of the other components of the mobile computing device 2150, such as control of user interfaces, applications run by the mobile computing device 2150, and wireless communication by the mobile computing device 2150.

The processor 2152 may communicate with a user through a control interface 2158 and a display interface 2156 coupled to the display 2154. The display 2154 may be, for example, a TFT (Thin-Film-Transistor Liquid Crystal Display) display or an OLED (Organic Light Emitting Diode) display, or other appropriate display technology. The display interface 2156 may comprise appropriate circuitry for driving the display 2154 to present graphical and other information to a user. The control interface 2158 may receive commands from a user and convert them for submission to the processor 2152. In addition, an external interface 2162 may provide communication with the processor 2152, so as to allow near area communication of the mobile computing device 2150 with other devices. The external interface 2162 may provide, for example, for wired communication in some implementations, or for wireless communication in other implementations, and multiple interfaces may also be used.

The memory 2164 stores information within the mobile computing device 2150. The memory 2164 can be implemented as one or more of a computer-readable medium or media, a volatile memory unit or units, or a non-volatile memory unit or units. An expansion memory 2174 may also be provided and connected to the mobile computing device 2150 through an expansion interface 2172, which may include, for example, a SIMM (Single In Line Memory Module) card interface. The expansion memory 2174 may provide extra storage space for the mobile computing device 2150, or may also store applications or other information for the mobile computing device 2150. Specifically, the expansion memory 2174 may include instructions to carry out or supplement the processes described above, and may include secure information also. Thus, for example, the expansion memory 2174 may be provided as a security module for the mobile computing device 2150, and may be programmed with instructions that permit secure use of the mobile computing device 2150. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 2152), perform one or more methods, such as those described above. The instructions can also be stored by one or more storage devices, such as one or more computer- or machine-readable mediums (for example, the memory 2164, the expansion memory 2174, or memory on the processor 2152). In some implementations, the instructions can be received in a propagated signal, for example, over the transceiver 2168 or the external interface 2162.

The mobile computing device 2150 may communicate wirelessly through the communication interface 2166, which may include digital signal processing circuitry where necessary. The communication interface 2166 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 2168 using a radio-frequency. In addition, short-range communication may occur, such as using a Bluetooth®, Wi-Fi™, or other such transceiver (not shown). In addition, a GPS (Global Positioning System) receiver module 2170 may provide additional navigation- and location-related wireless data to the mobile computing device 2150, which may be used as appropriate by applications running on the mobile computing device 2150.

The mobile computing device 2150 may also communicate audibly using an audio codec 2160, which may receive spoken information from a user and convert it to usable digital information. The audio codec 2160 may likewise generate audible sound for a user, such as through a speaker, e.g., in a handset of the mobile computing device 2150. Such sound may include sound from voice telephone calls, may include recorded sound (e.g., voice messages, music files, etc.) and may also include sound generated by applications operating on the mobile computing device 2150.

The mobile computing device 2150 may be implemented in a number of different forms, as shown in the figure. For example, it may be implemented as a cellular telephone 2180. It may also be implemented as part of a smart-phone 2182, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input (e.g., using a touch screen).

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Additional Embodiments

It is understood that, in some embodiments, systems disclosed herein may be used for lithographic (e.g., photolithographic) purposes, wherein photons from a photon source are focused by an array of micro optical elements to expose a photon-sensitive material disposed at a focal plane of the array of micro optical elements with a pattern of micro optical elements. In some embodiments of systems disclosed herein used for lithography, a detector and any optics associated with the detector are not present.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description. Having described certain implementations of systems for imaging samples (e.g., intraoperative imaging of fresh resected tissue) and methods of their use, it will now become apparent to one of skill in the art that other implementations incorporating the concepts of the disclosure may be used. Therefore, the disclosure should not be limited to certain implementations, but rather should be limited only by the spirit and scope of the following claims.

What is claimed is:

1. A system for imaging of a sample, the system comprising:
   a transparent imaging window, wherein the transparent imaging window provides a surface onto or over which the sample is disposed during imaging of the sample;
   a photon source for providing an illumination beam;
   a beam splitter for directing the illumination beam toward the imaging window;
   a collimating lens for collimating the illumination beam over an area comparable in size to a field to be illuminated, thereby providing a collimated illumination beam, wherein the collimating lens is disposed between the imaging window and the beam splitter such that the illumination beam is directed to the collimating lens by the beam splitter;
   an optical chip, wherein the optical chip comprises an array of micro optical elements for focusing the collimated illumination beam onto a focal plane above or on the imaging window, wherein each micro optical element of the array of micro optical elements:
      (i) focuses a portion of the collimated illumination beam onto a tight focus, and
      (ii) directs back-emitted light from the sample through the collimating lens and towards the beam splitter;
   a detector, the detector comprising an array of detector elements, wherein the back-emitted light directed towards the beam splitter by each element of the array of optical elements of the optical chip passes through the beam splitter during imaging such that at least a portion of the back-emitted light is incident on the array of detector elements of the detector; and
   a scanning stage comprising a support, a controller, and an actuator,
      wherein: the optical chip is attached to the support and the controller and the actuator are operable to move the optical chip along a scan pattern relative to the imaging window and the detector during imaging in order to form an image of the sample,
      wherein the imaging window and the detector are in a fixed relative position.

2. The system of claim 1, wherein the photon source is a laser and the laser emits a wavelength of between 450 nm and 500 nm.

3. The system of claim 1, wherein the photon source is a laser that has a power of at least 5 mW.

4. The system of claim 1, comprising:
   a focusing lens disposed in an optical path of the illumination beam from the photon source to the beam splitter.

5. The system of claim 4, wherein the focusing lens has a focusing lens focal length and the collimating lens has a collimating lens focal length, each of which depends on a diameter of the illumination beam emitted by the photon source such that an illumination profile of the collimated illumination beam produced by the collimating lens is at least 48 mm×36 mm in area.

6. The system of claim 5, wherein the illumination profile has less than a 50% difference in intensity between an area of highest intensity in the illumination profile and an area of lowest intensity in the illumination profile.

7. The system of claim 5, wherein the photon source provides an illumination beam that is a Gaussian beam with a half-power beam width of less than 1.5 mm in diameter and the collimating lens focal length is at least 40× larger than the focusing lens focal length.

8. The system of claim 1, wherein the collimating lens is a cemented doublet lens.

9. The system of claim 1, wherein the collimating lens has a focal length of at least 100 mm.

10. The system of claim 1, wherein the collimating lens has a diameter of at least 50 mm.

11. The system of claim 1, comprising:
a filter for filtering undesired light, wherein the filter is disposed in an optical path of the back-emitted light such that at least a portion of the back-emitted light passes through the filter.

12. The system of claim 11, wherein the filter is disposed between the beam splitter and the detector along the optical path of the back-emitted light.

13. The system of claim 11, wherein the filter is a long-pass filter with cut-off wavelength of at least 500 nm.

14. The system of claim 11, wherein an opaque enclosure is disposed about an optical path of the back-emitted light that passes through the filter from the filter to the detector.

15. The system of claim 1, comprising an imaging lens for collimating the back-emitted light such that the back-emitted light is collimated by the imaging lens after passing through the beam splitter.

16. The system of claim 15, comprising an aperture disposed in an optical path of the back-emitted light between the beam splitter and the detector, wherein the optical chip, the collimating lens, the aperture, the imaging lens, and the detector are disposed in a 4f configuration.

17. The system of claim 15, wherein the imaging lens has a focal length of between 10 mm and 30 mm.

18. The system of claim 1, wherein the micro optical elements of the array of micro optical elements are disposed on a surface of the optical chip,
wherein areas on the surface of the optical chip between and/or around micro optical elements of the micro optical element array are coated with an absorptive and/or reflective layer,
wherein the absorptive and/or reflective layer acts as an aperture for each micro optical element and a diameter of each micro optical element is no smaller than a diameter of a corresponding aperture defined by the absorptive and/or reflective layer.

19. The system of claim 1, wherein the optical chip comprises fused silica.

20. The system of claim 1, wherein the imaging window comprises at least one of glass, quartz, sapphire, and plastic.

21. The system of claim 1, wherein the imaging window has a high Young's modulus of at least 100 GPa.

22. The system of claim 1, wherein the imaging window has a thickness of no more than 900 μm.

23. The system of claim 1, comprising a housing that at least partially encloses the system and exposes the sample to ambient conditions during imaging.

24. The system of claim 23, wherein the housing comprises a window support upon which a sample dish containing the sample may be disposed and held on or over the imaging window during imaging, such that the sample and the sample dish are accessible to a user during imaging.

25. The system of claim 24, wherein the window support is attached to the imaging window, and the window support and the imaging window are both sized and shaped to accommodate an optical interface of a sample dish.

26. The system of claim 1, comprising a kinematic support structure, the support structure supporting the imaging window such that height and tilt of the imaging window relative to the optical chip are adjustable.

27. The system of claim 1, comprising a computing device, wherein the computing device comprises a processor and a memory having instructions stored thereon that, when executed by the processor, cause the processor to produce an image based on the at least a portion of the back-emitted light detected by the detector.

28. The system of claim 27, wherein the memory has instructions stored thereon that, when executed by the processor, cause the processor to send information regarding the detected back-emitted light to a receiving device.

29. The system of claim 27, wherein the memory has instructions stored thereon that, when executed by the processor, cause the processor to:
connect the computing device, by the processor, with an operating theater display system; and
output, by the processor, imaging data to the operating theater display system.

30. The system of claim 27, the memory has instructions stored thereon that, when executed by the processor, cause the processor to:
connect, by the processor, to a radiology picture archiving and communication system (PACS) and/or a pathology PACS; and
at least one of (i) retrieve, by the processor, one or more stored images from the radiology PACS and/or the pathology PACS and (ii) store the image of the sample into the radiology PACS and/or the pathology PACS.

31. The system of claim 27, wherein the memory has instructions stored thereon that, when executed by the processor, cause the processor to:
connect the computing device, by the processor, to a laboratory information system; and
receive and/or send, by the processor, data to the laboratory information system.

32. The system of claim 27, wherein the memory has instructions stored thereon that, when executed by the processor, cause the processor to:
connect the computing device, by the processor, to an electronic patient record system; and
receive and/or send, by the processor, data to the electronic patient record system.

33. The system of claim 27, wherein the computing device is configured to connect to a cloud server for storing images.

34. The system of claim 27, wherein the memory has instructions stored thereon that, when executed by the processor, cause the processor to:
determine, by the processor, an area or volume of a 2D or 3D image of the sample that is indicative of cancer and/or high cancer risk, wherein the 2D or 3D image of the sample is obtained using the system; and
output, by the processor, a representation of the area or volume.

35. The system of claim 1, wherein the sample is stained with a fluorescent stain.

36. The system of claim 1, wherein the system is operable to image a portion of the sample in less than 2 minutes, wherein the portion of the sample has an area of at least 10 cm$^2$.

37. The system of claim 1, wherein the sample has a volume of no more than 10 cm×10 cm×10 cm and the system is configured to image a full outer surface of the sample in an imaging time of no more than 45 minutes.

38. The system of claim 1, wherein the system is a Class 1 laser product according to an ANSI standard and/or an IEC Standard.

39. The microscopy system of claim 1, wherein the photon source has reduced temporal coherence.

40. The microscopy system of claim 1, wherein the transparent imaging window comprises an anti-reflection coating disposed on a side opposite the optical chip.

* * * * *